(12) United States Patent
Kubota et al.

(10) Patent No.: US 9,181,332 B2
(45) Date of Patent: *Nov. 10, 2015

(54) ANTI-A(β) OLIGOMER HUMANIZED ANTIBODY

(71) Applicant: KYOWA HAKKO KIRIN CO., LTD., Tokyo (JP)

(72) Inventors: Tsuguo Kubota, Tokyo (JP); Nobuyuki Suzuki, Shizuoka (JP)

(73) Assignee: KYOWA HAKKO KIRIN CO., LTD, Tokyo (JP)

( * ) Notice: Subject to any disclaimer, the term of this patent is extended or adjusted under 35 U.S.C. 154(b) by 362 days.

This patent is subject to a terminal disclaimer.

(21) Appl. No.: 13/678,214

(22) Filed: Nov. 15, 2012

(65) Prior Publication Data

US 2013/0095526 A1 Apr. 18, 2013

Related U.S. Application Data

(62) Division of application No. 12/852,548, filed on Aug. 9, 2010, now Pat. No. 8,333,967.

(60) Provisional application No. 61/232,038, filed on Aug. 7, 2009.

(51) Int. Cl.
| | |
|---|---|
| *C12N 15/13* | (2006.01) |
| *C12N 15/63* | (2006.01) |
| *C12N 5/10* | (2006.01) |
| *C07K 16/18* | (2006.01) |
| *C12N 15/09* | (2006.01) |
| *A61K 39/00* | (2006.01) |

(52) U.S. Cl.
CPC ........... *C07K 16/18* (2013.01); *A61K 2039/505* (2013.01); *C07K 2317/24* (2013.01); *C07K 2317/92* (2013.01); *C07K 2319/00* (2013.01); *C12N 5/10* (2013.01); *C12N 15/09* (2013.01); *C12N 15/63* (2013.01)

(58) Field of Classification Search
CPC ............... C07K 16/18; C07K 2319/00; C07K 2137/92; C07K 2317/24; C07K 2317/76; C07K 2316/96; A61K 2039/505; C07H 21/04; C07H 21/00
See application file for complete search history.

(56) References Cited

U.S. PATENT DOCUMENTS

| | | | |
|---|---|---|---|
| 6,218,506 B1 | 4/2001 | Krafft et al. | |
| 8,552,156 B2 * | 10/2013 | Takayanagi et al. | 530/388.1 |
| 2005/0059591 A1 * | 3/2005 | Schenk et al. | 514/12 |
| 2006/0228349 A1 | 10/2006 | Acton et al. | |
| 2007/0148167 A1 | 6/2007 | Strohl | |
| 2010/0028357 A1 | 2/2010 | Matsubara et al. | |

FOREIGN PATENT DOCUMENTS

| | | |
|---|---|---|
| EP | 2210901 A1 | 7/2010 |
| EP | 2246427 A1 | 11/2010 |
| JP | 2006-509721 A | 3/2006 |
| JP | 2008-520553 A | 6/2008 |
| WO | 03/104437 A2 | 12/2003 |
| WO | WO 2006006693 A1 * | 1/2006 |
| WO | 2006/055178 A2 | 5/2006 |
| WO | 2009051220 A1 | 4/2009 |
| WO | 2009/099176 A1 | 8/2009 |

OTHER PUBLICATIONS

Rakez Kayed et al., "Conformation-Dependent Anti-Amyloid Oligomer Antibodies", Methods in Enzymology, Academic Press, US, vol. 413, Jan. 1, 2006, pp. 326-344, XP009115614.
Search Report dated Aug. 16, 2013, issued by the European Patent Office in counterpart European Patent Application No. 10806566.5.
Search Report dated Aug. 16, 2013, issued by the European Patent Office in European Patent Application No. 10806567.3.
Robert E. Bird et al, "Single-Chain Antigen-Binding Proteins", Science, 1988, 242: 423-426.
Man Sung Co et al., "Humanized Anti-Lewis Y Antibodies: In Vitro Properties and Pharmacokinetics in Rhesus Monkeys", Cancer Research, 1996, 26: 1118-1125.
Nigel S. Courtenay-Luck et al., "Development of Primary and Secondary Immune Responses to Mouse Monoclonal Antibodies Used in the Diagnosis and Therapy of Malignant Neoplasms", Cancer Research, 1986, 46: 6489-6493.
Robert O. Dillman et al., "Therapy of Chronic Lymphocytic Leukemia and Cutaneous T-Cell Lymphoma With T101 Monoclonal Antibody", Journal of Clinical Oncology, 1984, 2(8): 881-891.
Christian Haass et al., "Soluble protein oligomers in neurodegeneration: lessons from the Alzheimer's amyloid β-peptide", Nature Reviews: Molecular Cell Biology, 2007, 8: 101-112.
Alan N. Houghton et al., "Mouse monoclonal IgG3 antibody detecting $G_{D3}$ ganglioside: A phase l trial in patients with malignant melanoma", Proc. Natl. Acad. Sci. USA, 1985, 82: 1242-1246.
International Search Report issued Sep. 28, 2010 in PCT/JP2010/063431 (in the name of KYOWA HAKKO KIRIN CO., LTD.).
Japanese Patent Office, Office Action issued on Mar. 27, 2012, in corresponding Japanese Application No. 2011-525961.
M.B. Khazaeli et al., "Phase 1 Trial of Multiple Large Doses of Murine Monoclonal Antibody CO17-1A.: II. Pharmacokinetics and Immune Response", Journal of the National Cancer Institute, 1988, 80(12): 937-942.

(Continued)

*Primary Examiner* — Kimberly A Ballard
(74) *Attorney, Agent, or Firm* — Sughrue Mion, PLLC

(57) ABSTRACT

An anti-Aβ oligomer humanized antibody which does not bind to Aβ monomers and specifically binds only to Aβ oligomers; an anti-cognitive dysfunction agent, an agent for treating Alzheimer's disease, an agent for suppressing formation of neuritic plaque and an inhibitor of formation of Aβ amyloid fiber comprising the antibody as an active ingredient; a method for at least one of preventing and treating cognitive dysfunction or Alzheimer's disease, comprising the step of administering the antibody; and a method for suppressing progression of Alzheimer's disease, comprising the step of administering the antibody.

4 Claims, 3 Drawing Sheets

(56) References Cited

OTHER PUBLICATIONS

William L. Klein et al., "Targeting small Aβ oligomers: the solution to an Alzheimer's disease conundrum?", TRENDS in Neurosciences, 2001, 24(4): 219-224.
Roland E. Kontermann et al., "Complement recruitment using bispecific diabodies", Nature Biotechnology, 1997, 15: 629-631.
Mary Lambert et al., "Monoclonal antibodies that target pathological assemblies of Aβ", Journal of Neurochemistry, 2007, 100(1): 23-25.
Edward B. Lee et al., "Targeting Amyloid-β Peptide (Aβ) Oligomers by Passive Immunization with a Conformation-selective Monoclonal Antibody Improves Learning and Memory in Aβ Precursor Protein (APP) Transgenic Mice", Journal of Biological Chemistry, 2006, 281(7): 4292-4299.
Albert F. Lobuglio et al., "Phase 1 Trial of Multiple Large Doses of Murine Monoclonal Antibody CO17-1A.: 1. Clincal Aspects", Journal of the National Cancer Institute, 1988, 80(12): 932-936.
Etsuro Matsubara, "Alzheimer's Disease no Kotai Chiryo", Clinical Testing, 2008, 52(3): 297-301.
Timothy C. Meeker et al., "A Clinical Trial of Anti-Idiotype Therapy for B Cell Malignancy", Blood, 1985, 65(6): 1349-1363.
Patrick Mitchell et al., "Prevention of Intracerebral Haemorrhage", Current Drug Targets, 2007, 8(7): 832-838.
Cristina Monfardini et al., "Rational Design of Granulocyte-Macrophage Colony-stimulating Factor Antagonist Peptides", The Journal of Biological Chemistry, 1996, 271(6): 2966-2971.
Nadia Moretto et al., "Conformation-sensitive Antibodies against Alzheimer Amyloid-β by Immunization with a Thioredoxin-constrained B-cell Epitope Peptide", The Journal of Biological Chemistry, 2007, 282(15): 11436-11445.
Barbara M. Mueller et al., "Enhancement of Antibody-Dependent Cytotoxicity with a Chimeric Anti-GD2 Antibody", The Journal of Immunology, 1990, 144(4): 1382-1386.
Malcolm V. Pimm et al., "The Characteristics of Blood-Borne Radiolabels and the Effect of Anti-Mouse IgG Antibodies on Localization of Radiolabeled Monoclonal Antibody in Cancer Patients", J. Nucl. Med., 1985, 26(9): 1011-1023.
Lutz Riechmann et al., "Reshaping human antibodies for therapy", Nature, 1988, 332: 323-327.
Dennis J. Selkoe et al., "Alzheimer's Disease is a Synaptic Failure", Science, 2002, 298: 789-791.
Daniel L. Shawler et al., "Human Immune Response to Multiple Injections of Murine Monoclonal IgG", The Journal of Immunology, 1985, 135(2): 1530-1535.
Mikio Shoji, "Alzheimer's Disease no Kotai Chiryo", Amyloidosis Ni Kansuru Chosa Kenkyu Heisei 19 Nendo Sokatsu Buntan Kenkyu Hokokusho, 2008, p. 76-78.
S. Stephens et al., "Comprehensive pharmacokinetics of a humanized antibody and analysis of residual anti-idiotypic responses", Immunology, 1995, 85: 668-674.
James C. Vickers, "A Vaccine Against Alzheimer's Disease", Drugs Aging, 2002, 19(7): 487-494.
Keith O. Webber et al., "Preparation and Characterization of a Disulfide-Stabilized Fv Fragment of the Anti-Tac Antibody: Comparison with its Single-Chain Analog", Molecular Immunology, 1995, 32(4): 249-258.
Takashi Yokota et al., "Rapid Tumor Penetration of a Single-Chain Fv and Comparison with Other Immunoglobulin Forms", Cancer Research, 1992, 52: 3402-3408.

\* cited by examiner

Fig. 1

```
                1          2          3          4          5          6
       1234567890 1234567890 1234567890 1234567890 1234567890 1234567890
6E4HV0 QVQLVQSGAE VKKPGASVKV SCKASGYTFT SYWMHWVRQA PGQGLEWMGE INPRNGGTNN
HV2                     K                              RQ         F  M
HV3                     K                              RQ         F  I
HV4                     K                              RQ         F  I
HV5                     K                              RL         F  I
HV7a                    K                              RL         F  I
HV7b                    V                              RQ         F  I
HV9                     V                              RL         F  I
HV12                    L                              KL         F  I 7          8          9         10         11
       1234567890 1234567890 1234567890 1234567890 12345678
6E4HV0 NENFKRRVTI TADTSTSTAY MELSSLRSED TAVYYCARDG NYDPFAYWGQ GTLVTVSS
HV2    RV  I  A T
HV3    RV  I  A T                                  T
HV4    KV  I  A T                                  T
HV5    KV  I  A T                                  T
HV7a   KA  I  A K                                  T
HV7b   KA  I  V K                                  T
HV9    KA  I  V K                                  T
HV12   KA  L  V K                                  T
```

Fig. 2

| | | 1 | 2 | 3 | 4 | 5 6 |
|---|---|---|---|---|---|---|
| | 1234567890 | 1234567890 | 1234567890 | 1234567890 | 1234567890 | 1234567890 |
| 6E4LV0 | DIVMTQSPLS | LPVTPGEPAS | ISCRSSQSLV | HSNGNTYLHW | YLQKPGQSPQ | LLIYKVSNRF |
| LV2a | I | P | | | K | |
| LV2b | V | P | | | Q | |
| LV2c | I | L | | | Q | |
| LV2d | V | P | | | K | |
| LV3 | I | L | | | K | |
| LV4 | V | L | | | K | |

| | 7 | 8 | 9 | 10 | 11 | |
|---|---|---|---|---|---|---|
| | 1234567890 | 1234567890 | 1234567890 | 1234567890 | 1234567890 | 123 |
| LV0 | SGVPDRFSGS | GSGTDFTLKI | SRVEAEDVGV | YYCSQSTHVP | PYTFGQGTKL | EIK |
| LV2a | | | | F | | |
| LV2b | | | | F | | |
| LV2c | | | | F | | |
| LV2d | | | | Y | | |
| LV3 | | | | F | | |
| LV4 | | | | F | | |

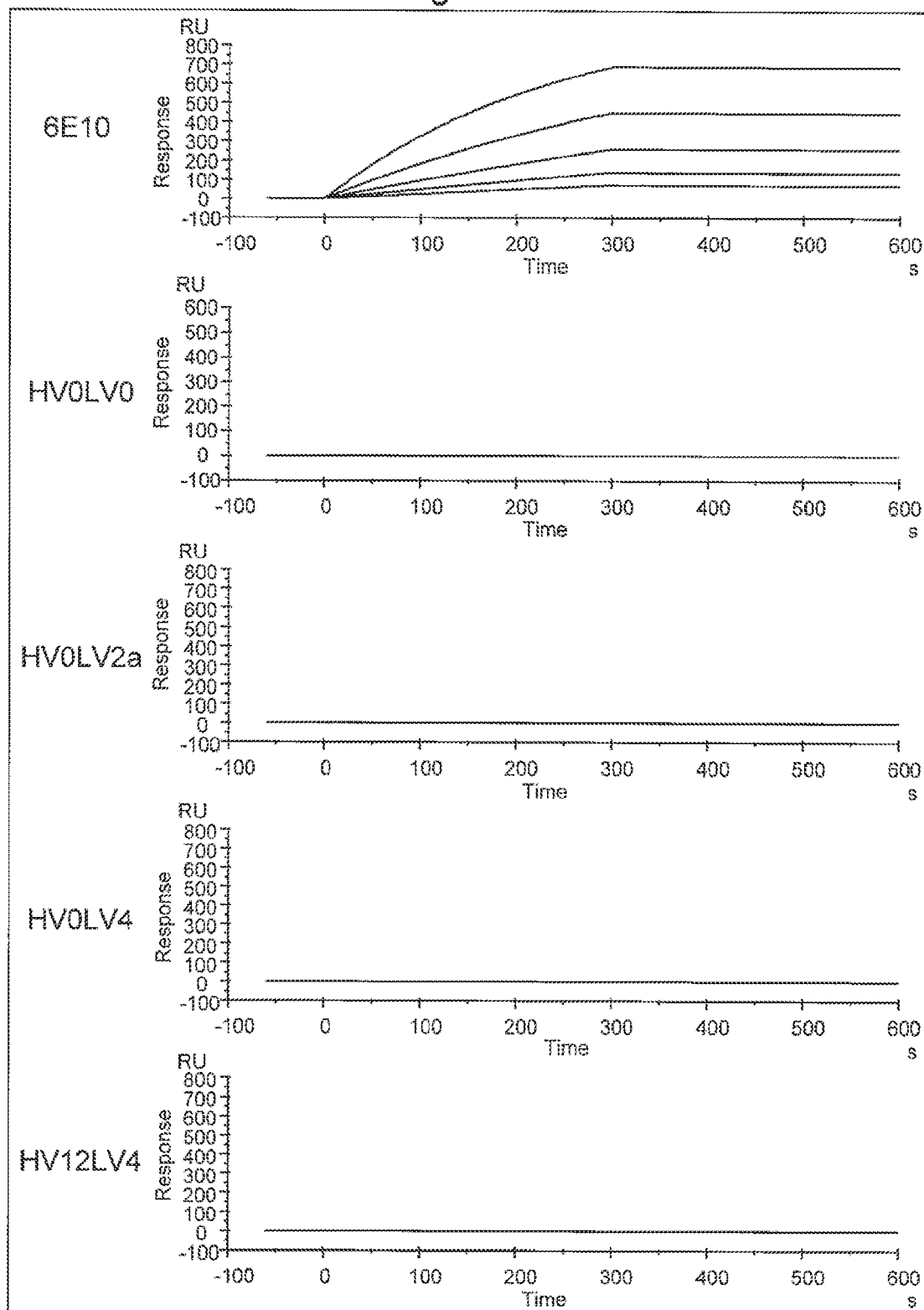

ANTI-A(β) OLIGOMER HUMANIZED ANTIBODY

CROSS-REFERENCE TO RELATED APPLICATIONS

This is a Divisional of U.S. Patent Application No. 12/852,548 filed Aug. 9, 2010, which claims priority to U.S. Provisional Patent Application No. 61/232,038 filed Aug. 7, 2009. The entire contents of the aforementioned applications are incorporated herein by reference.

BACKGROUND OF THE INVENTION

1. Field of the Invention

The present invention relates to an antibody which specifically binds to an amyloid-β (hereinafter, also referred to as Aβ) protein oligomer and use thereof.

2. Brief Description of the Background Art

It is considered based on various pieces of evidence that the decline in memory in Alzheimer's disease (hereinafter, referred to as AD) is caused as a result of synapse dysfunction due to soluble oligomers of amyloid-β protein (hereinafter, amyloid-β protein is also referred to as Aβ, and amyloid-β protein oligomer is also referred to as Aβ oligomer) (Non-Patent Documents 1 and 2).

Accordingly, there is a possibility that excessive accumulation or deposition of Aβ oligomers in a brain triggers a series of pathological cascades which may cause AD. This indicates a possibility that medical treatment targeting Aβ oligomers may be effective in delaying or preventing the onset and the progression in the disease stage of AD.

However, the knowledge relating to the neurodegeneration caused by a molecule responsible for this amyloid-cascade hypothesis as its core factor, particularly by Aβ oligomers was mainly demonstrated in experiments in vitro (Non-Patent Document 3) and was not directly demonstrated in vivo.

Since the structures specific to Aβ oligomers have not been studied in the in vivo experiments which have been reported before (Non-Patent Document 4), synaptic toxicity due to endogenous Aβ oligomers has not been clarified.

In addition, although studies have been carried out in various AD model mice, neuronal toxicity of Aβ oligomers in the brain of an AD patient has not yet been revealed.

Furthermore, it has not yet been established why the formation of neurofibrillary tangle (hereinafter, simply referred to as NFT) and the loss of nerve cell occurs prior to pathogenesis of neuritic plaque in the human entorhinal cortex and how Aβ oligomers relate to these tissue degeneration and dysfunctions.

As antibodies against Aβ oligomers, anti-Aβ oligomer mouse monoclonal antibody NAB61 (Non-Patent Document 4), 1A9, 2C3, E12, 1C10, and 4D3 (Patent Document 1) are known.

It is known that generally, when a non-human antibody such as a mouse antibody is administered to human, it is recognized as a foreign substance so that a human antibody for mouse antibody (human anti mouse antibody: HAMA) is induced in the human body. It is known that HAMA reacts with the administered mouse antibody to thereby induce side effects (Non-patent Documents 5 to 8), quickens disappearance of the mouse antibody from the body (Non-patent Documents 6, 9 and 10) and decreases therapeutic effect of the mouse antibody (Non-patent Documents 11 and 12).

In order to solve these problems, attempts have been made to prepare a recombinant antibody such as a human chimeric antibody and a humanized antibody from a non-human antibody using genetic recombination techniques.

A human chimeric antibody, a humanized antibody and the like have various advantages in clinical application to human in comparison with a non-human antibody such as a mouse antibody. For example, it has been reported that its immunogenicity was decreased and its blood half-life was prolonged in a test using monkey, compared to a mouse antibody (Non-patent Document 13).

That is, since a human chimeric antibody, a humanized antibody and the like cause fewer side effects in human than non-human antibodies, it is expected that its therapeutic effect is sustained for a prolonged time.

Also, since a recombinant antibody such as a human chimeric antibody, a humanized antibody and a human antibody is prepared using recombination techniques, it can be prepared as various forms of molecules.

For example, γ1 subclass can be used as a heavy chain (hereinafter referred to as "H chain") constant region (hereinafter referred to as "C region") of a human antibody (H chain C region is referred to as "CH") to produce a recombinant antibody having high effector functions such as antibody-dependent cellular cytotoxicity (hereinafter referred to as "ADCC activity"). In addition, γ2 or γ4 subclass can be used as a heavy chain to produce a recombinant antibody which has decreased effector function and is expected to prolong of its blood half life in comparison with mouse antibodies (Non-patent Document 14).

Particularly, since cytotoxic activities such as complement-dependent cytotoxicity (hereinafter referred to as "CDC activity") and ADCC activity via the Fc region (the region after the antibody heavy chain hinge region) of an antibody are important for the therapeutic efficacy, a human chimeric antibody, a humanized antibody or a human antibody is preferred compared to a non-human animal antibody such a mouse antibody (Non-patent Documents 15 and 16).

In addition, with recent advance in protein engineering and genetic engineering, the recombinant antibody can also be prepared as an antibody fragment having small molecular weight, such as Fab, Fab', F(ab')$_2$, a single chain antibody (hereinafter referred to as "scFv") (Non-patent Document 17), a dimerized V region fragment (hereinafter referred to as "Diabody") (Non-patent Document 18), a disulfide stabilized V region fragment (hereinafter referred to as "dsFv") (Non-patent Document 19), and a peptide comprising a CDR (Non-patent Document 20). These antibody fragments have a greater advantage in transfer to target tissues than whole antibody molecules (Non-patent Document 21).

The above-mentioned facts indicate that a human chimeric antibody, a humanized antibody, a human antibody or an antibody fragment thereof is more preferable as the antibody to be used for the clinical application to human than non-human antibodies, such as a mouse antibody.

CITATION LIST

Patent Literature

Patent Literature 1: WO2009/051220

Non-Patent Literature

Non-patent Literature 1: Klein W L, *Trends Neurosci* 24:219-224, 2001.
Non-patent Literature 2: Selkoe D J, *Science* 298:789-791, 2002.

Non-patent Literature 3: Hass C et al, *Nature Review* 8:101-12, 2007.
Non-patent Literature 4: Lee E B, et al, *J. Biol. Chem.* 281:4292-4299, 2006.
Non-patent Literature 5: *J. Clin. Oncol.*, 2, 881 (1984)
Non-patent Literature 6: *Blood*, 65, 1349 (1985)
Non-patent Literature 7: *J. Natl. Cancer Inst.*, 80, 932 (1988)
Non-patent Literature 8: *Proc. Natl. Acad. Sci., USA*, 82, 1242 (1985)
Non-patent Literature 9: *J. Nucl. Med.*, 26, 1011 (1985)
Non-patent Literature 10: *J. Nucl. Cancer Inst.*, 80, 937 (1988)
Non-patent Literature 11: *J. Immunol.*, 135, 1530 (1985)
Non-patent Literature 12: *Cancer Res.*, 46, 6489 (1986)
Non-patent Literature 13: *Cancer Res.*, 56, 1118 (1996)
Non-patent Literature 14: *Immunol.*, 85, 668 (1995)
Non-patent Literature 15: *J. Immunol.*, 144, 1382 (1990)
Non-patent Literature 16: *Nature*, 322, 323 (1988)
Non-patent Literature 17: *Science*, 242, 423 (1988)
Non-patent Literature 18: *Nature Biotechnol.*, 15, 629 (1997)
Non-patent Literature 19: *Molecular Immunol.*, 32, 249 (1995)
Non-patent Literature 20: *J. Biol. Chem.*, 271, 2966 (1996)
Non-patent Literature 21: *Cancer Res.*, 52, 3402 (1992)

SUMMARY OF THE INVENTION

The above Non-Patent Document 4 and Patent Document 1 disclose antibodies against Aβ oligomers. However, these antibodies bind not only to an Aβ oligomer but also to an Aβ monomer. Therefore, there is a concern about central side-effects of the antibody during the antibody therapy for AD, which targets the pathology in the brain.

For this reason, the purpose of the present invention is to provide a humanized antibody which does not bind to an Aβ monomer and specifically binds only to an Aβ oligomer and the use thereof. More specifically, the purpose is to provide an antibody which specifically binds to an Aβ oligomer, a method for measuring an Aβ oligomer using the antibody, a method for diagnosing AD using the antibody, and a medicament comprising the antibody.

As a result of intensive deliberation in view of the above problem, the present inventors have found a humanized antibody which does not bind to an Aβ monomer and specifically binds only to an Aβ oligomer and accomplished the present invention.

BRIEF DESCRIPTION OF THE DRAWINGS

FIG. 1 shows an amino acid sequence of H chain variable region HV1 and amino acid residues modified from the amino acid sequence represented by SEQ ID NO:12 in HV2, HV3, HV4, HV5, HV7a, HV7b, HV9 and HV12. The first and second lines in the drawing indicate the amino acid numbers in the H chain variable region, and the letters in the other respective lines indicate the substituted amino acid (represented by single letter code).

FIG. 2 shows an amino acid sequence of L chain variable region LV0 and amino acid residues modified from the amino acid sequence represented by SEQ ID NO:14 in LV2a, LV2b, LV2c, LV2d, LV3 and LV4. The first and second rows in the drawing indicate the amino acid numbers in the L chain variable region, and the letters in the respective rows indicate the altered amino acid (represented by one letter).

FIG. 3 shows sensorgrams obtained by measuring the binding activities of each anti-Aβ oligomer humanized antibody to Aβ monomers using a Biacore system.

DETAILED DESCRIPTION OF THE INVENTION

That is, the present invention relates to the following 1 to 9.
1. A humanized antibody which does not bind to an Aβ protein monomer and binds to an Aβ oligomer, and which comprises the following (a) antibody heavy chain variable region and (b) antibody light chain variable region:
   (a) an antibody heavy chain variable region comprising the amino acid sequence represented by SEQ ID NO:12 or an amino acid sequence in which at least one modification among amino acid modifications for substituting Lys at position 12 with Val, Val at position 20 with Leu, Arg at position 38 with Lys, Gln at position 39 with Leu, Leu at position 45 with Phe, Met at position 48 with Ile, Arg at position 67 with Lys, Val at position 68 with Ala, Ile at position 70 with Leu, Ala at position 72 with Val, Thr at position 74 with Lys and Ala at position 97 with Thr is carried out in the amino acid sequence represented by SEQ ID NO:12,
   (b) an antibody light chain variable region comprising the amino acid sequence represented by SEQ ID NO:14 or an amino acid sequence in which at least one modifications among amino acid modifications for substituting Ile at position 2 with Val, Pro at position 15 with Leu, Gln at position 50 with Lys, and Tyr at position 92 with Phe is carried out in the amino acid sequence represented by SEQ ID NO:14.
2. A humanized antibody according to the above 1, wherein the antibody heavy chain variable region comprises the amino acid sequence represented by SEQ ID NO:12 or 15 and the antibody light chain variable region comprises the amino acid sequence represented by SEQ ID NO:14, 16, or 17.
3. An anti-cognitive dysfunction agent, comprising the humanized antibody according to the above 1 or 2 as an active ingredient.
4. A medicament for treating Alzheimer's disease, comprising the humanized antibody according to the above 1 or 2 as an active ingredient.
5. An agent for suppressing formation of neuritic plaque, comprising the humanized antibody according to the above 1 or 2 as an active ingredient.
6. An inhibitor of formation of Aβ amyloid fiber, comprising the humanized antibody according to the above 1 or 2 as an active ingredient.
7. A method for at least one of prevention and treatment of cognitive dysfunction, comprising administering the humanized antibody according to the above 1 or 2.
8. A method for at least one of prevention and treatment of Alzheimer's disease, comprising administering the humanized antibody according to the above 1 or 2.
9. A method for suppressing progression of Alzheimer's disease, comprising administering the humanized antibody according to the above 1 or 2.

The antibody of the present invention is expected to establish methods for prevention and treatment of AD and a diagnostic marker at an early stage by targeting an Aβ protein which is a causative molecule of AD.

There is a concern about intracerebral transfer of the antibody during the antibody therapy for AD which targets the pathology in the brain. However, there is a possibility that the antibody of the present invention is applicable for the clinical therapy by administration to a peripheral vein, and it can be considered that development in the antibody treatment of AD should be accelerated at once.

The anti-Aβ oligomer humanized antibody of the present invention (hereinafter, also referred to as the antibody of the present invention or the humanized antibody of the present invention) is a humanized antibody characterized in that it binds to an Aβ oligomer and does not bind to an Aβ monomer. The antibody of the present invention is preferably an isolated antibody, a purified antibody, or an antibody composition.

The isolated antibody, the purified antibody, and the antibody composition are the antibodies which substantially comprise 100% of the desired antibody and do not contain any impurities such as contaminant proteins in the production of the antibody, derived from antibody-producing cells, tissues, antibody-producing animals and the like.

The antibody is a heterotetrameric protein constituted by two heavy chains (H chains) and two light chains (L chains). The antibody is classified as a polyclonal antibody and a monoclonal antibody which recognized a single antigen.

The polyclonal antibody is a mixture of the antibodies which recognize a single antigen. Examples of the polyclonal antibody include antiserum of a host animal immunized with an antigen.

The monoclonal antibody is an antibody secreted by a single clone of antibody-producing cells, and recognizes only one epitope (also called antigen determinant) and has the uniformity in amino acid sequence (primary structure).

The antibody of the present invention is preferably a monoclonal antibody. Examples of the monoclonal antibody in the present invention include a monoclonal antibody in which complementarity determining regions (hereinafter, referred to as CDRs) 1 to 3 of the antibody heavy chain (hereinafter, referred to as an H chain) comprise the amino acid sequences represented by SEQ ID NOs:1 to 3, respectively, and the CDRs 1 to 3 in the L chain comprise the amino acid sequences represented by SEQ ID NOs:4 to 6, respectively, a monoclonal antibody in which the H chain variable region (hereinafter, referred to as VH) of the antibody comprises the amino acid sequence represented by SEQ ID NO:8 and the L chain variable region (hereinafter, referred to as VL) comprises the amino acid sequence represented by SEQ ID NO:10, and an anti-Aβ oligomer mouse monoclonal antibody 6E4.

As an epitope, a single amino acid sequence which is recognized and bound by the monoclonal antibody, a conformation comprising the above amino acid sequence, the above amino acid sequence to which a sugar chain binds, and a conformation comprising the above amino acid sequences to which sugar chains bind can be exemplified.

The epitope to be recognized by the antibody of the present invention may be any protein so long as it includes at least one of an Aβ protein and the fragment thereof, and it exists on an Aβ oligomer which forms a complex.

Examples of the epitope to which the antibody of the present invention binds include an epitope comprising a primary amino acid sequence of Aβ which is exposed on an Aβ oligomer, an epitope comprising a conformation of an Aβ oligomer and the like.

It is known that the Aβ protein as a main component of amyloid is a peptide comprising 40 to 42 amino acids and is produced from a precursor protein called an amyloid precursor protein (hereinafter, referred to as APP) by the action of protease.

Amyloid molecules produced from APP include a non-fibrillar-polymer of soluble monomers and soluble oligomers in addition to the amyloid fiber collected in an ultracentrifugal sediment fraction.

In the present invention, the Aβ oligomer is a non-fibrillar-polymer, and is an Aβ oligomer which comprises at least one of an Aβ protein and a fragment thereof and forms a complex.

Specifically, examples of an Aβ oligomer include an Aβ40 (Aβ1-40) oligomer, an Aβ42(Aβ1-42) oligomer, and an Aβ oligomer comprising at least one of Aβ40 and Aβ42.

In addition, examples of the Aβ oligomer in the present invention also include an Aβ oligomer comprising an Aβ fragment with the loss of the N-terminal of Aβ in at least one of Aβ40 and Aβ42.

Specifically, the Aβ42 oligomer in the present invention are molecules having a molecular weight of 45 to 160 kDa measured by SDS-PAGE and a molecular weight of 22.5 to 1,035 kDa measured by Blue Native-PAGE.

The Aβ42 oligomer is recovered mainly through >100 kDa retaining liquid in the molecular sieve. In addition, the Aβ oligomer shows a mixture of configuration which consists of particle-shaped molecules, beaded molecules, and circular molecules with the heights of 1.5 to 3.1 nm under an atomic force microscope.

Moreover, the above Aβ42 oligomer is eluted to a void volume fraction 8 of the molecular weight 680 kDa or more and to a fraction 15 of the molecular weight 17 to 44 kDa boundary by gel filtration method.

The antibody of the present invention can be used as long as it is a humanized antibody which binds to an Aβ oligomer and does not bind to an Aβ monomer, and the derivation and shape thereof are not limited.

It is preferable that the antibody of the present invention does not recognize a soluble amyloid β (Aβ) monomer which is a physiological molecule and reacts only with a soluble Aβ oligomer.

In the present invention, binding only to a soluble Aβ oligomer without binding to a soluble Aβ monomer means that, among Aβ monomers and Aβ oligomers which are separated by ultrafiltration and a molecular sieve, the antibody does not recognize monomers (about 4.5 kDa), but specifically recognize a soluble Aβ oligomer which is equal to or larger than Aβ dimmers. Accordingly, it is preferable that the antibody of the present invention specifically binds to a soluble Aβ oligomer which is equal to, or larger than an Aβ dimer.

The antibody of the present invention has preferably at least one activity among the following (1) to (5):
(1) anti-neurotoxicity activity;
(2) Aβ amyloid fiber formation suppressing activity;
(3) specificity for recognizing only an Aβ oligomer;
(4) ability of capturing an Aβ oligomer in AD brains
(5) ability of preventing AD-like pathogenesis (decline in memory, Aβ accumulation level in brains) in an APPswe-transgenic mouse (Tg2576).

The activities of the antibody of the present invention relating to the above (1) to (5) can be confirmed using the method disclosed in WO 2009/051220.

The antibody of the present invention can be prepared as a recombinant antibody. In the present invention, the recombinant antibody includes antibodies produced by recombination technology such as a human chimeric antibody, a humanized antibody (or a human CDR-grafted antibody), a human antibody and an antibody fragment thereof.

The recombinant antibody, having a character of monoclonal antibodies, low immunogenecity and prolonged half-life in blood is preferable as a therapeutic agent. Examples of the recombinant antibody include an antibody derived by modification of the monoclonal antibody of the present invention using recombination technology.

The human chimeric antibody is an antibody comprising a heavy chain variable region (hereinafter referred to as "VH") and a light chain variable region (hereinafter referred to as "VL") of an antibody of a non-human animal and a heavy chain constant region (hereinafter referred to as "CH") and a light chain constant region (hereinafter referred to as "CL") of a human antibody.

The human chimeric antibody can be produced by obtaining cDNAs encoding the above VH and VL from a hybridoma which produces a monoclonal antibody that specifically binds to an Aβ oligomer, inserting each of them into an expression vector for animal cell comprising DNAs encoding the CH and CL to thereby construct a vector for expression of human chimeric antibody, and then introducing the vector into an animal cell to express the antibody.

As the above CH of the human chimeric antibody, any CH can be used, so long as it belongs to human immunoglobulin (hereinafter referred to as "hIg"), and those belonging to the hIgG class are preferred, and any one of the subclasses belonging to the hIgG class, such as hIgG1, hIgG2, hIgG3 and hIgG4, can be used.

As the above CL of the human chimeric antibody, any CL can be used, so long as it belongs to the hIg class, and those belonging to κ class or λ class can be used.

The humanized antibody of the present invention is an antibody in which amino acid sequences of CDRs of VH and VL of an antibody derived from a non-human animal are grafted into appropriate positions of VH and VL of a human antibody.

The humanized antibody can be produced by designing amino acid sequence of V regions in which the amino acid sequences of CDRs of both VH and VL of the monoclonal antibody which is produced by a non-human animal hybridoma and specifically binds to an Aβ oligomer are grafted into framework regions (hereinafter referred to as "FR") of VH and VL of any human antibody, respectively, constructing cDNAs encoding the V regions, inserting each of them into a expression vector for animal cells comprising genes encoding CH and CL of a human antibody to thereby construct a vector for expression of humanized antibody, and introducing it into an animal cell to thereby express and produce the humanized antibody.

As the amino acid sequences of FRs of VH and VL of the humanized antibody, any amino acid sequences can be used, so long as they are amino acid sequences of VH and VL, respectively, derived from a human antibody.

Examples include amino acid sequences of FRs of VH and VL of human antibodies registered in database such as Protein Data Bank, common amino acid sequences of each subgroup of FRs of VH and VL of human antibodies described in *Sequences of Proteins of Immunological Interest*, US Dept. Health and Human Services (1991) and the like.

Examples of the humanized antibody of the present invention include a humanized antibody in which CDRs 1 to 3 of VH of the antibody comprise the amino acid sequences represented by SEQ ID NOs:1 to 3, respectively, and CDRs 1 to 3 of VL of the antibody comprise the amino acid sequences represented by SEQ ID NOs:4 to 6, respectively.

The humanized antibody of the present invention is preferably a humanized antibody comprising at least one of the following (a) VH and (b) VL. In addition, in the following (a) and (b), the number of the substitutions to be introduced is not limited: (a) VH comprising the amino acid sequence represented by SEQ ID NO:12 or an amino acid sequence in which at least one amino acid residue selected from Lys at position 12, Val at position 20, Arg at position 38, Gln at position 39, Leu at position 45, Met at position 48, Arg at position 67, Val at position 68, Ile at position 70, Ala at position 72, Thr at position 74 and Ala at position 97 in the amino acid sequence represented by SEQ ID NO:12 is substituted with another amino acid residue; (b) VL comprising the amino acid sequence represented by SEQ ID NO:14 or an amino acid sequence in which at least one amino acid residue selected from Ile at position 2, Pro at position 15, Gln at position 50, and Tyr at position 92 in the amino acid sequence represented by SEQ ID NO:14 is substituted with another amino acid residue.

Preferable examples of VH contained in the humanized antibody of the present invention include, for example, VH comprising an amino acid sequence in which Lys at position 12, Val at position 20, Arg at position 38, Gln at position 39, Leu at position 45, Met at position 48, Arg at position 67, Val at position 68, Ile at position 70, Ala at position 72, Thr at position 74 and Ala at position 97 in the amino acid sequence represented by SEQ ID NO:12 are substituted with other amino acid residues.

In addition, VH selected from the following (1) to (9) is also preferable as VH contained in the humanized antibody of the present invention:

(1) VH comprising an amino acid sequence in which Lys at position 12, Val at position 20, Arg at position 38, Gln at position 39, Leu at position 45, Met at position 48, Arg at position 67, Val at position 68, Ala at position 72, Thr at position 74, and Ala at position 97 in the amino acid sequence represented by SEQ ID NO:12 are substituted with other amino acid residues;

(2) VH comprising an amino acid sequence in which Lys at position 12, Arg at position 38, Gln at position 39, Leu at position 45, Met at position 48, Arg at position 67, Val at position 68, Ala at position 72, Thr at position 74 and Ala at position 97 in the amino acid sequence represented by SEQ ID NO:12 are substituted with other amino acid residues;

(3) VH comprising an amino acid sequence in which Lys at position 12, Gln at position 39, Leu at position 45, Met at position 48, Arg at position 67, Val at position 68, Ala at position 72, Thr at position 74 and Ala at position 97 in the amino acid sequence represented by SEQ ID NO:12 are substituted with other amino acid residues;

(4) VH comprising an amino acid sequence in which Gln at position 39, Leu at position 45, Met at position 48, Arg at position 67, Val at position 68, Thr at position 74 and Ala at position 97 in the amino acid sequence represented by SEQ ID NO:12 are substituted with other amino acid residues;

(5) VH comprising an amino acid sequence in which Leu at position 45, Met at position 48, Arg at position 67, Val at position 68, Ala at position 72, Thr at position 74 and Ala at position 97 in the amino acid sequence represented by SEQ ID NO:12 are substituted with other amino acid residues;

(6) VH comprising an amino acid sequence in which Gln at position 39, Leu at position 45, Met at position 48, Arg at position 67 and Ala at position 97 in the amino acid sequence represented by SEQ ID NO:12 are substituted with other amino acid residues;

(7) VH comprising an amino acid sequence in which Leu at position 45, Met at position 48, Arg at position 67 and Ala at position 97 in the amino acid sequence represented by SEQ ID NO:12 are substituted with other amino acid residues;

(8) VH comprising an amino acid sequence in which Leu at position 45, Met at position 48 and Ala at position 97 in the amino acid sequence represented by SEQ ID NO:12 are substituted with other amino acid residues;
(9) VH comprising an amino acid sequence in which Leu at position 45 and Ala at position 97 in the amino acid sequence represented by SEQ ID NO:12 are substituted with other amino acid residues.

Examples of the amino acid sequence of VH include an amino acid sequence in which at least one modification selected from modifications of substituting Lys at position 12 with Val, Val at position 20 with Leu, Arg at position 38 with Lys, Gln at position 39 with Leu, Leu at position 45 with Phe, Met at position 48 with Ile, Arg at position 67 with Lys, Val at position 68 with Ala, Ile at position 70 with Leu, Ala at position 72 with Val, Thr at position 74 with Lys and Ala at position 97 with Thr in the amino acid sequence represented by SEQ ID NO:12 is introduced.

More specific examples of the amino acid sequence of VH include the amino acid sequences in which the following twelve to one substitutions are introduced.

Specific examples of the amino acid sequence of VH in which twelve substitutions are introduced include an amino acid sequence in which Lys at position 12 is substituted with Val, Val at position 20 is substituted with Leu, Arg at position 38 is substituted with Lys, Gln at position 39 is substituted with Leu, Leu at position 45 is substituted with Phe, Met at position 48 is substituted with Ile, Arg at position 67 is substituted with Lys, Val at position 68 is substituted with Ala, Ile at position 70 is substituted with Leu, Ala at position 72 is substituted with Val, Thr at position 74 is substituted with Lys and Ala at position 97 is substituted with Thr in the amino acid sequence represented by SEQ ID NO:12.

Specific examples of the amino acid sequence of VH in which eleven substitutions are introduced include the following (1) to (12) amino acid sequences:

(1) an amino acid sequence in which Val at position 20 is substituted with Leu, Arg at position 38 is substituted with Lys, Gln at position 39 is substituted with Leu, Leu at position 45 is substituted with Phe, Met at position 48 is substituted with Ile, Arg at position 67 is substituted with Lys, Val at position 68 is substituted with Ala, Ile at position 70 is substituted with Leu, Ala at position 72 is substituted with Val, Thr at position 74 is substituted with Lys and Ala at position 97 is substituted with Thr in the amino acid sequence represented by SEQ ID NO:12;

(2) an amino acid sequence in which Lys at position 12 is substituted with Val, Arg at position 38 is substituted with Lys, Gln at position 39 is substituted with Leu, Leu at position 45 is substituted with Phe, Met at position 48 is substituted with Ile, Arg at position 67 is substituted with Lys, Val at position 68 is substituted with Ala, Ile at position 70 is substituted with Leu, Ala at position 72 is substituted with Val, Thr at position 74 is substituted with Lys and Ala at position 97 is substituted with Thr in the amino acid sequence represented by SEQ ID NO:12;

(3) an amino acid sequence in which Lys at position 12 is substituted with Val, Val at position 20 is substituted with Leu, Gln at position 39 is substituted with Leu, Leu at position 45 is substituted with Phe, Met at position 48 is substituted with Ile, Arg at position 67 is substituted with Lys, Val at position 68 is substituted with Ala, Ile at position 70 is substituted with Leu, Ala at position 72 is substituted with Val, Thr at position 74 is substituted with Lys and Ala at position 97 is substituted with Thr in the amino acid sequence represented by SEQ ID NO:12;

(4) an amino acid sequence in which Lys at position 12 is substituted with Val, Val at position 20 is substituted with Leu, Arg at position 38 is substituted with Lys, Leu at position 45 is substituted with Phe, Met at position 48 is substituted with Ile, Arg at position 67 is substituted with Lys, Val at position 68 is substituted with Ala, Ile at position 70 is substituted with Leu, Ala at position 72 is substituted with Val, Thr at position 74 is substituted with Lys and Ala at position 97 is substituted with Thr in the amino acid sequence represented by SEQ ID NO:12;

(5) an amino acid sequence in which Lys at position 12 is substituted with Val, Val at position 20 is substituted with Leu, Arg at position 38 is substituted with Lys, Gln at position 39 is substituted with Leu, Met at position 48 is substituted with Ile, Arg at position 67 is substituted with Lys, Val at position 68 is substituted with Ala, Ile at position 70 is substituted with Leu, Ala at position 72 is substituted with Val, Thr at position 74 is substituted with Lys and Ala at position 97 is substituted with Thr in the amino acid sequence represented by SEQ ID NO:12;

(6) an amino acid sequence in which Lys at position 12 is substituted with Val, Val at position 20 is substituted with Leu, Arg at position 38 is substituted with Lys, Gln at position 39 is substituted with Leu, Leu at position 45 is substituted with Phe, Arg at position 67 is substituted with Lys, Val at position 68 is substituted with Ala, Ile at position 70 is substituted with Leu, Ala at position 72 is substituted with Val, Thr at position 74 is substituted with Lys and Ala at position 97 is substituted with Thr in the amino acid sequence represented by SEQ ID NO:12;

(7) an amino acid sequence in which Lys at position 12 is substituted with Val, Val at position 20 is substituted with Leu, Arg at position 38 is substituted with Lys, Gln at position 39 is substituted with Leu, Leu at position 45 is substituted with Phe, Met at position 48 is substituted with Ile, Val at position 68 is substituted with Ala, Ile at position 70 is substituted with Leu, Ala at position 72 is substituted with Val, Thr at position 74 is substituted with Lys and Ala at position 97 is substituted with Thr in the amino acid sequence represented by SEQ ID NO:12;

(8) an amino acid sequence in which Lys at position 12 is substituted with Val, Val at position 20 is substituted with Leu, Arg at position 38 is substituted with Lys, Gln at position 39 is substituted with Leu, Leu at position 45 is substituted with Phe, Met at position 48 is substituted with Ile, Arg at position 67 is substituted with Lys, Ile at position 70 is substituted with Leu, Ala at position 72 is substituted with Val, Thr at position 74 is substituted with Lys and Ala at position 97 is substituted with Thr in the amino acid sequence represented by SEQ ID NO:12;

(9) an amino acid sequence in which Lys at position 12 is substituted with Val, Val at position 20 is substituted with Leu, Arg at position 38 is substituted with Lys, Gln at position 39 is substituted with Leu, Leu at position 45 is substituted with Phe, Met at position 48 is substituted with Ile, Arg at position 67 is substituted with Lys, Val at position 68 is substituted with Ala, Ala at position 72 is substituted with Val, Thr at position 74 is substituted with Lys and Ala at position 97 is substituted with Thr in the amino acid sequence represented by SEQ ID NO:12;

(10) an amino acid sequence in which Lys at position 12 is substituted with Val, Val at position 20 is substituted with Leu, Arg at position 38 is substituted with Lys, Gln at position 39 is substituted with Leu, Leu at position 45 is substituted with Phe, Met at position 48 is substituted with Ile, Arg at position 67 is substituted with Lys, Val at position 68 is substituted with Ala, Ile at position 70 is substituted with Leu, Thr at position 74 is substituted with Lys and Ala at position 97 is substituted with Thr in the amino acid sequence represented by SEQ ID NO:12;

(11) an amino acid sequence in which Lys at position 12 is substituted with Val, Val at position 20 is substituted with Leu, Arg at position 38 is substituted with Lys, Gln at position 39 is substituted with Leu, Leu at position 45 is substituted with Phe, Met at position 48 is substituted with Ile, Arg at position 67 is substituted with Lys, Val at position 68 is substituted with Ala, Ile at position 70 is substituted with Leu, Ala at position 72 is substituted with Val and Ala at position 97 is substituted with Thr in the amino acid sequence represented by SEQ ID NO:12;

(12) an amino acid sequence in which Lys at position 12 is substituted with Val, Val at position 20 is substituted with Leu, Arg at position 38 is substituted with Lys, Gln at position 39 is substituted with Leu, Leu at position 45 is substituted with Phe, Met at position 48 is substituted with Ile, Arg at position 67 is substituted with Lys, Val at position 68 is substituted with Ala, Ile at position 70 is substituted with Leu, Ala at position 72 is substituted with Val and Thr at position 74 is substituted with Lys in the amino acid sequence represented by SEQ ID NO:12.

Specific examples of the amino acid sequence of VH in which ten substitutions are introduced include the following (1) to (66) amino acid sequences, for example:

(1) an amino acid sequence in which Arg at position 38 is substituted with Lys, Gln at position 39 is substituted with Leu, Leu at position 45 is substituted with Phe, Met at position 48 is substituted with Ile, Arg at position 67 is substituted with Lys, Val at position 68 is substituted with Ala, Ile at position 70 is substituted with Leu, Ala at position 72 is substituted with Val, Thr at position 74 is substituted with Lys and Ala at position 97 is substituted with Thr in the amino acid sequence represented by SEQ ID NO:12;

(2) an amino acid sequence in which Val at position 20 is substituted with Leu, Gln at position 39 is substituted with Leu, Leu at position 45 is substituted with Phe, Met at position 48 is substituted with Ile, Arg at position 67 is substituted with Lys, Val at position 68 is substituted with Ala, Ile at position 70 is substituted with Leu, Ala at position 72 is substituted with Val, Thr at position 74 is substituted with Lys and Ala at position 97 is substituted with Thr in the amino acid sequence represented by SEQ ID NO:12;

(3) an amino acid sequence in which Val at position 20 is substituted with Leu, Arg at position 38 is substituted with Lys, Leu at position 45 is substituted with Phe, Met at position 48 is substituted with Ile, Arg at position 67 is substituted with Lys, Val at position 68 is substituted with Ala, Ile at position 70 is substituted with Leu, Ala at position 72 is substituted with Val, Thr at position 74 is substituted with Lys and Ala at position 97 is substituted with Thr in the amino acid sequence represented by SEQ ID NO:12;

(4) an amino acid sequence in which Val at position 20 is substituted with Leu, Arg at position 38 is substituted with Lys, Gln at position 39 is substituted with Leu, Met at position 48 is substituted with Ile, Arg at position 67 is substituted with Lys, Val at position 68 is substituted with Ala, Ile at position 70 is substituted with Leu, Ala at position 72 is substituted with Val, Thr at position 74 is substituted with Lys and Ala at position 97 is substituted with Thr in the amino acid sequence represented by SEQ ID NO:12;

(5) an amino acid sequence in which Val at position 20 is substituted with Leu, Arg at position 38 is substituted with Lys, Gln at position 39 is substituted with Leu, Leu at position 45 is substituted with Phe, Arg at position 67 is substituted with Lys, Val at position 68 is substituted with Ala, Ile at position 70 is substituted with Leu, Ala at position 72 is substituted with Val, Thr at position 74 is substituted with Lys and Ala at position 97 is substituted with Thr in the amino acid sequence represented by SEQ ID NO:12;

(6) an amino acid sequence in which Val at position 20 is substituted with Leu, Arg at position 38 is substituted with Lys, Gln at position 39 is substituted with Leu, Leu at position 45 is substituted with Phe, Met at position 48 is substituted with Ile, Val at position 68 is substituted with Ala, Ile at position 70 is substituted with Leu, Ala at position 72 is substituted with Val, Thr at position 74 is substituted with Lys and Ala at position 97 is substituted with Thr in the amino acid sequence represented by SEQ ID NO:12;

(7) an amino acid sequence in which Val at position 20 is substituted with Leu, Arg at position 38 is substituted with Lys, Gln at position 39 is substituted with Leu, Leu at position 45 is substituted with Phe, Met at position 48 is substituted with Ile, Arg at position 67 is substituted with Lys, Ile at position 70 is substituted with Leu, Ala at position 72 is substituted with Val, Thr at position 74 is substituted with Lys and Ala at position 97 is substituted with Thr in the amino acid sequence represented by SEQ ID NO:12;

(8) an amino acid sequence in which Val at position 20 is substituted with Leu, Arg at position 38 is substituted with Lys, Gln at position 39 is substituted with Leu, Leu at position 45 is substituted with Phe, Met at position 48 is substituted with Ile, Arg at position 67 is substituted with Lys, Val at position 68 is substituted with Ala, Ala at position 72 is substituted with Val, Thr at position 74 is substituted with Lys and Ala at position 97 is substituted with Thr in the amino acid sequence represented by SEQ ID NO:12;

(9) an amino acid sequence in which Val at position 20 is substituted with Leu, Arg at position 38 is substituted with Lys, Gln at position 39 is substituted with Leu, Leu at position 45 is substituted with Phe, Met at position 48 is substituted with Ile, Arg at position 67 is substituted with Lys, Val at position 68 is substituted with Ala, Ile at position 70 is substituted with Leu, Thr at position 74 is substituted with Lys and Ala at position 97 is substituted with Thr in the amino acid sequence represented by SEQ ID NO:12;

(10) an amino acid sequence in which Val at position 20 is substituted with Leu, Arg at position 38 is substituted with Lys, Gln at position 39 is substituted with Leu, Leu at position 45 is substituted with Phe, Met at position 48 is substituted with Ile, Arg at position 67 is substituted with Lys, Val at position 68 is substituted with Ala, Ile at position 70 is substituted with Leu, Ala at position 72 is substituted with Val and Ala at position 97 is substituted with Thr in the amino acid sequence represented by SEQ ID NO:12;

(11) an amino acid sequence in which Val at position 20 is substituted with Leu, Arg at position 38 is substituted with Lys, Gln at position 39 is substituted with Leu, Leu at position 45 is substituted with Phe, Met at position 48 is substituted with Ile, Arg at position 67 is substituted with Lys, Val at position 68 is substituted with Ala, Ile at position 70 is substituted with Leu, Ala at position 72 is substituted with Val and Thr at position 74 is substituted with Lys in the amino acid sequence represented by SEQ ID NO: 12;

(12) an amino acid sequence in which Lys at position 12 is substituted with Val, Gln at position 39 is substituted with Leu, Leu at position 45 is substituted with Phe, Met at position 48 is substituted with Ile, Arg at position 67 is substituted with Lys, Val at position 68 is substituted with Ala, Ile at position 70 is substituted with Leu, Ala at position 72 is substituted with Val, Thr at position 74 is substituted with Lys and Ala at position 97 is substituted with Thr in the amino acid sequence represented by SEQ ID NO:12;

(13) an amino acid sequence in which Lys at position 12 is substituted with Val, Arg at position 38 is substituted with Lys, Leu at position 45 is substituted with Phe, Met at position 48 is substituted with Ile, Arg at position 67 is substituted with Lys, Val at position 68 is substituted with Ala, Ile at position 70 is substituted with Leu, Ala at position 72 is substituted with Val, Thr at position 74 is substituted With Lys and Ala at position 97 is substituted with Thr in the amino acid sequence represented by SEQ ID NO:12;

(14) an amino acid sequence in which Lys at position 12 is substituted with Val, Arg at position 38 is substituted with Lys, Gln at position 39 is substituted with Leu, Met at position 48 is substituted with Ile, Arg at position 67 is substituted with Lys, Val at position 68 is substituted with Ala, Ile at position 70 is substituted with Leu, Ala at position 72 is substituted with Val, Thr at position 74 is substituted with Lys and Ala at position 97 is substituted with Thr in the amino acid sequence represented by SEQ ID NO:12;

(15) an amino acid sequence in which Lys at position 12 is substituted with Val, Arg at position 38 is substituted with Lys, Gln at position 39 is substituted with Leu, Leu at position 45 is substituted with Phe, Arg at position 67 is substituted with Lys, Val at position 68 is substituted with Ala, Ile at position 70 is substituted with Leu, Ala at position 72 is substituted with Val, Thr at position 74 is substituted with Lys and Ala at position 97 is substituted with Thr in the amino acid sequence represented by SEQ ID NO:12;

(16) an amino acid sequence in which Lys at position 12 is substituted with Val, Arg at position 38 is substituted with Lys, Gln at position 39 is substituted with Leu, Leu at position 45 is substituted with Phe, Met at position 48 is substituted with Ile, Val at position 68 is substituted with Ala, Ile at position 70 is substituted with Leu, Ala at position 72 is substituted with Val, Thr at position 74 is substituted with Lys and Ala at position 97 is substituted with Thr in the amino acid sequence represented by SEQ ID NO:12;

(17) an amino acid sequence in which Lys at position 12 is substituted with Val, Arg at position 38 is substituted with Lys, Gln at position 39 is substituted with Leu, Leu at position 45 is substituted with Phe, Met at position 48 is substituted with Ile, Arg at position 67 is substituted with Lys, Ile at position 70 is substituted with Leu, Ala at position 72 is substituted with Val, Thr at position 74 is substituted with Lys and Ala at position 97 is substituted with Thr in the amino acid sequence represented by SEQ ID NO:12;

(18) an amino acid sequence in which Lys at position 12 is substituted with Val, Arg at position 38 is substituted with Lys, Gln at position 39 is substituted with Leu, Leu at position 45 is substituted with Phe, Met at position 48 is substituted with Ile, Arg at position 67 is substituted with Lys, Val at position 68 is substituted with Ala, Ala at position 72 is substituted with Val, Thr at position 74 is substituted with Lys and Ala at position 97 is substituted with Thr in the amino acid sequence represented by SEQ ID NO:12;

(19) an amino acid sequence in which Lys at position 12 is substituted with Val, Arg at position 38 is substituted with Lys, Gln at position 39 is substituted with Leu, Leu at position 45 is substituted with Phe, Met at position 48 is substituted with Ile, Arg at position 67 is substituted with Lys, Val at position 68 is substituted with Ala, Ile at position 70 is substituted with Leu, Thr at position 74 is substituted with Lys and Ala at position 97 is substituted with Thr in the amino acid sequence represented by SEQ ID NO:12;

(20) an amino acid sequence in which Lys at position 12 is substituted with Val, Arg at position 38 is substituted with Lys, Gln at position 39 is substituted with Leu, Leu at position 45 is substituted with Phe, Met at position 48 is substituted with Ile, Arg at position 67 is substituted with Lys, Val at position 68 is substituted with Ala, Ile at position 70 is substituted with Leu, Ala at position 72 is substituted with Val and Ala at position 97 is substituted with Thr in the amino acid sequence represented by SEQ ID NO:12;

(21) an amino acid sequence in which Lys at position 12 is substituted with Val, Arg at position 38 is substituted with Lys, Gln at position 39 is substituted with Leu, Leu at position 45 is substituted with Phe, Met at position 48 is substituted with Ile, Arg at position 67 is substituted with Lys, Val at position 68 is substituted with Ala, Ile at position 70 is substituted with Leu, Ala at position 72 is substituted with Val and Thr at position 74 is substituted with Lys in the amino acid sequence represented by SEQ ID NO:12;

(22) an amino acid sequence in which Lys at position 12 is substituted with Val, Val at position 20 is substituted with Leu, Leu at position 45 is substituted with Phe, Met at position 48 is substituted with Ile, Arg at position 67 is substituted with Lys, Val at position 68 is substituted with Ala, Ile at position 70 is substituted with Leu, Ala at position 72 is substituted with Val, Thr at position 74 is substituted with Lys and Ala at position 97 is substituted with Thr in the amino acid sequence represented by SEQ ID NO:12;

(23) an amino acid sequence in which Lys at position 12 is substituted with Val, Val at position 20 is substituted with Leu, Gln at position 39 is substituted with Leu, Met at position 48 is substituted with Ile, Arg at position 67 is substituted with Lys, Val at position 68 is substituted with Ala, Ile at position 70 is substituted with Leu, Ala at position 72 is substituted with Val, Thr at position 74 is substituted with Lys and Ala at position 97 is substituted with Thr in the amino acid sequence represented by SEQ ID NO:12;

(24) an amino acid sequence in which Lys at position 12 is substituted with Val, Val at position 20 is substituted with Leu, Gln at position 39 is substituted with Leu, Leu at position 45 is substituted with Phe, Arg at position 67 is substituted with Lys, Val at position 68 is substituted with Ala, Ile at position 70 is substituted with Leu, Ala at position 72 is substituted with Val, Thr at position 74 is substituted with Lys and Ala at position 97 is substituted with Thr in the amino acid sequence represented by SEQ ID NO:12;

(25) an amino acid sequence in which Lys at position 12 is substituted with Val, Val at position 20 is substituted with Leu, Gln at position 39 is substituted with Leu, Leu at position 45 is substituted with Phe, Met at position 48 is substituted with Ile, Val at position 68 is substituted with Ala, Ile at position 70 is substituted with Leu, Ala at position 72 is substituted with Val, Thr at position 74 is substituted with Lys and Ala at position 97 is substituted with Thr in the amino acid sequence represented by SEQ ID NO:12;

(26) an amino acid sequence in which Lys at position 12 is substituted with Val, Val at position 20 is substituted with Leu, Gln at position 39 is substituted with Leu, Leu at position 45 is substituted with Phe, Met at position 48 is substituted with Ile, Arg at position 67 is substituted with Lys, Ile at position 70 is substituted with Leu, Ala at position 72 is substituted with Val, Thr at position 74 is substituted with Lys and Ala at position 97 is substituted with Thr in the amino acid sequence represented by SEQ ID NO:12;

(27) an amino acid sequence in which Lys at position 12 is substituted with Val, Val at position 20 is substituted with Leu, Gln at position 39 is substituted with Leu, Leu at position 45 is substituted with Phe, Met at position 48 is substituted with Ile, Arg at position 67 is substituted with Lys, Val at position 68 is substituted with Ala, Ala at position 72 is substituted with Val, Thr at position 74 is substituted with Lys and Ala at position 97 is substituted with Thr in the amino acid sequence represented by SEQ ID NO:12;
(28) an amino acid sequence in which Lys at position 12 is substituted with Val, Val at position 20 is substituted with Leu, Gln at position 39 is substituted with Leu, Leu at position 45 is substituted with Phe, Met at position 48 is substituted with Ile, Arg at position 67 is substituted with Lys, Val at position 68 is substituted with Ala, Ile at position 70 is substituted with Leu, Thr at position 74 is substituted with Lys and Ala at position 97 is substituted with Thr in the amino acid sequence represented by SEQ ID NO:12;
(29) an amino acid sequence in which Lys at position 12 is substituted with Val, Val at position 20 is substituted with Leu, Gln at position 39 is substituted with Leu, Leu at position 45 is substituted with Phe, Met at position 48 is substituted with Ile, Arg at position 67 is substituted with Lys, Val at position 68 is substituted with Ala, Ile at position 70 is substituted with Leu, Ala at position 72 is substituted with Val and Ala at position 97 is substituted with Thr in the amino acid sequence represented by SEQ ID NO:12;
(30) an amino acid sequence in which Lys at position 12 is substituted with Val, Val at position 20 is substituted with Leu, Gln at position 39 is substituted with Leu, Leu at position 45 is substituted with Phe, Met at position 48 is substituted with Ile, Arg at position 67 is substituted with Lys, Val at position 68 is substituted with Ala, Ile at position 70 is substituted with Leu, Ala at position 72 is substituted with Val and Thr at position 74 is substituted with Lys in the amino acid sequence represented by SEQ ID NO:12;
(31) an amino acid sequence in which Lys at position 12 is substituted with Val, Val at position 20 is substituted with Leu, Arg at position 38 is substituted with Lys, Met at position 48 is substituted with Ile, Arg at position 67 is substituted with Lys, Val at position 68 is substituted with Ala, Ile at position 70 is substituted with Leu, Ala at position 72 is substituted with Val, Thr at position 74 is substituted with Lys and Ala at position 97 is substituted with Thr in the amino acid sequence represented by SEQ ID NO:12;
(32) an amino acid sequence in which Lys at position 12 is substituted with Val, Val at position 20 is substituted with Leu, Arg at position 38 is substituted with Lys, Leu at position 45 is substituted with Phe, Arg at position 67 is substituted with Lys, Val at position 68 is substituted with Ala, Ile at position 70 is substituted with Leu, Ala at position 72 is substituted with Val, Thr at position 74 is substituted with Lys and Ala at position 97 is substituted with Thr in the amino acid sequence represented by SEQ ID NO:12;
(33) an amino acid sequence in which Lys at position 12 is substituted with Val, Val at position 20 is substituted with Leu, Arg at position 38 is substituted with Lys, Leu at position 45 is substituted with Phe, Met at position 48 is substituted with Ile, Val at position 68 is substituted with Ala, Ile at position 70 is substituted with Leu, Ala at position 72 is substituted with Val, Thr at position 74 is substituted with Lys and Ala at position 97 is substituted with Thr in the amino acid sequence represented by SEQ ID NO:12;
(34) an amino acid sequence in which Lys at position 12 is substituted with Val, Val at position 20 is substituted with Leu, Arg at position 38 is substituted with Lys, Leu at position 45 is substituted with Phe, Met at position 48 is substituted with Ile, Arg at position 67 is substituted with Lys, Ile at position 70 is substituted with Leu, Ala at position 72 is substituted with Val, Thr at position 74 is substituted with Lys and Ala at position 97 is substituted with Thr in the amino acid sequence represented by SEQ ID NO:12;
(35) an amino acid sequence in which Lys at position 12 is substituted with Val, Val at position 20 is substituted with Leu, Arg at position 38 is substituted with Lys, Leu at position 45 is substituted with Phe, Met at position 48 is substituted with Ile, Arg at position 67 is substituted with Lys, Val at position 68 is substituted with Ala, Ala at position 72 is substituted with Val, Thr at position 74 is substituted with Lys and Ala at position 97 is substituted with Thr in the amino acid sequence represented by SEQ ID NO:12;
(36) an amino acid sequence in which Lys at position 12 is substituted with Val, Val at position 20 is substituted with Leu, Arg at position 38 is substituted with Lys, Leu at position 45 is substituted with Phe, Met at position 48 is substituted with Ile, Arg at position 67 is substituted with Lys, Val at position 68 is substituted with Ala, Ile at position 70 is substituted with Leu, Thr at position 74 is substituted with Lys and Ala at position 97 is substituted with Thr in the amino acid sequence represented by SEQ ID NO:12;
(37) an amino acid sequence in which Lys at position 12 is substituted with Val, Val at position 20 is substituted with Leu, Arg at position 38 is substituted with Lys, Leu at position 45 is substituted with Phe, Met at position 48 is substituted with Ile, Arg at position 67 is substituted with Lys, Val at position 68 is substituted with Ala, Ile at position 70 is substituted with Leu, Ala at position 72 is substituted with Val and Ala at position 97 is substituted with Thr in the amino acid sequence represented by SEQ ID NO:12;
(38) an amino acid sequence in which Lys at position 12 is substituted with Val, Val at position 20 is substituted with Leu, Arg at position 38 is substituted with Lys, Leu at position 45 is substituted with Phe, Met at position 48 is substituted with Ile, Arg at position 67 is substituted with Lys, Val at position 68 is substituted with Ala, Ile at position 70 is substituted with Leu, Ala at position 72 is substituted with Val and Thr at position 74 is substituted with Lys in the amino acid sequence represented by SEQ ID NO:12;
(39) an amino acid sequence in which Lys at position 12 is substituted with Val, Val at position 20 is substituted with Leu, Arg at position 38 is substituted with Lys, Gln at position 39 is substituted with Leu, Arg at position 67 is substituted with Lys, Val at position 68 is substituted with Ala, Ile at position 70 is substituted with Leu, Ala at position 72 is substituted with Val, Thr at position 74 is substituted with Lys and Ala at position 97 is substituted with Thr in the amino acid sequence represented by SEQ ID NO:12;
(40) an amino acid sequence in which Lys at position 12 is substituted with Val, Val at position 20 is substituted with Leu, Arg at position 38 is substituted with Lys, Gln at position 39 is substituted with Leu, Met at position 48 is substituted with Ile, Val at position 68 is substituted with Ala, Ile at position 70 is substituted with Leu, Ala at position 72 is substituted with Val, Thr at position 74 is substituted with Lys and Ala at position 97 is substituted with Thr in the amino acid sequence represented by SEQ ID NO:12;
(41) an amino acid sequence in which Lys at position 12 is substituted with Val, Val at position 20 is substituted with Leu, Arg at position 38 is substituted with Lys, Gln at position 39 is substituted with Leu, Met at position 48 is substituted with Ile, Arg at position 67 is substituted with Lys, Ile at position 70 is substituted with Leu, Ala at position 72 is substituted with Val, Thr at position 74 is substituted with Lys and Ala at position 97 is substituted with Thr in the amino acid sequence represented by SEQ ID NO:12;
(42) an amino acid sequence in which Lys at position 12 is substituted with Val, Val at position 20 is substituted with Leu, Arg at position 38 is substituted with Lys, Gln at position 39 is substituted with Leu, Met at position 48 is substituted with Ile, Arg at position 67 is substituted with Lys, Val at position 68 is substituted with Ala, Ala at position 72 is substituted with Val, Thr at position 74 is substituted with Lys and Ala at position 97 is substituted with Thr in the amino acid sequence represented by SEQ ID NO:12;

(43) an amino acid sequence in which Lys at position 12 is substituted with Val, Val at position 20 is substituted with Leu, Arg at position 38 is substituted with Lys, Gln at position 39 is substituted with Leu, Met at position 48 is substituted with Ile, Arg at position 67 is substituted with Lys, Val at position 68 is substituted with Ala, Ile at position 70 is substituted with Leu, Thr at position 74 is substituted with Lys and Ala at position 97 is substituted with Thr in the amino acid sequence represented by SEQ ID NO:12;

(44) an amino acid sequence in which Lys at position 12 is substituted with Val, Val at position 20 is substituted with Leu, Arg at position 38 is substituted with Lys, Gln at position 39 is substituted with Leu, Met at position 48 is substituted with Ile, Arg at position 67 is substituted with Lys, Val at position 68 is substituted with Ala, Ile at position 70 is substituted with Leu, Ala at position 72 is substituted with Val and Ala at position 97 is substituted with Thr in the amino acid sequence represented by SEQ ID NO:12;

(45) an amino acid sequence in which Lys at position 12 is substituted with Val, Val at position 20 is substituted with Leu, Arg at position 38 is substituted with Lys, Gln at position 39 is substituted with Leu, Met at position 48 is substituted with Ile, Arg at position 67 is substituted with Lys, Val at position 68 is substituted with Ala, Ile at position 70 is substituted with Leu, Ala at position 72 is substituted with Val and Thr at position 74 is substituted with Lys in the amino acid sequence represented by SEQ ID NO:12;

(46) an amino acid sequence in which Lys at position 12 is substituted with Val, Val at position 20 is substituted with Leu, Arg at position 38 is substituted with Lys, Gln at position 39 is substituted with Leu, Leu at position 45 is substituted with Phe, Val at position 68 is substituted with Ala, Ile at position 70 is substituted with Leu, Ala at position 72 is substituted with Val, Thr at position 74 is substituted with Lys and Ala at position 97 is substituted with Thr in the amino acid sequence represented by SEQ ID NO:12;

(47) an amino acid sequence in which Lys at position 12 is substituted with Val, Val at position 20 is substituted with Leu, Arg at position 38 is substituted with Lys, Gln at position 39 is substituted with Leu, Leu at position 45 is substituted with Phe, Arg at position 67 is substituted with Lys, Ile at position 70 is substituted with Leu, Ala at position 72 is substituted with Val, Thr at position 74 is substituted with Lys and Ala at position 97 is substituted with Thr in the amino acid sequence represented by SEQ ID NO:12;

(48) an amino acid sequence in which Lys at position 12 is substituted with Val, Val at position 20 is substituted with Leu, Arg at position 38 is substituted with Lys, Gln at position 39 is substituted with Leu, Leu at position 45 is substituted with Phe, Arg at position 67 is substituted with Lys, Val at position 68 is substituted with Ala, Ala at position 72 is substituted with Val, Thr at position 74 is substituted with Lys and Ala at position 97 is substituted with Thr in the amino acid sequence represented by SEQ ID NO:12;

(49) an amino acid sequence in which Lys at position 12 is substituted with Val, Val at position 20 is substituted with Leu, Arg at position 38 is substituted with Lys, Gln at position 39 is substituted with Leu, Leu at position 45 is substituted with Phe, Arg at position 67 is substituted with Lys, Val at position 68 is substituted with Ala, Ile at position 70 is substituted with Leu, Thr at position 74 is substituted with Lys and Ala at position 97 is substituted with Thr in the amino acid sequence represented by SEQ ID NO:12;

(50) an amino acid sequence in which Lys at position 12 is substituted with Val, Val at position 20 is substituted with Leu, Arg at position 38 is substituted with Lys, Gln at position 39 is substituted with Leu, Leu at position 45 is substituted with Phe, Arg at position 67 is substituted with Lys, Val at position 68 is substituted with Ala, Ile at position 70 is substituted with Leu, Ala at position 72 is substituted with Val and Ala at position 97 is substituted with Thr in the amino acid sequence represented by SEQ ID NO:12;

(51) an amino acid sequence in which Lys at position 12 is substituted with Val, Val at position 20 is substituted with Leu, Arg at position 38 is substituted with Lys, Gln at position 39 is substituted with Leu, Leu at position 45 is substituted with Phe, Arg at position 67 is substituted with Lys, Val at position 68 is substituted with Ala, Ile at position 70 is substituted with Leu, Ala at position 72 is substituted with Val and Thr at position 74 is substituted with Lys in the amino acid sequence represented by SEQ ID NO:12;

(52) an amino acid sequence in which Lys at position 12 is substituted with Val, Val at position 20 is substituted with Leu, Arg at position 38 is substituted with Lys, Gln at position 39 is substituted with Leu, Leu at position 45 is substituted with Phe, Met at position 48 is substituted with Ile, Ile at position 70 is substituted with Leu, Ala at position 72 is substituted with Val, Thr at position 74 is substituted with Lys and Ala at position 97 is substituted with Thr in the amino acid sequence represented by SEQ ID NO:12;

(53) an amino acid sequence in which Lys at position 12 is substituted with Val, Val at position 20 is substituted with Leu, Arg at position 38 is substituted with Lys, Gln at position 39 is substituted with Leu, Leu at position 45 is substituted with Phe, Met at position 48 is substituted with Ile, Val at position 68 is substituted with Ala, Ala at position 72 is substituted with Val, Thr at position 74 is substituted with Lys and Ala at position 97 is substituted with Thr in the amino acid sequence represented by SEQ ID NO:12;

(54) an amino acid sequence in which Lys at position 12 is substituted with Val, Val at position 20 is substituted with Leu, Arg at position 38 is substituted with Lys, Gln at position 39 is substituted with Leu, Leu at position 45 is substituted with Phe, Met at position 48 is substituted with Ile, Val at position 68 is substituted with Ala, Ile at position 70 is substituted with Leu, Thr at position 74 is substituted with Lys and Ala at position 97 is substituted with Thr in the amino acid sequence represented by SEQ ID NO:12;

(55) an amino acid sequence in which Lys at position 12 is substituted with Val, Val at position 20 is substituted with Leu, Arg at position 38 is substituted with Lys, Gln at position 39 is substituted with Leu, Leu at position 45 is substituted with Phe, Met at position 48 is substituted with Ile, Val at position 68 is substituted with Ala, Ile at position 70 is substituted with Leu, Ala at position 72 is substituted with Val and Ala at position 97 is substituted with Thr in the amino acid sequence represented by SEQ ID NO:12;

(56) an amino acid sequence in which Lys at position 12 is substituted with Val, Val at position 20 is substituted with Leu, Arg at position 38 is substituted with Lys, Gln at position 39 is substituted with Leu, Leu at position 45 is substituted with Phe, Met at position 48 is substituted with Ile, Val at position 68 is substituted with Ala, Ile at position 70 is substituted with Leu, Ala at position 72 is substituted with Val and Thr at position 74 is substituted with Lys in the amino acid sequence represented by SEQ ID NO:12;

(57) an amino acid sequence in which Lys at position 12 is substituted with Val, Val at position 20 is substituted with Leu, Arg at position 38 is substituted with Lys, Gln at position 39 is substituted with Leu, Leu at position 45 is substituted with Phe, Met at position 48 is substituted with Ile, Arg at position 67 is substituted with Lys, Ala at position 72 is substituted with Val, Thr at position 74 is substituted with Lys and Ala at position 97 is substituted with Thr in the amino acid sequence represented by SEQ ID NO:12;

(58) an amino acid sequence in which Lys at position 12 is substituted with Val, Val at position 20 is substituted with Leu, Arg at position 38 is substituted with Lys, Gln at position 39 is substituted with Leu, Leu at position 45 is substituted with Phe, Met at position 48 is substituted with Ile, Arg at position 67 is substituted with Lys, Ile at position 70 is substituted with Leu, Thr at position 74 is substituted with Lys and Ala at position 97 is substituted with Thr in the amino acid sequence represented by SEQ ID NO:12;

(59) an amino acid sequence in which Lys at position 12 is substituted with Val, Val at position 20 is substituted with Leu, Arg at position 38 is substituted with Lys, Gln at position 39 is substituted with Leu, Leu at position 45 is substituted with Phe, Met at position 48 is substituted with Ile, Arg at position 67 is substituted with Lys, Ile at position 70 is substituted with Leu, Ala at position 72 is substituted with Val and Ala at position 97 is substituted with Thr in the amino acid sequence represented by SEQ ID NO:12;

(60) an amino acid sequence in which Lys at position 12 is substituted with Val, Val at position 20 is substituted with Leu, Arg at position 38 is substituted with Lys, Gln at position 39 is substituted with Leu, Leu at position 45 is substituted with Phe, Met at position 48 is substituted with Ile, Arg at position 67 is substituted with Lys, Ile at position 70 is substituted with Leu, Ala at position 72 is substituted with Val and Thr at position 74 is substituted with Lys in the amino acid sequence represented by SEQ ID NO:12;

(61) an amino acid sequence in which Lys at position 12 is substituted with Val, Val at position 20 is substituted with Leu, Arg at position 38 is substituted with Lys, Gln at position 39 is substituted with Leu, Leu at position 45 is substituted with Phe, Met at position 48 is substituted with Ile, Arg at position 67 is substituted with Lys, Val at position 68 is substituted with Ala, Thr at position 74 is substituted with Lys and Ala at position 97 is substituted with Thr in the amino acid sequence represented by SEQ ID NO:12;

(62) an amino acid sequence in which Lys at position 12 is substituted with Val, Val at position 20 is substituted with Leu, Arg at position 38 is substituted with Lys, Gln at position 39 is substituted with Leu, Leu at position 45 is substituted with Phe, Met at position 48 is substituted with Ile, Arg at position 67 is substituted with Lys, Val at position 68 is substituted with Ala, Ala at position 72 is substituted with Val and Ala at position 97 is substituted with Thr in the amino acid sequence represented by SEQ ID NO:12;

(63) an amino acid sequence in which Lys at position 12 is substituted with Val, Val at position 20 is substituted with Leu, Arg at position 38 is substituted with Lys, Gln at position 39 is substituted with Leu, Leu at position 45 is substituted with Phe, Met at position 48 is substituted with Ile, Arg at position 67 is substituted with Lys, Val at position 68 is substituted with Ala, Ala at position 72 is substituted with Val and Thr at position 74 is substituted with Lys in the amino acid sequence represented by SEQ ID NO:12;

(64) an amino acid sequence in which Lys at position 12 is substituted with Val, Val at position 20 is substituted with Leu, Arg at position 38 is substituted with Lys, Gln at position 39 is substituted with Leu, Leu at position 45 is substituted with Phe, Met at position 48 is substituted with Ile, Arg at position 67 is substituted with Lys, Val at position 68 is substituted with Ala, Ile at position 70 is substituted with Leu and Ala at position 97 is substituted with Thr in the amino acid sequence represented by SEQ ID NO:12;

(65) an amino acid sequence in which Lys at position 12 is substituted with Val, Val at position 20 is substituted with Leu, Arg at position 38 is substituted with Lys, Gln at position 39 is substituted with Leu, Leu at position 45 is substituted with Phe, Met at position 48 is substituted with Ile, Arg at position 67 is substituted with Lys, Val at position 68 is substituted with Ala, Ile at position 70 is substituted with Leu and Thr at position 74 is substituted with Lys in the amino acid sequence represented by SEQ ID NO:12;

(66) an amino acid sequence in which Lys at position 12 is substituted with Val, Val at position 20 is substituted with Leu, Arg at position 38 is substituted with Lys, Gln at position 39 is substituted with Leu, Leu at position 45 is substituted with Phe, Met at position 48 is substituted with Ile, Arg at position 67 is substituted with Lys, Val at position 68 is substituted with Ala, Ile at position 70 is substituted with Leu and Ala at position 72 is substituted with Val in the amino acid sequence represented by SEQ ID NO:12.

Specific examples of the amino acid sequence of VH in which nine substitutions are introduced include the following (1) to (10) amino acid sequences:

(1) an amino acid sequence in which Arg at position 38 is substituted with Lys, Gln at position 39 is substituted with Leu, Leu at position 45 is substituted with Phe, Met at position 48 is substituted with Ile, Arg at position 67 is substituted with Lys, Val at position 68 is substituted with Ala, Ala at position 72 is substituted with Val, Thr at position 74 is substituted with Lys and Ala at position 97 is substituted with Thr in the amino acid sequence represented by SEQ ID NO:12;

(2) an amino acid sequence in which Lys at position 12 is substituted with Val, Gln at position 39 is substituted with Leu, Leu at position 45 is substituted with Phe, Met at position 48 is substituted with Ile, Arg at position 67 is substituted with Lys, Val at position 68 is substituted with Ala, Ala at position 72 is substituted with Val, Thr at position 74 is substituted with Lys and Ala at position 97 is substituted with Thr in the amino acid sequence represented by SEQ ID NO:12;

(3) an amino acid sequence in which Lys at position 12 is substituted with Val, Arg at position 38 is substituted with Lys, Leu at position 45 is substituted with Phe, Met at position 48 is substituted with Ile, Arg at position 67 is substituted with Lys, Val at position 68 is substituted with Ala, Ala at position 72 is substituted with Val, Thr at position 74 is substituted with Lys and Ala at position 97 is substituted with Thr in the amino acid sequence represented by SEQ ID NO:12;

(4) an amino acid sequence in which Lys at position 12 is substituted with Val, Arg at position 38 is substituted with Lys, Gln at position 39 is substituted with Leu, Met at position 48 is substituted with Ile, Arg at position 67 is substituted with Lys, Val at position 68 is substituted with Ala, Ala at position 72 is substituted with Val, Thr at position 74 is substituted with Lys and Ala at position 97 is substituted with Thr in the amino acid sequence represented by SEQ ID NO:12;

(5) an amino acid sequence in which Lys at position 12 is substituted with Val, Arg at position 38 is substituted with Lys, Gln at position 39 is substituted with Leu, Leu at position 45 is substituted with Phe, Arg at position 67 is substituted with Lys, Val at position 68 is substituted with Ala, Ala at position 72 is substituted with Val, Thr at position 74 is substituted with Lys and Ala at position 97 is substituted with Thr in the amino acid sequence represented by SEQ ID NO:12;
(6) an amino acid sequence in which Lys at position 12 is substituted with Val, Arg at position 38 is substituted with Lys, Gln at position 39 is substituted with Leu, Leu at position 45 is substituted with Phe, Met at position 48 is substituted with Ile, Val at position 68 is substituted with Ala, Ala at position 72 is substituted with Val, Thr at position 74 is substituted with Lys and Ala at position 97 is substituted with Thr in the amino acid sequence represented by SEQ ID NO:12;
(7) an amino acid sequence in which Lys at position 12 is substituted with Val, Arg at position 38 is substituted with Lys, Gln at position 39 is substituted with Leu, Leu at position 45 is substituted with Phe, Met at position 48 is substituted with Ile, Arg at position 67 is substituted with Lys, Ala at position 72 is substituted with Val, Thr at position 74 is substituted with Lys and Ala at position 97 is substituted with Thr in the amino acid sequence represented by SEQ ID NO:12;
(8) an amino acid sequence in which Lys at position 12 is substituted with Val, Arg at position 38 is substituted with Lys, Gln at position 39 is substituted with Leu, Leu position 45 is substituted with Phe, Met at position 48 is substituted with Ile, Arg at position 67 is substituted with Lys, Val at position 68 is substituted with Ala, Thr at position 74 is substituted with Lys and Ala at position 97 is substituted with Thr in the amino acid sequence represented by SEQ ID NO:12;
(9) an amino acid sequence in which Lys at position 12 is substituted with Val, Arg at position 38 is substituted with Lys, Gln at position 39 is substituted with Leu, Leu at position 45 is substituted with Phe, Met at position 48 is substituted with Ile, Arg at position 67 is substituted with Lys, Val at position 68 is substituted with Ala, Ala at position 72 is substituted with Val and Ala at position 97 is substituted with Thr in the amino acid sequence represented by SEQ ID NO:12;
(10) an amino acid sequence in which Lys at position 12 is substituted with Val, Arg at position 38 is substituted with Lys, Gln at position 39 is substituted with Leu, Leu at position 45 is substituted with Phe, Met at position 48 is substituted with Ile, Arg at position 67 is substituted with Lys, Val at position 68 is substituted with Ala, Ala at position 72 is substituted with Val and Thr at position 74 is substituted with Lys in the amino acid sequence represented by SEQ ID NO:12.

Specific examples of the amino acid sequence of VH in which eight substitutions are introduced include the following (1) to (47) amino acid sequences:
(1) an amino acid sequence in which Gln at position 39 is substituted with Leu, Leu at position 45 is substituted with Phe, Met at position 48 is substituted with Ile, Arg at position 67 is substituted with Lys, Val at position 68 is substituted with Ala, Ala at position 72 is substituted with Val, Thr at position 74 is substituted with Lys and Ala at position 97 is substituted with Thr in the amino acid sequence represented by SEQ ID NO:12;
(2) an amino acid sequence in which Arg at position 38 is substituted with Lys, Leu at position 45 is substituted with Phe, Met at position 48 is substituted with Ile, Arg at position 67 is substituted with Lys, Val at position 68 is substituted with Ala, Ala at position 72 is substituted with Val, Thr at position 74 is substituted with Lys and Ala at position 97 is substituted with Thr in the amino acid sequence represented by SEQ ID NO:12;
(3) an amino acid sequence in which Arg at position 38 is substituted with Lys, Gln at position 39 is substituted with Leu, Met at position 48 is substituted with Ile, Arg at position 67 is substituted with Lys, Val at position 68 is substituted with Ala, Ala at position 72 is substituted with Val, Thr at position 74 is substituted with Lys and Ala at position 97 is substituted with Thr in the amino acid sequence represented by SEQ ID NO:12;
(4) an amino acid sequence in which Arg at position 38 is substituted with Lys, Gln at position 39 is substituted with Leu, Leu at position 45 is substituted with Phe, Arg at position 67 is substituted with Lys, Val at position 68 is substituted with Ala, Ala at position 72 is substituted with Val, Thr at position 74 is substituted with Lys and Ala at position 97 is substituted with Thr in the amino acid sequence represented by SEQ ID NO:12;
(5) an amino acid sequence in which Arg at position 38 is substituted with Lys, Gln at position 39 is substituted with Leu, Leu at position 45 is substituted with Phe, Met at position 48 is substituted with Ile, Val at position 68 is substituted with Ala, Ala at position 72 is substituted with Val, Thr at position 74 is substituted with Lys and Ala at position 97 is substituted with Thr in the amino acid sequence represented by SEQ ID NO:12;
(6) an amino acid sequence in which Arg at position 38 is substituted with Lys, Gln at position 39 is substituted with Leu, Leu at position 45 is substituted with Phe, Met at position 48 is substituted with Ile, Arg at position 67 is substituted with Lys, Ala at position 72 is substituted with Val, Thr at position 74 is substituted with Lys and Ala at position 97 is substituted with Thr in the amino acid sequence represented by SEQ ID NO:12;
(7) an amino acid sequence in which Arg at position 38 is substituted with Lys, Gln at position 39 is substituted with Leu, Leu at position 45 is substituted with Phe, Met at position 48 is substituted with Ile, Arg at position 67 is substituted with Lys, Val at position 68 is substituted with Ala, Thr at position 74 is substituted with Lys and Ala at position 97 is substituted with Thr in the amino acid sequence represented by SEQ ID NO:12;
(8) an amino acid sequence in which Arg at position 38 is substituted with Lys, Gln at position 39 is substituted with Leu, Leu at position 45 is substituted with Phe, Met at position 48 is substituted with Ile, Arg at position 67 is substituted with Lys, Val at position 68 is substituted with Ala, Ala at position 72 is substituted with Val and Ala at position 97 is substituted with Thr in the amino acid sequence represented by SEQ ID NO:12;
(9) an amino acid sequence in which Arg at position 38 is substituted with Lys, Gln at position 39 is substituted with Leu, Leu at position 45 is substituted with Phe, Met at position 48 is substituted with Ile, Arg at position 67 is substituted with Lys, Val at position 68 is substituted with Ala, Ala at position 72 is substituted with Val and Thr at position 74 is substituted with Lys in the amino acid sequence represented by SEQ ID NO:12;
(10) an amino acid sequence in which Lys at position 12 is substituted with Val, Leu at position 45 is substituted with Phe, Met at position 48 is substituted with Ile, Arg at position 67 is substituted with Lys, Val at position 68 is substituted with Ala, Ala at position 72 is substituted with Val, Thr at position 74 is substituted with Lys and Ala at position 97 is substituted with Thr in the amino acid sequence represented by SEQ ID NO:12;
(11) an amino acid sequence in which Lys at position 12 is substituted with Val, Gln at position 39 is substituted with Leu, Met at position 48 is substituted with Ile, Arg at position 67 is substituted with Lys, Val at position 68 is substituted with Ala, Ala at position 72 is substituted with Val, Thr at position 74 is substituted with Lys and Ala at position 97 is substituted with Thr in the amino acid sequence represented by SEQ ID NO:12;

(12) an amino acid sequence in which Lys at position 12 is substituted with Val, Gln at position 39 is substituted with Leu, Leu at position 45 is substituted with Phe, Arg at position 67 is substituted with Lys, Val at position 68 is substituted with Ala, Ala at position 72 is substituted with Val, Thr at position 74 is substituted with Lys and Ala at position 97 is substituted with Thr in the amino acid sequence represented by SEQ ID NO:12;

(13) an amino acid sequence in which Lys at position 12 is substituted with Val, Gln at position 39 is substituted with Leu, Leu at position 45 is substituted with Phe, Met at position 48 is substituted with Ile, Val at position 68 is substituted with Ala, Ala at position 72 is substituted with Val, Thr at position 74 is substituted with Lys and Ala at position 97 is substituted with Thr in the amino acid sequence represented by SEQ ID NO:12;

(14) an amino acid sequence in which Lys at position 12 is substituted with Val, Gln at position 39 is substituted with Leu, Leu at position 45 is substituted with Phe, Met at position 48 is substituted with Ile, Arg at position 67 is substituted with Lys, Ala at position 72 is substituted with Val, Thr at position 74 is substituted with Lys and Ala at position 97 is substituted with Thr in the amino acid sequence represented by SEQ ID NO:12;

(15) an amino acid sequence in which Lys at position 12 is substituted with Val, Gln at position 39 is substituted with Leu, Leu at position 45 is substituted with Phe, Met at position 48 is substituted with Ile, Arg at position 67 is substituted with Lys, Val at position 68 is substituted with Ala, Thr at position 74 is substituted with Lys and Ala at position 97 is substituted with Thr in the amino acid sequence represented by SEQ ID NO:12;

(16) an amino acid sequence in which Lys at position 12 is substituted with Val, Gln at position 39 is substituted with Leu, Leu at position 45 is substituted with Phe, Met at position 48 is substituted with Ile, Arg at position 67 is substituted with Lys, Val at position 68 is substituted with Ala, Ala at position 72 is substituted with Val and Ala at position 97 is substituted with Thr in the amino acid sequence represented by SEQ ID NO:12;

(17) an amino acid sequence in which Lys at position 12 is substituted with Val, Gln at position 39 is substituted with Leu, Leu at position 45 is substituted with Phe, Met at position 48 is substituted with Ile, Arg at position 67 is substituted with Lys, Val at position 68 is substituted with Ala, Ala at position 72 is substituted with Val and Thr at position 74 is substituted with Lys in the amino acid sequence represented by SEQ ID NO:12;

(18) an amino acid sequence in which Lys at position 12 is substituted with Val, Arg at position 38 is substituted with Lys, Gln at position 39 is substituted with Leu, Leu at position 45 is substituted with Phe, Met at position 48 is substituted with Ile, Arg at position 67 is substituted with Lys, Val at position 68 is substituted with Ala, Ala at position 72 is substituted with Val, Thr at position 74 is substituted with Lys and Ala at position 97 is substituted with Thr in the amino acid sequence represented by SEQ ID NO:12;

(19) an amino acid sequence in which Lys at position 12 is substituted with Val, Arg at position 38 is substituted with Lys, Met at position 48 is substituted with Ile, Arg at position 67 is substituted with Lys, Val at position 68 is substituted with Ala, Ala at position 72 is substituted with Val, Thr at position 74 is substituted with Lys and Ala at position 97 is substituted with Thr in the amino acid sequence represented by SEQ ID NO:12;

(20) an amino acid sequence in which Lys at position 12 is substituted with Val, Arg at position 38 is substituted with Lys, Leu at position 45 is substituted with Phe, Arg at position 67 is substituted with Lys, Val at position 68 is substituted with Ala, Ala at position 72 is substituted with Val, Thr at position 74 is substituted with Lys and Ala at position 97 is substituted with Thr in the amino acid sequence represented by SEQ ID NO:12;

(21) an amino acid sequence in which Lys at position 12 is substituted with Val, Arg at position 38 is substituted with Lys, Leu at position 45 is substituted with Phe, Met at position 48 is substituted with Ile, Val at position 68 is substituted with Ala, Ala at position 72 is substituted with Val, Thr at position 74 is substituted with Lys and Ala at position 97 is substituted with Thr in the amino acid sequence represented by SEQ ID NO:12;

(22) an amino acid sequence in which Lys at position 12 is substituted with Val, Arg at position 38 is substituted with Lys, Leu at position 45 is substituted with Phe, Met at position 48 is substituted with Ile, Arg at position 67 is substituted with Lys, Ala at position 72 is substituted with Val, Thr at position 74 is substituted with Lys and Ala at position 97 is substituted with Thr in the amino acid sequence represented by SEQ ID NO:12;

(23) an amino acid sequence in which Lys at position 12 is substituted with Val, Arg at position 38 is substituted with Lys, Leu at position 45 is substituted with Phe, Met at position 48 is substituted with Ile, Arg at position 67 is substituted with Lys, Val at position 68 is substituted with Ala, Thr at position 74 is substituted with Lys and Ala at position 97 is substituted with Thr in the amino acid sequence represented by SEQ ID NO:12;

(24) an amino acid sequence in which Lys at position 12 is substituted with Val, Arg at position 38 is substituted with Lys, Leu at position 45 is substituted with Phe, Met at position 48 is substituted with Ile, Arg at position 67 is substituted with Lys, Val at position 68 is substituted with Ala, Ala at position 72 is substituted with Val and Ala at position 97 is substituted with Thr in the amino acid sequence represented by SEQ ID NO:12;

(25) an amino acid sequence in which Lys at position 12 is substituted with Val, Arg at position 38 is substituted with Lys, Leu at position 45 is substituted with Phe, Met at position 48 is substituted with Ile, Arg at position 67 is substituted with Lys, Val at position 68 is substituted with Ala, Ala at position 72 is substituted with Val and Thr at position 74 is substituted with Lys in the amino acid sequence represented by SEQ ID NO:12;

(26) an amino acid sequence in which Lys at position 12 is substituted with Val, Arg at position 38 is substituted with Lys, Gln at position 39 is substituted with Leu, Arg at position 67 is substituted with Lys, Val at position 68 is substituted with Ala, Ala at position 72 is substituted with Val, Thr at position 74 is substituted with Lys and Ala at position 97 is substituted with Thr in the amino acid sequence represented by SEQ ID NO:12;

(27) an amino acid sequence in which Lys at position 12 is substituted with Val, Arg at position 38 is substituted with Lys, Gln at position 39 is substituted with Leu, Arg at position 67 is substituted with Lys, Val at position 68 is substituted with Ala, Ala at position 72 is substituted with Val, Thr at position 74 is substituted with Lys and Ala at position 97 is substituted with Thr in the amino acid sequence represented by SEQ ID NO:12;

(28) an amino acid sequence in which Lys at position 12 is substituted with Val, Arg at position 38 is substituted with Lys, Gln at position 39 is substituted with Leu, Met at position 48 is substituted with Ile, Val at position 68 is substituted with Ala, Ala at position 72 is substituted with Val, Thr at position 74 is substituted with Lys and Ala at position 97 is substituted with Thr in the amino acid sequence represented by SEQ ID NO:12;

(29) an amino acid sequence in which Lys at position 12 is substituted with Val, Arg at position 38 is substituted with Lys, Gln at position 39 is substituted with Leu, Met at position 48 is substituted with Ile, Arg at position 67 is substituted with Lys, Ala at position 72 is substituted with Val, Thr at position 74 is substituted with Lys and Ala at position 97 is substituted with Thr in the amino acid sequence represented by SEQ ID NO:12;

(30) an amino acid sequence in which Lys at position 12 is substituted with Val, Arg at position 38 is substituted with Lys, Gln at position 39 is substituted with Leu, Met at position 48 is substituted with Ile, Arg at position 67 is substituted with Lys, Val at position 68 is substituted with Ala, Thr at position 74 is substituted with Lys and Ala at position 97 is substituted with Thr in the amino acid sequence represented by SEQ ID NO:12;

(31) an amino acid sequence in which Lys at position 12 is substituted with Val, Arg at position 38 is substituted with Lys, Gln at position 39 is substituted with Leu, Met at position 48 is substituted with Ile, Arg at position 67 is substituted with Lys, Val at position 68 is substituted with Ala, Ala at position 72 is substituted with Val and Ala at position 97 is substituted with Thr in the amino acid sequence represented by SEQ ID NO:12;

(32) an amino acid sequence in which Lys at position 12 is substituted with Val, Arg at position 38 is substituted with Lys, Gln at position 39 is substituted with Leu, Met at position 48 is substituted with Ile, Arg at position 67 is substituted with Lys, Val at position 68 is substituted with Ala, Ala at position 72 is substituted with Val and Thr at position 74 is substituted with Lys in the amino acid sequence represented by SEQ ID NO:12;

(33) an amino acid sequence in which Lys at position 12 is substituted with Val, Arg at position 38 is substituted with Lys, Gln at position 39 is substituted with Leu, Leu at position 45 is substituted with Phe, Val at position 68 is substituted with Ala, Ala at position 72 is substituted with Val, Thr at position 74 is substituted with Lys and Ala at position 97 is substituted with Thr in the amino acid sequence represented by SEQ ID NO:12;

(34) an amino acid sequence in which Lys at position 12 is substituted with Val, Arg at position 38 is substituted with Lys, Gln at position 39 is substituted with Leu, Leu at position 45 is substituted with Phe, Arg at position 67 is substituted with Lys, Ala at position 72 is substituted with Val, Thr at position 74 is substituted with Lys and Ala at position 97 is substituted with Thr in the amino acid sequence represented by SEQ ID NO:12;

(35) an amino acid sequence in which Lys at position 12 is substituted with Val, Arg at position 38 is substituted with Lys, Gln at position 39 is substituted with Leu, Leu at position 45 is substituted with Phe, Arg at position 67 is substituted with Lys, Val at position 68 is substituted with Ala, Thr at position 74 is substituted with Lys and Ala at position 97 is substituted with Thr in the amino acid sequence represented by SEQ ID NO:12;

(36) an amino acid sequence in which Lys at position 12 is substituted with Val, Arg at position 38 is substituted with Lys, Gln at position 39 is substituted with Leu, Leu at position 45 is substituted with Phe, Arg at position 67 is substituted with Lys, Val at position 68 is substituted with Ala, Ala at position 72 is substituted with Val and Ala at position 97 is substituted with Thr in the amino acid sequence represented by SEQ ID NO:12;

(37) an amino acid sequence in which Lys at position 12 is substituted with Val, Arg at position 38 is substituted with Lys, Gln at position 39 is substituted with Leu, Leu at position 45 is substituted with Phe, Arg at position 67 is substituted with Lys, Val at position 68 is substituted with Ala, Ala at position 72 is substituted with Val and Thr at position 74 is substituted with Lys in the amino acid sequence represented by SEQ ID NO:12;

(38) an amino acid sequence in which Lys at position 12 is substituted with Val, Arg at position 38 is substituted with Lys, Gln at position 39 is substituted with Leu, Leu at position 45 is substituted with Phe, Met at position 48 is substituted with Ile, Ala at position 72 is substituted with Val, Thr at position 74 is substituted with Lys and Ala at position 97 is substituted with Thr in the amino acid sequence represented by SEQ ID NO:12;

(39) an amino acid sequence in which Lys at position 12 is substituted with Val, Arg at position 38 is substituted with Lys, Gln at position 39 is substituted with Leu, Leu at position 45 is substituted with Phe, Met at position 48 is substituted with Ile, Val at position 68 is substituted with Ala, Thr at position 74 is substituted with Lys and Ala at position 97 is substituted with Thr in the amino acid sequence represented by SEQ ID NO:12;

(40) an amino acid sequence in which Lys at position 12 is substituted with Val, Arg at position 38 is substituted with Lys, Gln at position 39 is substituted with Leu, Leu at position 45 is substituted with Phe, Met at position 48 is substituted with Ile, Val at position 68 is substituted with Ala, Ala at position 72 is substituted with Val and Ala at position 97 is substituted with Thr in the amino acid sequence represented by SEQ ID NO:12;

(41) an amino acid sequence in which Lys at position 12 is substituted with Val, Arg at position 38 is substituted with Lys, Gln at position 39 is substituted with Leu, Leu at position 45 is substituted with Phe, Met at position 48 is substituted with Ile, Val at position 68 is substituted with Ala, Ala at position 72 is substituted with Val and Thr at position 74 is substituted with Lys in the amino acid sequence represented by SEQ ID NO:12;

(42) an amino acid sequence in which Lys at position 12 is substituted with Val, Arg at position 38 is substituted with Lys, Gln at position 39 is substituted with Leu, Leu at position 45 is substituted with Phe, Met at position 48 is substituted with Ile, Arg at position 67 is substituted with Lys, Thr at position 74 is substituted with Lys and Ala at position 97 is substituted with Thr in the amino acid sequence represented by SEQ ID NO:12;

(43) an amino acid sequence in which Lys at position 12 is substituted with Val, Arg at position 38 is substituted with Lys, Gln at position 39 is substituted with Leu, Leu at position 45 is substituted with Phe, Met at position 48 is substituted with Ile, Arg at position 67 is substituted with Lys, Ala at position 72 is substituted with Val and Ala at position 97 is substituted with Thr in the amino acid sequence represented by SEQ ID NO:12;

(44) an amino acid sequence in which Lys at position 12 is substituted with Val, Arg at position 38 is substituted with Lys, Gln at position 39 is substituted with Leu, Leu at position 45 is substituted with Phe, Met at position 48 is substituted with Ile, Arg at position 67 is substituted with Lys, Ala at position 72 is substituted with Val and Thr at position 74 is substituted with Lys in the amino acid sequence represented by SEQ ID NO:12;
(45) an amino acid sequence in which Lys at position 12 is substituted with Val, Arg at position 38 is substituted with Lys, Gln at position 39 is substituted with Leu, Leu at position 45 is substituted with Phe, Met at position 48 is substituted with Ile, Arg at position 67 is substituted with Lys, Val at position 68 is substituted with Ala and Ala at position 97 is substituted with Thr in the amino acid sequence represented by SEQ ID NO:12;
(46) an amino acid sequence in which Lys at position 12 is substituted with Val, Arg at position 38 is substituted with Lys, Gln at position 39 is substituted with Leu, Leu at position 45 is substituted with Phe, Met at position 48 is substituted with Ile, Arg at position 67 is substituted with Lys, Val at position 68 is substituted with Ala and Thr at position 74 is substituted with Lys in the amino acid sequence represented by SEQ ID NO:12;
(47) an amino acid sequence in which Lys at position 12 is substituted with Val, Arg at position 38 is substituted with Lys, Gln at position 39 is substituted with Leu, Leu at position 45 is substituted with Phe, Met at position 48 is substituted with Ile, Arg at position 67 is substituted with Lys, Val at position 68 is substituted with Ala and Ala at position 72 is substituted with Val in the amino acid sequence represented by SEQ ID NO:12.

Specific examples of the amino acid sequence of VH in which seven substitutions are introduced include the following (1) to (22) amino acid sequences:
(1) an amino acid sequence in which Lys at position 12 is substituted with Val, Val at position 20 is substituted with Leu, Gln at position 39 is substituted with Leu, Leu at position 45 is substituted with Phe, Met at position 48 is substituted with Ile, Arg at position 67 is substituted with Lys and Ala at position 97 is substituted with Thr in the amino acid sequence represented by SEQ ID NO:12;
(2) an amino acid sequence in which Lys at position 12 is substituted with Val, Arg at position 38 is substituted with Lys, Gln at position 39 is substituted with Leu, Leu at position 45 is substituted with Phe, Met at position 48 is substituted with Ile, Arg at position 67 is substituted with Lys and Ala at position 97 is substituted with Thr in the amino acid sequence represented by SEQ ID NO:12;
(3) an amino acid sequence in which Lys at position 12 is substituted with Val, Gln at position 39 is substituted with Leu, Leu at position 45 is substituted with Phe, Met at position 48 is substituted with Ile, Arg at position 67 is substituted with Lys, Val at position 68 is substituted with Ala and Ala at position 97 is substituted with Thr in the amino acid sequence represented by SEQ ID NO:12;
(4) an amino acid sequence in which Lys at position 12 is substituted with Val, Gln at position 39 is substituted with Leu, Leu at position 45 is substituted with Phe, Met at position 48 is substituted with Ile, Arg at position 67 is substituted with Lys, Ile at position 70 is substituted with Leu and Ala at position 97 is substituted with Thr in the amino acid sequence represented by SEQ ID NO:12;
(5) an amino acid sequence in which Lys at position 12 is substituted with Val, Gln at position 39 is substituted with Leu, Leu at position 45 is substituted with Phe, Met at position 48 is substituted with Ile, Arg at position 67 is substituted with Lys, Ala at position 72 is substituted with Val and Ala at position 97 is substituted with Thr in the amino acid sequence represented by SEQ ID NO:12;
(6) an amino acid sequence in which Lys at position 12 is substituted with Val, Gln at position 39 is substituted with Leu, Leu at position 45 is substituted with Phe, Met at position 48 is substituted with Ile, Arg at position 67 is substituted with Lys, Thr at position 74 is substituted with Lys and Ala at position 97 is substituted with Thr in the amino acid sequence represented by SEQ ID NO:12;
(7) an amino acid sequence in which Val at position 20 is substituted with Leu, Arg at position 38 is substituted with Lys, Gln at position 39 is substituted with Leu, Leu at position 45 is substituted with Phe, Met at position 48 is substituted with Ile, Arg at position 67 is substituted with Lys and Ala at position 97 is substituted with Thr in the amino acid sequence represented by SEQ ID NO:12;
(8) an amino acid sequence in which Val at position 20 is substituted with Leu, Gln at position 39 is substituted with Leu, Leu at position 45 is substituted with Phe, Met at position 48 is substituted with Ile, Arg at position 67 is substituted with Lys, Val at position 68 is substituted with Ala and Ala at position 97 is substituted with Thr in the amino acid sequence represented by SEQ ID NO:12;
(9) an amino acid sequence in which Val at position 20 is substituted with Leu, Gln at position 39 is substituted with Leu, Leu at position 45 is substituted with Phe, Met at position 48 is substituted with Ile, Arg at position 67 is substituted with Lys, Ile at position 70 is substituted with Leu and Ala at position 97 is substituted with Thr in the amino acid sequence represented by SEQ ID NO:12;
(10) an amino acid sequence in which Val at position 20 is substituted with Len, Gln at position 39 is substituted with Leu, Leu at position 45 is substituted with Phe, Met at position 48 is substituted with Ile, Arg at position 67 is substituted with Lys, Ala at position 72 is substituted with Val and Ala at position 97 is substituted with Thr in the amino acid sequence represented by SEQ ID NO:12;
(11) an amino acid sequence in which Val at position 20 is substituted with Leu, Gln at position 39 is substituted with Leu, Leu at position 45 is substituted with Phe, Met at position 48 is substituted with Ile, Arg at position 67 is substituted with Lys, Thr at position 74 is substituted with Lys and Ala at position 97 is substituted with Thr in the amino acid sequence represented by SEQ ID NO:12;
(12) an amino acid sequence in which Arg at position 38 is substituted with Lys, Gln at position 39 is substituted with Leu, Leu at position 45 is substituted with Phe, Met at position 48 is substituted with Ile, Arg at position 67 is substituted with Lys, Val at position 68 is substituted with Ala and Ala at position 97 is substituted with Thr in the amino acid sequence represented by SEQ ID NO:12;
(13) an amino acid sequence in which Arg at position 38 is substituted with Lys, Gln at position 39 is substituted with Leu, Leu at position 45 is substituted with Phe, Met at position 48 is substituted with Ile, Arg at position 67 is substituted with Lys, Ile at position 70 is substituted with Leu and Ala at position 97 is substituted with Thr in the amino acid sequence represented by SEQ ID NO:12;
(14) an amino acid sequence in which Arg at position 38 is substituted with Lys, Gln at position 39 is substituted with Leu, Leu at position 45 is substituted with Phe, Met at position 48 is substituted with Ile, Arg at position 67 is substituted with Lys, Ala at position 72 is substituted with Val and Ala at position 97 is substituted with Thr in the amino acid sequence represented by SEQ ID NO:12;
(15) an amino acid sequence in which Arg at position 38 is substituted with Lys, Gln at position 39 is substituted with Leu, Leu at position 45 is substituted with Phe, Met at position 48 is substituted with Ile, Arg at position 67 is substituted with Lys, Thr at position 74 is substituted with Lys and Ala at position 97 is substituted with Thr in the amino acid sequence represented by SEQ ID NO:12;

(16) an amino acid sequence in which Gln at position 39 is substituted with Leu, Leu at position 45 is substituted with Phe, Met at position 48 is substituted with Ile, Arg at position 67 is substituted with Lys, Val at position 68 is substituted with Ala, Ile at position 70 is substituted with Leu and Ala at position 97 is substituted with Thr in the amino acid sequence represented by SEQ ID NO:12;
(17) an amino acid sequence in which Gln at position 39 is substituted with Leu, Leu at position 45 is substituted with Phe, Met at position 48 is substituted with Ile, Arg at position 67 is substituted with Lys, Val at position 68 is substituted with Ala, Ala at position 72 is substituted with Val and Ala at position 97 is substituted with Thr in the amino acid sequence represented by SEQ ID NO:12;
(18) an amino acid sequence in which Gln at position 39 is substituted with Leu, Leu at position 45 is substituted with Phe, Met at position 48 is substituted with Ile, Arg at position 67 is substituted with Lys, Val at position 68 is substituted with Ala, Thr at position 74 is substituted with Lys and Ala at position 97 is substituted with Thr in the amino acid sequence represented by SEQ ID NO:12;
(19) an amino acid sequence in which Gln at position 39 is substituted with Leu, Leu at position 45 is substituted with Phe, Met at position 48 is substituted with Ile, Arg at position 67 is substituted with Lys, Ile at position 70 is substituted with Leu, Ala at position 72 is substituted with Val and Ala at position 97 is substituted with Thr in the amino acid sequence represented by SEQ ID NO:12;
(20) an amino acid sequence in which Gln at position 39 is substituted with Leu, Leu at position 45 is substituted with Phe, Met at position 48 is substituted with Ile, Arg at position 67 is substituted with Lys, Ile at position 70 is substituted with Leu, Thr at position 74 is substituted with Lys and Ala at position 97 is substituted with Thr in the amino acid sequence represented by SEQ ID NO:12;
(21) an amino acid sequence in which Leu at position 45 is substituted with Phe, Met at position 48 is substituted with Ile, Arg at position 67 is substituted with Lys, Val at position 68 is substituted with Ala, Ala at position 72 is substituted with Val, Thr at position 74 is substituted with Lys and Ala at position 97 is substituted with Thr in the amino acid sequence represented by SEQ ID NO:12;
(22) an amino acid sequence in which Gln at position 39 is substituted with Leu, Leu at position 45 is substituted with Phe, Met at position 48 is substituted with Ile, Arg at position 67 is substituted with Lys, Ala at position 72 is substituted with Val, Thr at position 74 is substituted with Lys and Ala at position 97 is substituted with Thr in the amino acid sequence represented by SEQ ID NO:12.

Specific examples of the amino acid sequence of VH in which six substitutions are introduced include the following (1) to (7) amino acid sequences:
(1) an amino acid sequence in which Lys at position 12 is substituted with Val, Gln at position 39 is substituted with Leu, Leu at position 45 is substituted with Phe, Met at position 48 is substituted with Ile, Arg at position 67 is substituted with Lys and Ala at position 97 is substituted with Thr in the amino acid sequence represented by SEQ ID NO:12;
(2) an amino acid sequence in which Val at position 20 is substituted with Leu, Gln at position 39 is substituted with Leu, Leu at position 45 is substituted with Phe, Met at position 48 is substituted with Ile, Arg at position 67 is substituted with Lys and Ala at position 97 is substituted with Thr in the amino acid sequence represented by SEQ ID NO:12;
(3) an amino acid sequence in which Arg at position 38 is substituted with Lys, Gln at position 39 is substituted with Leu, Leu at position 45 is substituted with Phe, Met at position 48 is substituted with Ile, Arg at position 67 is substituted with Lys and Ala at position 97 is substituted with Thr in the amino acid sequence represented by SEQ ID NO:12;
(4) an amino acid sequence in which Gln at position 39 is substituted with Leu, Leu at position 45 is substituted with Phe, Met at position 48 is substituted with Ile, Arg at position 67 is substituted with Lys, Val at position 68 is substituted with Ala and Ala at position 97 is substituted with Thr in the amino acid sequence represented by SEQ ID NO:12;
(5) an amino acid sequence in which Gln at position 39 is substituted with Leu, Leu at position 45 is substituted with Phe, Met at position 48 is substituted with Ile, Arg at position 67 is substituted with Lys, Ile at position 70 is substituted with Leu and Ala at position 97 is substituted with Thr in the amino acid sequence represented by SEQ ID NO:12;
(6) an amino acid sequence in which Gln at position 39 is substituted with Leu, Leu at position 45 is substituted with Phe, Met at position 48 is substituted with Ile, Arg at position 67 is substituted with Lys, Ala at position 72 is substituted with Val and Ala at position 97 is substituted with Thr in the amino acid sequence represented by SEQ ID NO:12;
(7) an amino acid sequence in which Gln at position 39 is substituted with Leu, Leu at position 45 is substituted with Phe, Met at position 48 is substituted with Ile, Arg at position 67 is substituted with Lys, Thr at position 74 is substituted with Lys and Ala at position 97 is substituted with Thr in the amino acid sequence represented by SEQ ID NO:12.

Specific examples of the amino acid sequence of VH in which five substitutions are introduced include the following (1) to (8) amino acid sequences:
(1) an amino acid sequence in which Lys at position 12 is substituted with Val, Leu at position 45 is substituted with Phe, Met at position 48 is substituted with Ile, Arg at position 67 is substituted with Lys and Ala at position 97 is substituted with Thr in the amino acid sequence represented by SEQ ID NO:12;
(2) an amino acid sequence in which Val at position 20 is substituted with Leu, Leu at position 45 is substituted with Phe, Met at position 48 is substituted with Ile, Arg at position 67 is substituted with Lys and Ala at position 97 is substituted with Thr in the amino acid sequence represented by SEQ ID NO:12;
(3) an amino acid sequence in which Arg at position 38 is substituted with Lys, Leu at position 45 is substituted with Phe, Met at position 48 is substituted with Ile, Arg at position 67 is substituted with Lys and Ala at position 97 is substituted with Thr in the amino acid sequence represented by SEQ ID NO:12;
(4) an amino acid sequence in which Gln at position 39 is substituted with Leu, Leu at position 45 is substituted with Phe, Met at position 48 is substituted with Ile, Arg at position 67 is substituted with Lys and Ala at position 97 is substituted with Thr in the amino acid sequence represented by SEQ ID NO:12;
(5) an amino acid sequence in which Leu at position 45 is substituted with Phe, Met at position 48 is substituted with Ile, Arg at position 67 is substituted with Lys, Val at position 68 is substituted with Ala and Ala at position 97 is substituted with Thr in the amino acid sequence represented by SEQ ID NO:12;

(6) an amino acid sequence in which Leu at position 45 is substituted with Phe, Met at position 48 is substituted with Ile, Arg at position 67 is substituted with Lys, Ile at position 70 is substituted with Leu and Ala at position 97 is substituted with Thr in the amino acid sequence represented by SEQ ID NO:12;

(7) an amino acid sequence in which Leu at position 45 is substituted with Phe, Met at position 48 is substituted with Ile, Arg at position 67 is substituted with Lys, Ala at position 72 is substituted with Val and Ala at position 97 is substituted with Thr in the amino acid sequence represented by SEQ ID NO:12;

(8) an amino acid sequence in which Leu at position 45 is substituted with Phe, Met at position 48 is substituted with Ile, Arg at position 67 is substituted with Lys, Thr at position 74 is substituted with Lys and Ala at position 97 is substituted with Thr in the amino acid sequence represented by SEQ ID NO:12.

Specific examples of the amino acid sequence of VH in which four substitutions are introduced include the following (1) to (9) amino acid sequences:

(1) an amino acid sequence in which Lys at position 12 is substituted with Val, Leu at position 45 is substituted with Phe, Met at position 48 is substituted with Ile and Ala at position 97 is substituted with Thr in the amino acid sequence represented by SEQ ID NO:12;

(2) an amino acid sequence in which Val at position 20 is substituted with Leu, Leu at position 45 is substituted with Phe, Met at position 48 is substituted with Ile and Ala at position 97 is substituted with Thr in the amino acid sequence represented by SEQ ID NO:12;

(3) an amino acid sequence in which Arg at position 38 is substituted with Lys, Leu at position 45 is substituted with Phe, Met at position 48 is substituted with Ile and Ala at position 97 is substituted with Thr in the amino acid sequence represented by SEQ ID NO:12;

(4) an amino acid sequence in which Gln at position 39 is substituted with Leu, Leu at position 45 is substituted with Phe, Met at position 48 is substituted with Ile and Ala at position 97 is substituted with Thr in the amino acid sequence represented by SEQ ID NO:12;

(5) an amino acid sequence in which Leu at position 45 is substituted with Phe, Met at position 48 is substituted with Ile, Arg at position 67 is substituted with Lys and Ala at position 97 is substituted with Thr in the amino acid sequence represented by SEQ ID NO:12;

(6) an amino acid sequence in which Leu at position 45 is substituted with Phe, Met at position 48 is substituted with Ile, Val at position 68 is substituted with Ala and Ala at position 97 is substituted with Thr in the amino acid sequence represented by SEQ ID NO:12;

(7) an amino acid sequence in which Leu at position 45 is substituted with Phe, Met at position 48 is substituted with Ile, Ile at position 70 is substituted with Leu and Ala at position 97 is substituted with Thr in the amino acid sequence represented by SEQ ID NO:12;

(8) an amino acid sequence in which Leu at position 45 is substituted with Phe, Met at position 48 is substituted with Ile, Ala at position 72 is substituted with Val and Ala at position 97 is substituted with Thr in the amino acid sequence represented by SEQ ID NO:12;

(9) an amino acid sequence in which Leu at position 45 is substituted with Phe, Met at position 48 is substituted with Ile, Thr at position 74 is substituted with Lys and Ala at position 97 is substituted with Thr in the amino acid sequence represented by SEQ ID NO:12.

Specific examples of the amino acid sequence of VH in which three substitutions are introduced include the following (1) to (19) amino acid sequences, for example:

(1) an amino acid sequence in which Lys at position 12 is substituted with Val, Leu at position 45 is substituted with Phe and Ala at position 97 is substituted with Thr in the amino acid sequence represented by SEQ ID NO:12;

(2) an amino acid sequence in which Val at position 20 is substituted with Leu, Leu at position 45 is substituted with Phe and Ala at position 97 is substituted with Thr in the amino acid sequence represented by SEQ ID NO:12;

(3) an amino acid sequence in which Arg at position 38 is substituted with Lys, Leu at position 45 is substituted with Phe and Ala at position 97 is substituted with Thr in the amino acid sequence represented by SEQ ID NO:12;

(4) an amino acid sequence in which Gln at position 39 is substituted with Leu, Leu at position 45 is substituted with Phe and Ala at position 97 is substituted with Thr in the amino acid sequence represented by SEQ ID NO:12;

(5) an amino acid sequence in which Leu at position 45 is substituted with Phe, Met at position 48 is substituted with Ile and Ala at position 97 is substituted with Thr in the amino acid sequence represented by SEQ ID NO:12;

(6) an amino acid sequence in which Leu at position 45 is substituted with Phe, Arg at position 67 is substituted with Lys and Ala at position 97 is substituted with Thr in the amino acid sequence represented by SEQ ID NO:12;

(7) an amino acid sequence in which Leu at position 45 is substituted with Phe, Val at position 68 is substituted with Ala and Ala at position 97 is substituted with Thr in the amino acid sequence represented by SEQ ID NO:12;

(8) an amino acid sequence in which Leu at position 45 is substituted with Phe, Ile at position 70 is substituted with Leu and Ala at position 97 is substituted with Thr in the amino acid sequence represented by SEQ ID NO:12;

(9) an amino acid sequence in which Leu at position 45 is substituted with Phe, Ala at position 72 is substituted with Val and Ala at position 97 is substituted with Thr in the amino acid sequence represented by SEQ ID NO:12;

(10) an amino acid sequence in which Leu at position 45 is substituted with Phe, Thr at position 74 is substituted with Lys and Ala at position 97 is substituted with Thr in the amino acid sequence represented by SEQ ID NO:12;

(11) an amino acid sequence in which Lys at position 12 is substituted with Val, Leu at position 45 is substituted with Phe and Met at position 48 is substituted with Ile in the amino acid sequence represented by SEQ ID NO:12;

(12) an amino acid sequence in which Val at position 20 is substituted with Leu, Leu at position 45 is substituted with Phe and Met at position 48 is substituted with Ile in the amino acid sequence represented by SEQ ID NO:12;

(13) an amino acid sequence in which Arg at position 38 is substituted with Lys, Leu at position 45 is substituted with Phe and Met at position 48 is substituted with Ile in the amino acid sequence represented by SEQ ID NO:12;

(14) an amino acid sequence in which Gln at position 39 is substituted with Leu, Leu at position 45 is substituted with Phe and Met at position 48 is substituted with Ile in the amino acid sequence represented by SEQ ID NO:12;

(15) an amino acid sequence in which Leu at position 45 is substituted with Phe, Met at position 48 is substituted with Ile and Arg at position 67 is substituted with Lys in the amino acid sequence represented by SEQ ID NO:12;

(16) an amino acid sequence in which Leu at position 45 is substituted with Phe, Met at position 48 is substituted with Ile and Val at position 68 is substituted with Ala in the amino acid sequence represented by SEQ ID NO:12;

(17) an amino acid sequence in which Leu at position 45 is substituted with Phe, Met at position 48 is substituted with Ile and Ile at position 70 is substituted with Leu in the amino acid sequence represented by SEQ ID NO:12;

(18) an amino acid sequence in which Leu at position 45 is substituted with Phe, Met at position 48 is substituted with Ile and Ala at position 72 is substituted with Val in the amino acid sequence represented by SEQ ID NO:12;

(19) an amino acid sequence in which Leu at position 45 is substituted with Phe, Met at position 48 is substituted with Ile and Thr at position 74 is substituted with Lys in the amino acid sequence represented by SEQ ID NO:12.

Specific examples of the amino acid sequence of VH in which two substitutions are introduced include the following (1) to (66) amino acid sequences, for example:

(1) an amino acid sequence in which Lys at position 12 is substituted with Val and Val at position 20 is substituted with Leu in the amino acid sequence represented by SEQ ID NO:12;

(2) an amino acid sequence in which Lys at position 12 is substituted with Val and Arg at position 38 is substituted with Lys in the amino acid sequence represented by SEQ ID NO:12;

(3) an amino acid sequence in which Lys at position 12 is substituted with Val and Gln at position 39 is substituted with Leu in the amino acid sequence represented by SEQ ID NO:12;

(4) an amino acid sequence in which Lys at position 12 is substituted with Val and Leu at position 45 is substituted with Phe in the amino acid sequence represented by SEQ ID NO:12;

(5) an amino acid sequence in which Lys at position 12 is substituted with Val and Met at position 48 is substituted with Ile in the amino acid sequence represented by SEQ ID NO:12;

(6) an amino acid sequence in which Lys at position 12 is substituted with Val and Arg at position 67 is substituted with Lys in the amino acid sequence represented by SEQ ID NO:12;

(7) an amino acid sequence in which Lys at position 12 is substituted with Val and Val at position 68 is substituted with Ala in the amino acid sequence represented by SEQ ID NO:12;

(8) an amino acid sequence in which Lys at position 12 is substituted with Val and Ile at position 70 is substituted with Leu in the amino acid sequence represented by SEQ ID NO:12;

(9) an amino acid sequence in which Lys at position 12 is substituted with Val and Ala at position 72 is substituted with Val in the amino acid sequence represented by SEQ ID NO:12;

(10) an amino acid sequence in which Lys at position 12 is substituted with Val and Thr at position 74 is substituted with Lys in the amino acid sequence represented by SEQ ID NO:12;

(11) an amino acid sequence in which Lys at position 12 is substituted with Val and Ala at position 97 is substituted with Thr in the amino acid sequence represented by SEQ ID NO:12;

(12) an amino acid sequence in which Val at position 20 is substituted with Leu and Arg at position 38 is substituted with Lys in the amino acid sequence represented by SEQ ID NO:12;

(13) an amino acid sequence in which Val at position 20 is substituted with Leu and Gln at position 39 is substituted with Leu in the amino acid sequence represented by SEQ ID NO:12;

(14) an amino acid sequence in which Val at position 20 is substituted with Leu and Leu at position 45 is substituted with Phe in the amino acid sequence represented by SEQ ID NO:12;

(15) an amino acid sequence in which Val at position 20 is substituted with Leu and Met at position 48 is substituted with Ile in the amino acid sequence represented by SEQ ID NO:12;

(16) an amino acid sequence in which Val at position 20 is substituted with Leu and Arg at position 67 is substituted with Lys in the amino acid sequence represented by SEQ ID NO:12;

(17) an amino acid sequence in which Val at position 20 is substituted with Leu and Val at position 68 is substituted with Ala in the amino acid sequence represented by SEQ ID NO:12;

(18) an amino acid sequence in which Val at position 20 is substituted with Leu and Ile at position 70 is substituted with Leu in the amino acid sequence represented by SEQ ID NO:12;

(19) an amino acid sequence in which Val at position 20 is substituted with Leu and Ala at position 72 is substituted with Val in the amino acid sequence represented by SEQ ID NO:12;

(20) an amino acid sequence in which Val at position 20 is substituted with Leu and Thr at position 74 is substituted with Lys in the amino acid sequence represented by SEQ ID NO:12;

(21) an amino acid sequence in which Val at position 20 is substituted with Leu and Ala at position 97 is substituted with Thr in the amino acid sequence represented by SEQ ID NO:12;

(22) an amino acid sequence in which Arg at position 38 is substituted with Lys and Gln at position 39 is substituted with Leu in the amino acid sequence represented by SEQ ID NO:12;

(23) an amino acid sequence in which Arg at position 38 is substituted with Lys and Leu at position 45 is substituted with Phe in the amino acid sequence represented by SEQ ID NO:12;

(24) an amino acid sequence in which Arg at position 38 is substituted with Lys and Met at position 48 is substituted with Ile in the amino acid sequence represented by SEQ ID NO:12;

(25) an amino acid sequence in which Arg at position 38 is substituted with Lys and Arg at position 67 is substituted with Lys in the amino acid sequence represented by SEQ ID NO:12;

(26) an amino acid sequence in which Arg at position 38 is substituted with Lys and Val at position 68 is substituted with Ala in the amino acid sequence represented by SEQ ID NO:12;

(27) an amino acid sequence in which Arg at position 38 is substituted with Lys and Ile at position 70 is substituted with Leu in the amino acid sequence represented by SEQ ID NO:12;

(28) an amino acid sequence in which Arg at position 38 is substituted with Lys and Ala at position 72 is substituted with Val in the amino acid sequence represented by SEQ ID NO:12;

(29) an amino acid sequence in which Arg at position 38 is substituted with Lys and Thr at position 74 is substituted with Lys in the amino acid sequence represented by SEQ ID NO:12;
(30) an amino acid sequence in which Arg at position 38 is substituted with Lys and Ala at position 97 is substituted with Thr in the amino acid sequence represented by SEQ ID NO:12;
(31) an amino acid sequence in which Gln at position 39 is substituted with Leu and
Leu at position 45 is substituted with Phe in the amino acid sequence represented by SEQ ID NO:12;
(32) an amino acid sequence in which Gln at position 39 is substituted with Leu and Met at position 48 is substituted with Ile in the amino acid sequence represented by SEQ ID NO:12;
(33) an amino acid sequence in which Gln at position 39 is substituted with Leu and Arg at position 67 is substituted with Lys in the amino acid sequence represented by SEQ ID NO:12;
(34) an amino acid sequence in which Gln at position 39 is substituted with Leu and Val at position 68 is substituted with Ala in the amino acid sequence represented by SEQ ID NO:12;
(35) an amino acid sequence in which Gln at position 39 is substituted with Leu and Ile at position 70 is substituted with Leu in the amino acid sequence represented by SEQ ID NO:12;
(36) an amino acid sequence in which Gln at position 39 is substituted with Leu and Ala at position 72 is substituted with Val in the amino acid sequence represented by SEQ ID NO:12;
(37) an amino acid sequence in which Gln at position 39 is substituted with Leu and Thr at position 74 is substituted with Lys in the amino acid sequence represented by SEQ ID NO:12;
(38) an amino acid sequence in which Gln at position 39 is substituted with Leu and Ala at position 97 is substituted with Thr in the amino acid sequence represented by SEQ ID NO:12;
(39) an amino acid sequence in which Leu at position 45 is substituted with Phe and Met at position 48 is substituted with Ile in the amino acid sequence represented by SEQ ID NO:12;
(40) an amino acid sequence in which Leu at position 45 is substituted with Phe and Arg at position 67 is substituted with Lys in the amino acid sequence represented by SEQ ID NO:12;
(41) an amino acid sequence in which Leu at position 45 is substituted with Phe and Val at position 68 is substituted with Ala in the amino acid sequence represented by SEQ ID NO:12;
(42) an amino acid sequence in which Leu at position 45 is substituted with Phe and Ile at position 70 is substituted with Leu in the amino acid sequence represented by SEQ ID NO:12;
(43) an amino acid sequence in which Leu at position 45 is substituted with Phe and Ala at position 72 is substituted with Val in the amino acid sequence represented by SEQ ID NO:12;
(44) an amino acid sequence in which Leu at position 45 is substituted with Phe and Thr at position 74 is substituted with Lys in the amino acid sequence represented by SEQ ID NO:12;
(45) an amino acid sequence in which Leu at position 45 is substituted with Phe and Ala at position 97 is substituted with Thr in the amino acid sequence represented by SEQ ID NO:12;
(46) an amino acid sequence in which Met at position 48 is substituted with Ile and Arg at position 67 is substituted with Lys in the amino acid sequence represented by SEQ ID NO:12;
(47) an amino acid sequence in which Met at position 48 is substituted with Ile and Val at position 68 is substituted with Ala in the amino acid sequence represented by SEQ ID NO:12;
(48) an amino acid sequence in which Met at position 48 is substituted with Ile and Ile at position 70 is substituted with Leu in the amino acid sequence represented by SEQ ID NO:12;
(49) an amino acid sequence in which Met at position 48 is substituted with Ile and Ala at position 72 is substituted with Val in the amino acid sequence represented by SEQ ID NO:12;
(50) an amino acid sequence in which Met at position 48 is substituted with Ile and Thr at position 74 is substituted with Lys in the amino acid sequence represented by SEQ ID NO:12;
(51) an amino acid sequence in which Met at position 48 is substituted with Ile and Ala at position 97 is substituted with Thr in the amino acid sequence represented by SEQ ID NO:12;
(52) an amino acid sequence in which Arg at position 67 is substituted with Lys and Val at position 68 is substituted with Ala in the amino acid sequence represented by SEQ ID NO:12;
(53) an amino acid sequence in which Arg at position 67 is substituted with Lys and Ile at position 70 is substituted with Leu in the amino acid sequence represented by SEQ ID NO:12;
(54) an amino acid sequence in which Arg at position 67 is substituted with Lys and Ala at position 72 is substituted with Val in the amino acid sequence represented by SEQ ID NO:12;
(55) an amino acid sequence in which Arg at position 67 is substituted with Lys and Thr at position 74 is substituted with Lys in the amino acid sequence represented by SEQ ID NO:12;
(56) an amino acid sequence in which Arg at position 67 is substituted with Lys and Ala at position 97 is substituted with Thr in the amino acid sequence represented by SEQ ID NO:12;
(57) an amino acid sequence in which Val at position 68 is substituted with Ala and Ile at position 70 is substituted with Leu in the amino acid sequence represented by SEQ ID NO:12;
(58) an amino acid sequence in which Val at position 68 is substituted with Ala and Ala at position 72 is substituted with Val in the amino acid sequence represented by SEQ ID NO:12;
(59) an amino acid sequence in which Val at position 68 is substituted with Ala and Thr at position 74 is substituted with Lys in the amino acid sequence represented by SEQ ID NO:12;
(60) an amino acid sequence in which Val at position 68 is substituted with Ala and Ala at position 97 is substituted with Thr in the amino acid sequence represented by SEQ ID NO:12;

(61) an amino acid sequence in which Ile at position 70 is substituted with Leu and Ala at position 72 is substituted with Val in the amino acid sequence represented by SEQ ID NO:12;
(62) an amino acid sequence in which Ile at position 70 is substituted with Leu and Thr at position 74 is substituted with Lys in the amino acid sequence represented by SEQ ID NO:12;
(63) an amino acid sequence in which Ile at position 70 is substituted with Leu and Ala at position 97 is substituted with Thr in the amino acid sequence represented by SEQ ID NO:12;
(64) an amino acid sequence in which Ala at position 72 is substituted with Val and Thr at position 74 is substituted with Lys in the amino acid sequence represented by SEQ ID NO:12;
(65) an amino acid sequence in which Ala at position 72 is substituted with Val and Ala at position 97 is substituted with Thr in the amino acid sequence represented by SEQ ID NO:12;
(66) an amino acid sequence in which Thr at position 74 is substituted with Lys and Ala at position 97 is substituted with Thr in the amino acid sequence represented by SEQ ID NO:12.

Specific examples of the amino acid sequence of VH in which a substitution is introduced include the following (1) to (12) amino acid sequences, for example:
(1) an amino acid sequence in which Lys at position 12 is substituted with Val in the amino acid sequence represented by SEQ ID NO:12;
(2) an amino acid sequence in which Val at position 20 is substituted with Leu in the amino acid sequence represented by SEQ ID NO:12;
(3) an amino acid sequence in which Arg at position 38 is substituted with Lys in the amino acid sequence represented by SEQ ID NO:12;
(4) an amino acid sequence in which Gln at position 39 is substituted with Leu in the amino acid sequence represented by SEQ ID NO:12;
(5) an amino acid sequence in which Leu at position 45 is substituted with Phe in the amino acid sequence represented by SEQ ID NO:12;
(6) an amino acid sequence in which Met at position 48 is substituted with Ile in the amino acid sequence represented by SEQ ID NO:12;
(7) an amino acid sequence in which Arg at position 67 is substituted with Lys in the amino acid sequence represented by SEQ ID NO:12;
(8) an amino acid sequence in which Val at position 68 is substituted with Ala in the amino acid sequence represented by SEQ ID NO:12;
(9) an amino acid sequence in which Ile at position 70 is substituted with Leu in the amino acid sequence represented by SEQ ID NO:12;
(10) an amino acid sequence in which Ala at position 72 is substituted with Val in the amino acid sequence represented by SEQ ID NO:12;
(11) an amino acid sequence in which Thr at position 74 is substituted with Lys in the amino acid sequence represented by SEQ ID NO:12;
(12) an amino acid sequence in which Ala at position 97 is substituted with Thr in the amino acid sequence represented by SEQ ID NO:12.

Among the above amino acid sequences of VH, the amino acid sequence represented by SEQ ID NO:12, an amino acid sequence in which Lys at position 12 is substituted with Val, Val at position 20 is substituted with Leu, Arg at position 38 is substituted with Lys, Gln at position 39 is substituted with Leu, Leu at position 45 is substituted with Phe, Met at position 48 is substituted with Ile, Arg at position 67 is substituted with Lys, Val at position 68 is substituted with Ala, Ile at position 70 is substituted with Leu, Ala at position 72 is substituted with Val, Thr at position 74 is substituted with Lys and Ala at position 97 is substituted with Thr in the amino acid sequence represented by SEQ ID NO:12 are preferable.

The humanized antibody of the present invention preferably includes VL comprising an amino acid sequence in which Ile at position 2, Pro at position 15, Gln at position 50, Tyr at position 92 in the amino acid sequence represented by SEQ ID NO:14 are substituted with other amino acid residues, and preferable examples of VL of the present invention also include VL comprising an amino acid sequence in which Pro at position 15, Gln at position 50, Tyr at position 92 in the amino acid sequence represented by SEQ ID NO:14 are substituted with other amino acid residues.

In addition, VL selected from the following (1) to (4) is also preferable as VL contained in the humanized antibody of the present invention:
(1) VL comprising an amino acid sequence in which Gln at position 50 and Tyr at position 92 in the amino acid sequence represented by SEQ ID NO:14 are substituted with other amino acid residues;
(2) VL comprising an amino acid sequence in which Ile at position 2 and Tyr at position 92 in the amino acid sequence represented by SEQ ID NO:14 are substituted with other amino acid residues;
(3) VL comprising an amino acid sequence in which Pro at position 15 and Tyr at position 92 in the amino acid sequence represented by SEQ ID NO:14 are substituted with other amino acid residues;
(4) VL comprising an amino acid sequence in which Ile at position 2 and Gln at position 50 in the amino acid sequence represented by SEQ ID NO:14 is substituted with another amino acid residue.

The amino acid sequence of the VL include, for example, an amino acid sequence in which at least one modification selected from modifications of substituting Ile at position 2 with Val, Pro at position 15 with Leu, Gln at position 50 with Lys and Tyr at position 92 with Phe in the amino acid sequence represented by SEQ ID NO:14 is introduced.

More specific examples of the amino acid sequence of the VL in the antibody of the present invention in which the above modifications are introduced include, for example, the amino acid sequence of the VL in which the following four to one substitutions are introduced.

Specific examples of the amino acid sequence of VL in which four substitutions are introduced include an amino acid sequence in which Ile at position 2 is substituted with Val, Pro at position 15 is substituted with Leu, Gln at position 50 is substituted with Lys and Tyr at position 92 is substituted with Phe in the amino acid sequence represented by SEQ ID NO:14.

Specific examples of the amino acid sequence of VL in which three substitutions are introduced include the following (1) to (4) amino acid sequences:
(1) an amino acid sequence in which Ile at position 2 is substituted with Val, Pro at position 15 is substituted with Leu and Gln at position 50 is substituted with Lys in the amino acid sequence represented by SEQ ID NO:14;
(2) an amino acid sequence in which Ile at position 2 is substituted with Val, Pro at position 15 is substituted with Leu and Tyr at position 92 is substituted with Phe in the amino acid sequence represented by SEQ ID NO:14;

(3) an amino acid sequence in which Ile at position 2 is substituted with Val, Gln at position 50 is substituted with Lys and Tyr at position 92 is substituted with Phe in the amino acid sequence represented by SEQ ID NO:14;
(4) an amino acid sequence in which Pro at position 15 is substituted with Leu, Gln at position 50 is substituted with Lys and Tyr at position 92 is substituted with Phe in the amino acid sequence represented by SEQ ID NO:14.

Specific examples of the amino acid sequence of VL in which two substitutions are introduced include the following (1) to (6) amino acid sequences:
(1) an amino acid sequence in which Ile at position 2 is substituted with Val and Pro at position 15 is substituted with Leu in the amino acid sequence represented by SEQ ID NO:14;
(2) an amino acid sequence in which Ile at position 2 is substituted with Val and Gln at position 50 is substituted with Lys in the amino acid sequence represented by SEQ ID NO:14;
(3) an amino acid sequence in which Ile at position 2 is substituted with Val and Tyr at position 92 is substituted with Phe in the amino acid sequence represented by SEQ ID NO:14;
(4) an amino acid sequence in which Pro at position 15 is substituted with Leu and Gln at position 50 is substituted with Lys in the amino acid sequence represented by SEQ ID NO:14;
(5) an amino acid sequence in which Pro at position 15 is substituted with Leu and Tyr at position 92 is substituted with Phe in the amino acid sequence represented by SEQ ID NO:14;
(6) an amino acid sequence in which Gln at position 50 is substituted with Lys and Tyr at position 92 is substituted with Phe in the amino acid sequence represented by SEQ ID NO:14.

Specific examples of the amino acid sequence of VL in which one substitution is introduced include the following (1) to (4) amino acid sequences:
(1) an amino acid sequence in which Ile at position 2 is substituted with Val in the amino acid sequence represented by SEQ ID NO:14;
(2) an amino acid sequence in which Pro at position 15 is substituted with Leu in the amino acid sequence represented by SEQ ID NO:14;
(3) an amino acid sequence in which Gln at position 50 is substituted with Lys in the amino acid sequence represented by SEQ ID NO:14;
(4) an amino acid sequence in which Tyr at position 92 is substituted with Phe in the amino acid sequence represented by SEQ ID NO:14.

Among the above amino acid sequences of VL, the amino acid sequence represented by SEQ ID NO:14, an amino acid sequence in which Ile at position 2 is substituted with Val, Pro at position 15 is substituted with Leu, Gln at position 50 is substituted with Lys and Tyr at position 92 is substituted with Phe in the amino acid sequence represented by SEQ ID NO:14, and an amino acid sequence in which Gln at position 50 is substituted with Lys and Tyr at position 92 is substituted with Phe in the amino acid sequence represented by SEQ ID NO:14 are preferable.

Specific examples of the antibody of the present invention include any one of the antibodies each of which is obtained by combining the above mentioned VH and VL, respectively.

Preferable examples of the antibody of the present invention include the following antibodies (1) to (4), for example:
(1) a humanized antibody comprising VH which comprises the amino acid sequence represented by SEQ ID NO:12 and VL which comprises the amino acid sequence represented by SEQ ID NO:14;
(2) a humanized antibody comprising VH which comprises the amino acid sequence represented by SEQ ID NO:12 and VL which comprises any one of the amino acid sequences shown in FIG. 2;
(3) a humanized antibody comprising VH which comprises any one of the amino acid sequences shown in FIG. 1 and VL which comprises the amino acid sequence represented by SEQ ID NO:14;
(4) a humanized antibody comprising VH which comprises any one of the amino acid sequences shown in FIG. 1 and VL which comprises any one of the amino acid sequences shown in FIG. 2.

Among the amino acid sequences of the VH shown in FIG. 1, 6E4HV0 and HV12 are preferable. In addition, among the amino acid sequences of the VL shown in FIG. 2, 6E4LV0, LV2a and LV4 are preferable.

Accordingly, as the humanized antibody comprising VH which comprises any one of the amino acid sequences shown in FIG. 1 and VL which comprises any one of the amino acid sequences shown in FIG. 2, the humanized antibody comprising VH which comprises any one of the amino acid sequences among 6E4HV0 and HV12 shown in FIG. 1 and VL which comprises any one of the amino acid sequences among 6E4LV0, LV2a and LV4 shown in FIG. 2 is preferable.

Specifically, examples include the humanized antibody comprising VH which comprises the amino acid sequences represented by SEQ ID NO:12 or 15 and VL which comprises any one of the amino acid sequences represented by SEQ ID NOs:14, 16 and 17.

As the combination of the amino acid sequence of VH shown in FIG. 1 and the amino acid sequence of VL shown in FIG. 2, the combinations of HV0 and LV0, HV0 and LV2a, HV0 and LV4 and HV12 and LV4 are preferable.

Accordingly, as the antibody of the present invention, the following humanized antibodies (1) to (4) are more preferable:
(1) a humanized antibody (HV0LV0) comprising VH which comprises the amino acid sequence represented as HV0 in FIG. 1 and VL which comprises the amino acid sequence represented as LV0 in FIG. 2;
(2) a humanized antibody (HV0LV2a) comprising VH which comprises the amino acid sequence represented as HV0 in FIG. 1 and VL which comprises the amino acid sequence represented as LV2a in FIG. 2;
(3) a humanized antibody (HV0LV4) comprising VH which comprises the amino acid sequence represented as HV0 in FIG. 1 and VL which comprises the amino acid sequence represented as LV4 in FIG. 2;
(4) a humanized antibody (HV12LV4) comprising VH which comprises the amino acid sequence represented as HV12 in FIG. 1 and VL which comprises the amino acid sequence represented as LV4 in FIG. 2.

Specific examples of the above antibodies include a humanized antibody in which the combination of the amino acid sequences contained in VH and VL are SEQ ID NOs:12 and 14; SEQ ID NOs:12 and 16; SEQ ID NOs:12 and 17; and SEQ ID NOs:15 and 17.

In addition, examples of the humanized antibody of the present invention includes a humanized antibody which competes with the above humanized antibody in the binding of an Aβ oligomer and a humanized antibody which binds to an epitope which is the same as the epitope recognized by the above humanized antibody.

In the present invention, a human antibody is originally an antibody naturally existing in the human body, and it also includes antibodies obtained from a human antibody phage library, a human antibody-producing transgenic animal, and the like, which are prepared based on the recent advance in genetic engineering, cell engineering and developmental engineering techniques.

The antibody existing in the human body can be prepared, for example by isolating a human peripheral blood lymphocyte, immortalizing it by infecting with EB virus or the like and then cloning it to thereby obtain lymphocytes capable of producing the antibody, culturing the lymphocytes thus obtained, and purifying the antibody from the supernatant of the culture.

The human antibody phage library is a library in which antibody fragments such as Fab and scFv are expressed on the phage surface by inserting a gene encoding an antibody prepared from a human B cell into a phage gene.

A phage expressing an antibody fragment having the desired antigen binding activity on the cell surface can be recovered from the library, using its activity to bind to an antigen-immobilized substrate as the index. The antibody fragment can be converted further into a human antibody molecule comprising two full H chains and two full L chains by genetic engineering techniques.

A human antibody-producing transgenic animal is an animal in which a human antibody gene is integrated into cells. Specifically, a human antibody-producing transgenic animal can be prepared by introducing a gene encoding a human antibody into a mouse ES cell, grafting the ES cell into an early stage embryo of other mouse and then developing it into a complete animal.

A human antibody derived from the human antibody-producing transgenic non-human animal can be prepared by obtaining a human antibody-producing hybridoma by a hybridoma preparation method usually carried out in non-human animals, culturing the obtained hybridoma and producing and accumulating the human antibody in the supernatant of the culture.

An antibody or antibody fragment thereof in which one or more amino acids are deleted, substituted, inserted or added into the amino acid sequence constituting the above antibody or antibody fragment, having activity similar to the above antibody or antibody fragment is also included in the antibody or antibody fragment of the present invention.

The number of amino acid residues which are deleted, substituted, inserted and/or added is one or more, and is not specifically limited, but it is within the range where deletion, substitution or addition is possible by known methods such as the site-directed mutagenesis described in *Molecular Cloning*, Second Edition, Cold Spring Harbor Laboratory Press (1989); *Current Protocols in Molecular Biology*, John Willy & Sons (1987-1997); *Nucleic Acids Research*, 10, 6487 (1982), *Proc. Natl. Acad. Sci., USA*, 79, 6409 (1982); *Gene*, 34, 315 (1985), Nucleic *Acids Research*, 13, 4431 (1985); *Proc. Natl. Acad. Sci. USA*, 82, 488 (1985) or the like. For example, the number is 1 to dozens, preferably 1 to 20, more preferably 1 to 10, and most preferably 1 to 5.

Deleting, substituting, inserting or adding one or more amino acid residues in the amino acid sequence of the above antibody means the followings. That is, it means there is deletion, substitution, insertion or addition of one or plural amino acid residues at any positions in one or plural amino acid sequences of the antibody within a single sequence. Also, the deletion, substitution, insertion or addition may occur at the same time and the amino acid which is substituted, inserted or added may be either a natural type or a non-natural type.

The natural type amino acid includes L-alanine, L-asparagine, L-aspartic acid, L-glutamine, L: glutamic acid, glycine, L-histidine, L-isoleucine, L-leucine, L-lysine, L-arginine, L-methionine, L-phenylalanine, L-proline, L-serine, L-threonine, L-tryptophan, L-tyrosine, L-valine, L-cysteine and the like.

Preferable examples of mutually substitutable amino acids are shown below. The amino acids in the same group are mutually substitutable.

Group A: leucine, isoleucine, norleucine, valine, norvaline, alanine, 2-aminobutanoic acid, methionine, O-methylserine, t-butylglycine, t-butylalanine, cyclohexylalanine Group B: aspartic acid, glutamic acid, isoaspartic acid, isoglutamic acid, 2-aminoadipic acid, 2-aminosuberic acid Group C: asparagine, glutamine Group D: lysine, arginine, ornithine, 2,4-diaminobutanoic acid, 2,3-diaminopropionic acid Group E: proline, 3-hydroxyproline, 4-hydroxyproline Group F: serine, threonine, homoserine Group G: phenylalanine, tyrosine The antibody fragment of the present invention includes Fab, F(ab')$_2$, Fab', scFv, diabody, dsFv, a peptide comprising CDR and the like.

An Fab is an antibody fragment having a molecular weight of about 50,000 and having antigen binding activity, in which about a half of the N-terminal side of H chain and the entire L chain, among fragments obtained by treating an IgG antibody molecule with a protease, papain (cleaved at an amino acid residue at position 224 of the H chain), are bound through a disulfide bond.

The Fab of the present invention can be obtained by treating a monoclonal antibody which specifically recognizes an Aβ oligomer and binds to the extracellular domain, with a protease, papain. Also, the Fab can be produced by inserting DNA encoding Fab of the antibody into an expression vector for prokaryote or an expression vector for eukaryote, and introducing the vector into a prokaryote or eukaryote to express the Fab.

An F(ab')$_2$ is an antibody fragment having a molecular weight of about 100,000 and antigen binding activity and comprising two Fab regions which are bound in the hinge portion obtained by digesting the lower part of two disulfide bonds in the hinge region of IgG, with an enzyme, pepsin.

The F(ab")$_2$ of the present invention can be obtained by treating a monoclonal antibody which specifically recognizes an Aβ oligomer and binds to the extracellular domain, with a protease, pepsin. Also, the F(ab')$_2$ can be produced by binding Fab' described below via a thioether bond or a disulfide bond.

An Fab' is an antibody fragment having a molecular weight of about 50,000 and antigen binding activity, which is obtained by cleaving a disulfide bond at the hinge region of the above F(ab')$_2$.

The Fab' of the present invention can be obtained by treating F(ab')$_2$ which specifically recognizes an Aβ oligomer and binds to the extracellular domain, with a reducing agent, dithiothreitol.

Also, the Fab' can be produced by inserting DNA encoding Fab' fragment of the antibody into an expression vector for prokaryote or an expression vector for eukaryote, and introducing the vector into a prokaryote or eukaryote to express the Fab'.

An scFv is a VH-P-VL or VL-P-VH polypeptide in which a VH chain and a VL chain are linked using an appropriate peptide linker (hereinafter referred to as "P") and is an antibody fragment having antigen binding activity.

The scFv of the present invention can be produced by obtaining cDNAs encoding VH and VL of a monoclonal antibody which specifically recognizes an Aβ oligomer and binds to the extracellular domain, constructing DNA encoding the scFv, inserting the DNA into an expression vector for prokaryote or an expression vector for eukaryote, and then introducing the expression vector into a prokaryote or eukaryote to express the scFv.

A diabody is an antibody fragment wherein scFv is dimerized, and has divalent antigen binding activity. In the divalent antigen binding activity, two antigens may be the same or different.

The diabody of the present invention can be produced by obtaining cDNAs encoding VH and VL of a monoclonal antibody which specifically recognizes an Aβ oligomer and binds to the extracellular domain, constructing DNA encoding the scFv so that the length of the amino acid sequence of P is 8 or less residues, inserting the DNA into an expression vector for prokaryote or an expression vector for eukaryote, and then introducing the expression vector into a prokaryote or eukaryote to express the diabody.

A dsFv is obtained by binding polypeptides in which one amino acid residue of each of VH and VL is substituted with a cysteine residue via a disulfide bond between the cysteine residues. The amino acid residue to be substituted with a cysteine residue can be selected based on a three-dimensional structure estimation of the antibody in accordance with the method shown by Reiter et al. [*Protein Engineering,* 7, 697 (1994)].

The dsFv of the present invention can be produced by obtaining cDNAs encoding VH and VL of a monoclonal antibody which specifically recognizes an Aβ oligomer and binds to the extracellular domain, constructing DNA encoding dsFv, inserting the DNA into an expression vector for prokaryote or an expression vector for eukaryote, and then introducing the expression vector into a prokaryote or eukaryote to express the dsFv.

A peptide comprising CDR is constituted by including at least one region or more of CDRs of VH or VL. A peptide comprising plural CDRs can be produced by connecting CDRs directly or via an appropriate peptide linker.

The peptide comprising CDR of the present invention can be produced by constructing DNA encoding CDRs of VH and VL of a humanized antibody which specifically recognizes an Aβ oligomer of the present invention, inserting the DNA into an expression vector for prokaryote or an expression vector for eukaryote, and then introducing the expression vector into a prokaryote or eukaryote to express the peptide. The peptide comprising CDR can also be produced by a chemical synthesis method such as Fmoc method and tBoc method.

The antibody of the present invention includes an antibody derivative in which the anti-Aβ oligomer humanized antibody of the present invention or the antibody fragment thereof is chemically or genetically bound to a radioisotope, a low-molecular agent, a high-molecular agent, a protein, a therapeutic antibody and the like.

The antibody derivative of the present invention can be produced by chemically conjugating a radioisotope a low-molecular agent, a high-molecular agent, a protein, a therapeutic antibody and the like to the N-terminal side or C-terminal side of an H chain or an L chain of the anti-Aβ oligomer humanized antibody or the antibody fragment thereof, an appropriate substituent or side chain in the antibody or the antibody fragment, a sugar chain in the antibody or the antibody fragment and the like [*Antibody Engineering Handbook* published by Chijin Shokan (1994)].

Also, the antibody derivative of the present invention can be genetically produced by linking a DNA encoding the anti-Aβ oligomer humanized antibody of the present invention or the antibody fragment thereof to other DNA encoding a protein to be conjugated or DNA encoding a therapeutic antibody, inserting the DNA into a vector for expression, and introducing the expression vector into a host cell.

In the case where the above antibody derivative is used as a detection regent, a regent for quantitative determination or a diagnostic agent for the detection method, quantification method or diagnosis method, respectively, examples of the agent to which the anti-Aβ oligomer humanized antibody or the antibody fragment thereof in the present invention is conjugated includes a label which is generally used in immunological detecting or measuring method.

The label includes enzymes such as alkaline phosphatase, peroxidase and luciferase, luminescent materials such as acridinium ester and lophine, fluorescent materials such as fluorescein isothiocyanate (FITC) and tetramethyl rhodamine isothiocyanate (RITC).

Hereinafter, a method for producing the antibody is described.

1. Production of Anti-Aβ Oligomer Monoclonal Antibody

In the present invention, the anti-Aβ oligomer monoclonal antibody can be produced in the following manner.

(1) Preparation of Antigen

As a method for producing an Aβ oligomer as antigens, a synthetic Aβ1-42 (Peptide Institute, Inc. Osaka) is dissolved in deionized distilled water or in 10 mmol/L of phosphate buffer and incubated at 37° C. for 18 hours, and the peptide is separated by 4 to 12% SDS-PAGE, and the resulting material is visualized by CBB staining, only an Aβ1-42 tetramer without contamination of an Aβ1-42 monomer are then collected, and thereby Aβ1-42 oligomers can be produced.

Aβ1-40 oligomers comprising more oligomers can be prepared by chemical conjugation of 6-carboxytetramethyl-rhodamine (6-TAMRA) (SIGMA) to the N-terminal of the synthesized Aβ1-40 peptide using a conventional method, followed by polymerization reaction with the synthetic Aβ1-40 (Peptide Institute, Inc. Osaka).

(2) Immunization of Animals

First, 2.5 μg of Aβ1-42 tetramers or Aβ1-40 oligomers is emulsified by complete Freund's adjuvant. Then, the antigen is immunized on a footpad of a Balb-c mouse. And subsequently, six additional immunizations are performed. The fusion between antibody-producing cells and myeloma cells can be performed in a known method such as a method by Kohler and Milstein, et al. (Kohler. G and Milstein, C., *Methods Enzymol.* (1981) 73, 3-46) or the like. Specifically, immunocytes producing the antibody are obtained from inguinal lymph nodes of a mouse to which the antigen has been immunized.

The immunization is carried out by administering the antigen to the animal through subcutaneous, intravenous or intraperitoneal injection together with an appropriate adjuvant such as complete Freund's adjuvant and combination of aluminum hydroxide gel with pertussis vaccine.

When a partial peptide is used as the antigen, a conjugate to a carrier protein such as BSA (bovine serum albumin) and KLH (keyhole limpet hemocyanin) is produced for use as the antigen.

The animal immunized with an antigen may be any animal, so long as a hybridoma can be prepared, and mouse, rat, hamster, chicken, rabbit or the like is preferably used. Also, the antibody of the present invention includes an antibody produced by a hybridoma obtained by fusing a myeloma cell with the cell having antibody-producing activity derived from such an animal after in vitro immunization.

(3) Preparation of Myeloma Cells

Established cell lines derived from mouse are used as myeloma cells. Examples include 8-azaguanine-resistant murine myeloma cell line (derived from BALB/c) P3-X63Ag8-U1 (P3-U1) [*Current Topics in Microbiology and Immunology*, 18, 1 (1978)], P3-NS1/1-Ag41 (NS-1) [*European J. Immunology*, 6, 511 (1976)], SP2/0-Ag14 (SP-2) [*Nature*, 276, 269 (1978)], P3-X63-Ag8653 (653)[*J. Immunology*, 123, 1548 (1979)], P3-X63-Ag8 (X63) [*Nature*, 256, 495 (1975)] and the like.

The myeloma cells are subcultured in a normal medium [RPMI1640 medium containing glutamine, 2-mercaptoethanol, gentamicin, FBS and 8-azaguanine]. The cells are transferred in the normal medium 3 or 4 days before cell fusion to ensure the cell number of $2 \times 10^7$ or more on the day for fusion.

(4) Cell Fusion and Preparation of Monoclonal Antibody-Producing Hybridomas

A hybridoma can be produced by fusing the antibody-producing cells for fusion obtained in step (2) and the myeloma cells obtained in step (3) using polyethylene glycol 1500.

After the culturing, a portion of the culture supernatant is sampled and subjected to hybridoma screening method such as dot-blotting and binding assay to identify the cell population producing antibodies which is reactive to Aβ oligomers and not to Aβ monomers as described below. Then, cloning is carried out twice by a limiting dilution method [HT medium (HAT medium without aminopterin) is used in the first round, and the normal medium is used in the second round], and a hybridoma which stably shows a high antibody titer is selected as the monoclonal antibody-producing hybridoma.

(5) Preparation of Purified Monoclonal Antibodies

The hybridoma cells producing a monoclonal antibody obtained by step (4) are administered by intraperitoneal injection into 8- to 10-week-old mice or nude mice which is pretreated with pristane (0.5 mL of 2,6,10,14-tetramethylpentadecane (pristane) is intraperitoneally administered, followed by feeding for 2 weeks).

The hybridoma forms ascites tumor in 10 to 21 days. The ascitic fluid is collected from the mice, centrifuged to remove solids, subjected to salting out with 40 to 50% ammonium sulfate and then precipitated by caprylic acid, passed through a DEAE-Sepharose column, a protein A column or a gel filtration column to collect IgG or IgM fractions as purified monoclonal antibodies.

(6) Selection of Monoclonal Antibodies

As a method of screening the antibody, it is possible to exemplify a method of selecting the antibody using a binding activity of the antibody to an Aβ oligomer as an index.

The binding activity of the antibody of the present invention against the antigen (Aβ oligomer) can be analyzed using at least one of the methods such as absorbance measurement method, enzyme linked immunosorbent assay method (dot blot method, ELISA), enzyme immunoassay method (EIA), radioimmunoassay method (RIA), immunofluorescence method and Biacore (Biacore Life Science) using the surface plasmon resonance method (SPR method).

Specifically, the binding of the anti-Aβ oligomer monoclonal antibody to the Aβ oligomer can be determined by the dot blot method in which 2.5 µl of Aβ1-42 (2.5 µg/dot) is pre-incubated for 18 hours, followed by being immobilized on a nitrocellulose membrane. After blocking the non-specific binding site on the membrane with phosphate buffer solution containing 5% of reduced-fat milk, 1% of BSA and 0.05% of Tween-20, the membrane is incubated with culture supernatant, and thereby the Aβ oligomer binding antibody in the culture supernatant can be detected by horseradish peroxidase labelled goat anti-mouse F(ab')$_2$ (1:3000; Amersham) using an enhanced chemiluminescence (ECL) kit and LAS3000mini (Fujitsu, Tokyo, Japan) (WO 2009/051220).

The ELISA is carried out by immobilizing the antibody onto a plate, adding an antigen against the antibody onto the plate, and adding a sample containing desirable antibodies such as the culture supernatant of the cells producing the antibody and the purified antibody. Next, a secondary antibody which recognizes the primary antibody and is tagged added thereto by an enzyme such as alkaline phosphatase is added thereto, and the plate is incubated. After washing, an enzyme substrate such as p-nitrophenylphosphate is added to the plate and the absorbance is measured to evaluate the antigen binding ability of the target sample.

In addition, the reactivity of the antibody can also be determined by using the sandwich enzyme linked immunosorbent assay using chemiluminescence (chemiluminescence-ELISA) in order to specifically detect Aβ oligomers and not to detect Aβ monomers in the present invention (WO 2009/051220).

In addition, in order to evaluate the effectiveness of the monoclonal antibody which has been administered to the periphery of a mouse in vivo, HRP-labelled 6E10 (Senetek PLC, Napa, Calif., USA) human-specific oligomer ELISA can be carried out for Aβ oligomer analysis of plasma and organ collected from the administered mouse in the present invention (WO 2009/051220).

Moreover, it is possible to determined whether the anti-Aβ oligomer humanized antibody of the present invention can bind to Aβ oligomers in AD brains by performing the immunoprecipitation experiment (Ghiso J, et al.: *Biochem J*, 1993) with an amyloid fraction (Matsubara E, et al.: *Neurobiol Aging*, 2004) containing a large amount of Aβ oligomers (WO 2009/051220).

(7) Evaluation of Anti-Aβ Oligomer Antibody Activity

In the present invention, it is possible to determine that the anti-Aβ oligomer antibody specifically binds to Aβ oligomers and has a cytoprotective activity by Aβ incubation for Thioflavin (ThT) assay, Aβ-induced neurotoxicity assay, and measurement of the reactivity against Aβ oligomers with plural molecule sizes fractionated by ultrafiltration and gel filtration, all of which are disclosed in Yamamoto N, et al.: *J. Biol. Chem.*, 282:2646-2655, 2007 or WO 2009/051220.

Furthermore, the Aβ amyloid fiber formation suppressing activity can be determined using ThT assay and electron microscope analysis.

In the present invention, the Aβ oligomer-trapping ability of both the antibodies in AD brains can be measured by determining the existence of SDS-stable 4-, 5-, 8-, 12-mer in immunoprecipitation using the anti-Aβ oligomer humanized antibody.

Moreover, in the present invention, examples of a method for determining the ability for the prophylaxis of the AD-like pathogenesis in an APPswe-transgenic mouse (Tg2576) include a method in which the humanized antibody of the present invention is administered to the mouse to examine whether or not the AD-like pathogenesis such as memory disorder, neuritic plaque lesions, synapse dysfunction and Aβ accumulation can be prevented (WO 2009/051220).

2. Preparation of Recombinant Antibody

The method for producing a transformant to stably express a recombinant antibody and the recombinant antibody can be carried out as below.

(1) Construction of Vector for Expression of Recombinant Antibody

A vector for expression of recombinant antibody is an expression vector for animal cell into which DNAs encoding CH and CL of a human antibody have been inserted, and is constructed by cloning each of DNAs encoding CH and CL of a human antibody into an expression vector for animal cell.

The C region of a human antibody may be CH and CL of any human antibody. Examples include CH belonging to γ1 subclass, CL belonging to κ class, and the like. As the DNAs encoding CH and CL of a human antibody, a chromosomal DNA comprising an exon and an intron or cDNA can be used.

As the expression vector for animal cell, any expression vector can be used, so long as a gene encoding the C region of a human antibody can be inserted thereinto and expressed therein. Examples include pAGE107 [*Cytotechnol.*, 3, 133 (1990)], pAGE103 [*J. Biochem.*, 101, 1307 (1987)], pHSG274 [*Gene*, 27, 223 (1984)], pKCR [*Proc. Natl. Acad. Sci. USA*, 78, 1527 (1981)], pSG1bd2-4 [*Cytotechnol.*, 4, 173 (1990)], pSE1UK1Sed1-3 [*Cytotechnol.*, 13, 79 (1993)] and the like.

Examples of a promoter and enhancer used for an expression vector for animal cell include an SV40 early promoter [*J. Biochem.*, 101, 1307 (1987)], a Moloney mouse leukemia virus LTR [*Biochem. Biophys. Res. Commun.*, 149, 960 (1987)], an immunoglobulin H chain promoter [*Cell*, 41, 479 (1985)] and enhancer [*Cell*, 33, 717 (1983)] and the like.

The vector for expression of recombinant antibody may be either of a type in which a gene encoding an antibody H chain and a gene encoding an antibody L chain exist on separate vectors or of a type in which both genes exist on the same vector (tandem type). In respect of easiness of construction of a vector for expression of recombinant antibody, easiness of introduction into animal cells, and balance between the expression amounts of antibody H and L chains in animal cells, a tandem type of the vector for expression of recombinant antibody is more preferred [*J. Immunol. Methods*, 167, 271 (1994)].

Examples of the tandem type of the vector for expression of recombinant antibody include pKANTEX93 (WO 97/10354), pEE18 [*Hybridoma*, 17, 559 (1998)], and the like.

(2) Preparation of cDNA Encoding V Region of Antibody Derived from Non-Human Animal and Analysis of Amino Acid Sequence mRNA is extracted from hybridoma cells producing an antibody derived from a non-human animal to synthesize cDNA. The synthesized cDNA is cloned into a vector and the sequence analysis using a DNA sequencer is carried out to determine the nucleotide sequences encoding VH and VL.

Whether the obtained cDNAs encode the full amino acid sequences of VL and

VL of the antibody containing a secretory signal sequence can be confirmed by estimating the full length of the amino acid sequences of VH and VL from the determined nucleotide sequence and comparing them with the full length of the amino acid sequences of VH and VL of known antibodies [*Sequences of Proteins of Immunological Interest*, US Dept. Health and Human Services (1991)].

The length of the secretory signal sequence and N-terminal amino acid sequence can be deduced by comparing the full length of the amino acid sequences of VH and VL of the antibody comprising a secretory signal sequence with full length of the amino acid sequences of VH and VL of known antibodies [*Sequences of Proteins of Immunological Interest*, US Dept. Health and Human Services (1991)], and the subgroup to which they belong can also be known.

Furthermore, the amino acid sequence of each of CDRs of VH and VL can be found by comparing the obtained amino acid sequences with amino acid sequences of VH and VL of known antibodies [*Sequences of Proteins of Immunological Interest*, US Dept. Health and Human Services (1991)].

(3) Construction of Vector for Expression of Human Chimeric Antibody cDNAs encoding VH and VL of antibody of non-human animal are cloned in the upstream of genes encoding CH or CL of human antibody of vector for expression of recombinant antibody mentioned in the above (1) to thereby construct a vector for expression of human chimeric antibody.

For example, cDNAs encoding VH and VL are designed and constructed to comprise the linker sequences encoding appropriate amino acids and having appropriate recognition sites of restriction enzyme so as to produce a connection between the 3'-end of a cDNA of VH or VL derived from a non-human animal antibody and the 5'-end of CH or CL derived from a human antibody.

The resultant each cDNA encoding VH and VL is cloned so that each of them is expressed in an appropriate form in the upstream of gene encoding CH or CL of human antibody of the vector for expression of humanized antibody mentioned in the above (1) to construct a vector for expression of human chimeric antibody.

In addition, cDNA encoding VH or VL of non-human animal is amplified by PCR using a synthetic DNA having a recognition sequence of an appropriate restriction enzyme at both terminals and each of them is cloned to the vector for expression of recombinant antibody mentioned in the above (1).

(4) Construction of cDNA Encoding V Region of Humanized Antibody cDNAs encoding VH or VL of a humanized antibody can be obtained as follows.

First, amino acid sequences of framework region (hereinafter referred to as "FR") in VH or VL of a human antibody to which amino acid sequences of CDRs in VH or VL of an antibody derived from a non-human animal antibody are transplanted are selected. Any amino acid sequences of FR in VH or VL of a human antibody can be used, so long as they are from human.

Examples include amino acid sequences of FRs in VH or VL of human antibodies registered in database such as Protein Data Bank, and amino acid sequences common to subgroups of FRs in VH or VL of human antibodies [*Sequences of Proteins of Immunological Interest*, US Dept. Health and Human Services (1991)], and the like.

In order to inhibit the binding activity of the antibody, amino acid sequences having high homology (at least 60% or more) with the amino acid sequence of FR in VH or VL of the original antibody is selected.

Then, amino acid sequences of CDRs of VH or VL of the original antibody are grafted to the selected amino acid sequence of FR in VH or VL of the human antibody, respectively, to design each amino acid sequence of VH or VL of a humanized antibody.

The designed amino acid sequences are converted to DNA sequences by considering the frequency of codon usage found in nucleotide sequences of genes of antibodies [*Sequence of Proteins of Immunological Interest*, US Dept. Health and Human Services (1991)], and the DNA sequence encoding the amino acid sequence of VH or VL of a humanized antibody is designed.

(5) Modification of Amino Acid Sequence of V Region of Humanized Antibody

It is known that when a humanized antibody is produced by simply grafting only CDRs in VH and VL of an antibody derived from a non-human animal into FRs of VH and VL of a human antibody, its antigen binding activity is lower than that of the original antibody derived from a non-human animal [*BIO/TECHNOLOGY*, 9, 266 (1991)].

In humanized antibodies, among the amino acid sequences of FRs in VH and VL of a human antibody, amino acid residues which directly relate to binding to an antigen, amino acid residues which interact with an amino acid residue in CDR, and amino acid residues which maintain the three-dimensional structure of an antibody and indirectly relate to binding to an antigen are identified and modified to amino acid residues which are found in the original non-human antibody to thereby increase the antigen binding activity which has been decreased.

In order to identify the amino acid residues relating to the antigen binding activity in FR, the three-dimensional structure of an antibody is constructed for analysis by X-ray crystallography [*J. Mol. Biol.*, 112, 535 (1977)], computer-modeling [*Protein Engineering*, 7, 1501 (1994)] or the like.

In addition, a modified humanized antibody having appropriate antigen-binding activity can be identified by repetition of various attempts for producing several kinds of modification of each antibody and examining the correlation between each of the modified antibodies and its antigen binding activity.

The modification of the amino acid sequence of FR in VH and VL of a human antibody can be accomplished using various synthetic DNA for modification by PCR as described in (4). The nucleotide sequence of the amplified product by the PCR is determined according to the method as described in (2) so as to confirm the intended modification has been occurred.

(6) Construction of Vector for Expression of Humanized Antibody

A vector for expression of humanized antibody can be constructed by cloning each cDNA encoding VH or VL of a constructed recombinant antibody into upstream of each gene encoding CH or CL of the human antibody in the vector for expression of recombinant antibody as described in (1).

For example, recognition sequences of appropriate restriction enzymes are introduced into the 5'-end of synthetic DNAs positioned at both ends among synthetic DNAs used for the construction of VH or VL of the humanized antibody in (4) and (5) to enable to clone the VH or VL in the upstream of each gene encoding CH or CL of the human antibody in the expression vector for humanized antibody as described in the above (1), so as to express them as an appropriate form.

(7) Transient Expression of Recombinant Antibody

In order to efficiently evaluate the antigen binding activity of various humanized antibodies produced, the recombinant antibodies can be expressed transiently using the vector for expression of recombinant antibody as described in (3) and (6) or the modified expression vector thereof.

Any cell can be used as a host cell for introduction of the expression vector, so long as the host cell can express a recombinant antibody. Generally, COS-7 cell (ATCC CRL1651) is used [*Methods in Nucleic Acids Res.*, CRC Press, 283 (1991)]. Examples of the method for introducing the expression vector into COS-7 cell include a DEAE-dextran method [*Methods in Nucleic Acids Res.*, CRC Press, 283 (1991)], a lipofection method [*Proc. Natl. Acad. Sci. USA*, 84, 7413 (1987)], and the like.

(8) Establishment of Transformant which Stably Expresses Recombinant Antibody and Preparation of Recombinant Antibody A transformant which stably expresses a recombinant antibody can be obtained by introducing the vector for expression of recombinant antibody described in (3) and (6) into an appropriate host cell.

Examples of the method for introducing the expression vector into a host cell include electroporation [Japanese Published Unexamined Patent Application No. 257891/90, *Cytotechnology*, 3, 133 (1990)] and the like.

As the host cell into which a vector for expression of a recombinant antibody is introduced, any cell can be used, so long as it is a host cell which can express the recombinant antibody. Examples include CHO-K1 (ATCC CCL-61), DUKXB11 (ATCC CCL-9096), Pro-5 (ATCC CCL-1781), CHO-S (Life Technologies, Cat. No. 11619), rat YB2/3HL.P2.G11.16Ag.20 cell (also referred to as YB2/0; ATCC CRL1662), murine myeloma NS0, murine myeloma SP2/0-Ag14 cell (ATCC CRL1581), murine P3X63-Ag8.653 cell (ATCC CRL1580), CHO cell in which a dihydrofolate reductase gene (hereinafter referred to as "dhfr") is deficient [*Proc. Natl. Acad. Sci. U.S.A.*, 77.4216 (1980)], lectin resistant line Lec13 [*Somatic Cell and Molecular genetics*, 12, 55 (1986)], CHO cell in which α1,6-fucosyltransaferse gene is deficient (WO 2005/35586, WO 02/31140), and the like.

In addition, host cells in which activity of a protein such as an enzyme relating to synthesis of an intracellular sugar nucleotide, GDP-fucose, a protein such as an enzyme relating to the modification of a sugar chain in which 1-position of fucose is bound to 6-position of N-acetylglucosamine in the reducing end through α-bond in a complex type N-glycoside-linked sugar chain, or a protein relating to transport of an intracellular sugar nucleotide, GDP-fucose, to the Golgi body are introduced is decreased or deleted, such as CHO cell in which α1,6-fucosyltransferase gene is defected as described in WO05/35586, WO02/31140, can also be used.

After introduction of the expression vector, transformants which stably express a recombinant antibody are selected by culturing in a medium for animal cell culture containing an agent such as G418 sulfate (hereinafter referred to as "G418") (Japanese Published Unexamined Patent Application No. 257891/90).

Examples of the medium for animal cell culture include RPMI1640 medium (manufactured by Invitrogen), GIT medium (manufactured by Nihon Pharmaceutical), EX-CELL301 medium (manufactured by JRH), IMDM medium (manufactured by Invitrogen), Hybridoma-SFM medium (manufactured by Invitrogen), a derivative medium thereof containing various additives such as FBS.

The recombinant antibody can be produced and accumulated in a culture supernatant by culturing the selected transformants in a medium. The expression amount and the antigen binding activity of the recombinant antibody in the culture supernatant can be measured by ELISA or the like.

Also, in the transformant, the expression amount of the recombinant antibody can be increased by using DHFR amplification system or the like according to the method disclosed in Japanese Published Unexamined Patent Application No. 257891/90.

The recombinant antibody can be purified from the culture supernatant of the transformant by protein A column [*Monoclonal Antibodies-Principles and practice*, Third edition, Academic Press (1996), *Antibodies—A Laboratory Manual*, Cold Spring Harbor Laboratory (1988)].

For example, the recombinant antibody can be purified by a combination of gel filtration, ion-exchange chromatography, ultrafiltration and the like.

The molecular weight of the H chain or the L chain of the purified recombinant antibody or the antibody molecule as a whole is determined by polyacrylamide gel electrophoresis (hereinafter referred to as "SDS-PAGE") [*Nature*, 227, 680 (1970)], Western blotting [*Monoclonal Antibodies-Principles and practice*, Third edition, Academic Press (1996), *Antibodies—A Laboratory Manual*, Cold Spring Harbor Laboratory (1988)], and the like.

3. Method of Controlling Effector Activity of Antibody

As a method for controlling an effector activity of the anti-Aβ oligomer humanized antibody of the present invention, a method for controlling an amount of fucose (hereinafter, referred to also as "core fucose") which is bound in α-1,6 linkage to N-acetylglucosamine (GlcNAc) present in a reducing end of a complex type N-linked sugar chain which is bound to asparagine (Asn) at position 297 of an Fc region of an antibody (WO2005/035586, WO2002/31140, and WO00/61739), a method for controlling an effector activity of a monoclonal antibody by modifying amino acid group(s) of an Fc region of the antibody, a method for engineering a subclass of the antibody, and the like are known. The effector activity of the anti-Aβ oligomer humanized antibody of the present invention can be controlled by using any of the methods.

The "effector activity" means an antibody-dependent activity which is induced via an Fc region of an antibody. As the effector activity, an antibody-dependent cellular cytotoxicity (ADCC activity), a complement-dependent cytotoxicity (CDC activity), an antibody-dependent phagocytosis (ADP activity) by phagocytic cells such as macrophages and dendritic cells, and the like are known.

By controlling a content of core fucose of a complex type N-linked sugar chain of Fc of an antibody, an effector activity of the antibody can be increased or decreased. As a method for reducing a content of fucose which is bound to a complex type N-linked sugar chain bound to Fc of the antibody, an antibody to which fucose is not bound can be obtained by the expression of an antibody using a CHO cell which is deficient in a gene encoding α1,6-fucosyltransferase. The antibody to which fucose is not bound has a high ADCC activity.

On the other hand, according to a method for increasing a content of fucose which is bound to a complex type N-linked sugar chain bound to Fc of an antibody, an antibody to which fucose is bound can be obtained by the expression of an antibody using a host cell into which a gene encoding α1,6-fucosyltransferase is introduced. The antibody to which fucose is bound has a lower ADCC activity than the antibody to which fucose is not bound.

Further, by modifying amino acid residue(s) in an Fc region of an antibody, the ADCC activity or CDC activity can be increased or decreased. For example, the CDC activity of an antibody can be increased by using the amino acid sequence of the Fc region described in US2007/0148165. Further, the ADCC activity or CDC activity can be increased or decreased by modifying the amino acid as described in U.S. Pat. Nos. 6,737,056, or 7,297,775 or 7,317,091.

In addition, it is known that among human IgG subclass, the effector activity of IgG2 and IgG4 subclasses is lower than those of IgG1 and IgG3 subclasses. Therefore, the antibody having a lower effector activity can be prepared by replacing Fc region with that of the antibody subclass having a lower effector activity.

With regard to the stabilization of an antibody of IgG2 and IgG4 subclasses, stable IgG2 or IgG4 antibody in which an effector activity is controlled can be prepared using a methods described in WO2006/075668, WO2006/035586 and the like.

Moreover, it is possible to obtain an antibody in which the effector activity of the antibody has been controlled, by using the combination of the above-mentioned methods for one antibody.

4. Treatment Method Using Anti-Aβ Oligomer Antibody of the Present Invention

It has been suggested that the decline in memory accompanying AD relates to the synapse dysfunction caused by soluble Aβ oligomers [Klein W L., 2001. *Trends Neurosci*; Selkoe D J. 2002, *Science*]. Accordingly, there is a possibility that excessive accumulation and deposition of Aβ oligomers triggers a complex downstream cascade which results in AD.

In the present invention, the treatment does not necessarily have perfect treatment effects or preventive effects on the organ and the tissue which show the symptoms due to the disorder or disease but may provide a part of these effects.

The treatment of AD in the present invention means improving at least one symptom which may occur due to AD. Examples include the improvement or suppression of the cognitive dysfunction, the improvement or the suppression of the neuritic plaque formation, the improvement or the suppression of synapse dysfunction, and the decrease and the suppression of Aβ accumulation in brain tissues, blood, or the like.

Here, the cognitive dysfunction includes, for example, impaired long-term/short-term memory, impaired object recognition memory, impaired spatial memory, and impaired emotional memory.

In addition, as a therapeutic method using the anti-Aβ oligomer humanized antibody of the present invention, examples include a method for suppressing the cognitive dysfunction, a method for suppressing AD, a method for suppressing the progression of AD, a method for suppressing the neuritic plaque formation, a method for suppressing the Aβ accumulation, a method for neutralizing (suppressing) the neurotoxicity activity, a method for inhibiting Aβ amyloid fiber formation, and a method for neutralizing (suppressing) the synapse toxicity activity.

Furthermore, examples of other configurations include a method for at least one of the prevention and the treatment of cognitive dysfunction and a method for at least one of the prevention and the treatment of AD.

The therapeutic agent comprising the monoclonal antibody or antibody fragment of the present invention or derivatives thereof may consist of only the antibody or antibody fragment or derivatives thereof as an active ingredient, and is preferably supplied as a pharmaceutical formulation produced by an appropriate method well known in the technical field of pharmaceutics, by mixing it with one or more pharmaceutically acceptable carriers.

Examples of a route of administration include oral administration and parenteral administration, such as buccal, tracheal, rectal, subcutaneous, intramuscular or intravenous administration.

Examples of the dosage form includes sprays, capsules, tablets, powder, granules, syrups, emulsions, suppositories, injections, ointments, tapes and the like.

The pharmaceutical preparation suitable for oral administration includes emulsions, syrups, capsules, tablets, powders, granules and the like.

Liquid preparations such as emulsions and syrups can be produced using, as additives, water; sugars such as sucrose, sorbitol and fructose; glycols such as polyethylene glycol and propylene glycol; oils such as sesame oil, olive oil and soybean oil; antiseptics such as p-hydroxybenzoic acid esters; flavors such as strawberry flavor and peppermint; and the like.

Capsules, tablets, powders, granules and the like can be produced using, as additives, excipients such as lactose, glucose, sucrose and mannitol; disintegrating agents such as starch and sodium alginate; lubricants such as magnesium stearate and talc; binders such as polyvinyl alcohol, hydroxypropylcellulose and gelatin; surfactants such as fatty acid ester; plasticizers such as glycerin; and the like.

The pharmaceutical preparation suitable for parenteral administration includes injections, suppositories, sprays and the like.

Injections can be prepared using a carrier such as a salt solution, a glucose solution and a mixture of both thereof.

Suppositories can be prepared using a carrier such as cacao butter, hydrogenated fat or carboxylic acid.

Sprays can be prepared using the antibody or antibody fragment of the present invention as such or using it together with a carrier which does not stimulate the buccal or airway mucous membrane of the patient and can facilitate absorption of the compound by dispersing it as fine particles.

The carrier includes lactose, glycerol and the like. It is possible to produce pharmaceutical preparations such as aerosols and dry powders.

In addition, the components exemplified as additives for oral preparations can also be added to the parenteral preparations.

EXAMPLE 1

Preparation of Anti-Aβ Oligomer Humanized Antibody
(1) Design of Amino Acid Sequences for VH and VL of Anti-Aβ Oligomer Humanized Antibody 6E4

The amino acid sequence of the VH of the anti-Aβ oligomer humanized antibody 6E4 was designed as follows.

First, the CDR sequence of the amino acid sequence (SEQ ID NO:8) was determined as the VH of the anti-AD oligomer mouse monoclonal antibody 6E4 antibody which was prepared in the reference example, based on the report by Kabat, et al. [*Sequences of Proteins of Immunological Interest*, US Dept. Health and Human Services (1991)]. As a result, the amino acid sequences of the CDRs 1 to 3 of the VH were set to be the ones represented by SEQ ID NOs: 1 to 3.

Then, an amino acid sequence of the anti-Aβ oligomer oligomer 6E4 humanized antibody was designed as follows. In order to implant the amino acid sequences (SEQ ID NOs: 1 to 3) of the CDRs 1 to 3 of the VH, the amino acid sequence of the FR of the VH in the humanized antibody was selected.

Kabat, et al. have classified VHs of the various known human antibodies into subgroups (HSG I to III) based on the homologies of their amino acid sequences, and have reported the common sequences for each of the subgroups [*Sequences of Proteins of Immunological Interest*, US Dept. Health and Human Services (1991)].

Thus, the homologies between the amino acid sequences of the FRs of the common sequences in the subgroups Ito III of the VH of the human antibody and the amino acid sequences of the FRs of 6E4VH were searched. As a result of searching the homologies, the homologies of HSGI, HSGII and HSGIII were 75.9%, 54.0% and 57.5%, respectively. Accordingly, the amino acid sequence of the FR of 6E4VH had the highest homology with the subgroup I.

Based on the above result, each of the amino acid sequences (SEQ ID NOs:1 to 3) of the CDRs of 6E4VH were grafted at appropriate positions in the amino acid sequence of the FR of the common sequence in the subgroup I of the VH of the human antibody. Accordingly, the amino acid sequence 6E4HV0 (SEQ ID NO:12) of the VH of the anti-Aβ oligomer 6E4 humanized antibody was designed.

Next, in the same manner as the H chain, the sequences of the CDRs 1 to 3 of the amino acid sequence (SEQ ID NO:10) of the VL were decided as the amino acid sequences of SEQ ID NOs:4 to 6, respectively, and the amino acid sequence of the VL of the anti-AD oligomer 6E4 humanized antibody was designed as follows.

In order to graft the amino acid sequences (SEQ ID NOs:4 to 6) of the CDRs 1 to 3 of the VL of the 6E4 antibody, respectively, the amino acid sequence of the FR of the VL in the human antibody was selected.

Kabat, et al. have classified VLs of the various known human antibodies into subgroups (HSG I to IV) based on the homologies of their amino acid sequences, and have reported the common sequences for each of the subgroups [*Sequences of Proteins of Immunological Interest*, US Dept. Health and Human Services (1991)].

Thus, the homologies between the amino acid sequences of the FRs of the common sequences in the subgroups Ito IV of the VL of the human antibody and the amino acid sequences of the FRs of 6E4VL were searched. As a result of searching the homologies, the homologies of HSGI, HSGII, HSGIII, and HSGIV were 67.5%, 86.3%, 68.8%, and 76.3%, respectively. Accordingly, the amino acid sequence of the FR of 6E4VL had the highest homology with the subgroup II.

Based on the above result, each of the amino acid sequences (SEQ ID NOs:4 to 6) of the CDRs of 6E4VL were grafted at appropriate positions in the amino acid sequence of the FR of the common sequence in the subgroup II of the VL of the human antibody.

However, Leu at position 110 of the amino acid sequence (SEQ ID NO:10) of 6E4VL is not the amino acid residue which is used most frequently but the amino acid residue which is used with relatively high frequency at the corresponding sites in the amino acid sequences of the FRs of the human antibodies exemplified by Kabat, et al.

Accordingly, the amino acid residue seen in the amino acid sequence of the above 6E4 was employed. As described above, the amino acid sequence (SEQ ID NO:14) of the VL of the anti-Aβ oligomer 6E4 humanized antibody, 6E4LV0, was designed.

The designed amino acid sequence 6E4HV0 of the VH and amino acid sequence 6E4LV0 of the VL in the anti-A13 oligomer 6E4 humanized antibody are the sequences constructed by grafting only the amino acid sequences of the CDRs of an anti-Aβ oligomer mouse monoclonal antibody 6E4 to the amino acid sequence of the selected FR of the human antibody.

In general, however, in the construction of a humanized antibody, the binding activity is reduced in many cases where the amino acid sequences of the CDRs of the mouse antibody is simply implanted to the FR of the human antibody.

For this reason, in order to prevent the decrease in binding activity, the modification of the amino acid residues that is considered to affect the binding activity among the amino acid residues that are located in the FRs of the human antibody and different from those of the mouse antibody is carried out together with the graft of the amino acid sequences of the CDRs.

Thus, in this Example, the amino acid residues of the FR, which are considered to affect the binding activity, were identified in the following manner.

First, the three-dimensional structure of an antibody V region (hereinafter, referred to as an HV0LV0) comprising the amino acid sequence 6E4HV0 of the VH and the amino acid sequence 6E4LV0 of the VL in the anti-Aβ oligomer 6E4 humanized antibody designed as described above was constructed using a computer modeling technique.

The construction of the three-dimensional structure coordinates and the display of the three-dimensional structure were carried out using Discovery Studio (Accelrys, Inc.) in accordance with the instructions attached thereto. The computer model of the three-dimensional structure of the V region in the anti-Aβ oligomer mouse monoclonal antibody 6E4 was also constructed in the same manner.

Furthermore, the amino acid residues which were different from that in 6E4 were selected among the amino acid sequences of the FR in the VH and the VL of HV0LV0, the amino acid sequence with the modification to the amino acid residues of 6E4 was prepared, and the three-dimensional structure model was constructed in the same manner.

These resultant three-dimensional structures of the V regions in 6E4, HV0LV0 and the modified forms were compared, and the amino acid residues which were considered to affect the binding activity of the antibody were identified.

As a result, as the amino acid residues which are considered to change the three-dimensional structure of the antigen binding sites and affect the binding activity of the antibody among the amino acid residues of the FRs in HV0LV0, Lys at position 12, Val at position 20, Arg at position 38, Gln at position 39, Leu at position 45, Met at position 48, Arg at position 67, Val at position 68, Ile at position 70, Ala at position 72, Thr at position 74 and Ala at position 97 in the amino acid sequence represented by SEQ ID NO:12 in 6E4HV0 and Ile at position 2, Pro at position 15, Gln at position 50 and Tyr at position 92 in 6E4LV0 were selected, respectively.

At least one amino acid sequence among these selected amino acid residues were modified to the amino acid residue which existed at the same site in 6E4, and thereby VH and VL of the humanized antibody which comprises an amino acid sequence comprising various modifications were designed.

Specifically, in the VH, at least one modification among the amino acid modifications in which Lys at position 12 was substituted with Val, Val at position 20 was substituted with Leu, Arg at position 38 was substituted with Lys, Gln at position 39 was substituted with Leu, Leu at position 45 was substituted with Phe, Met at position 48 was substituted with Ile, Arg at position 67 was substituted with Lys, Val at position 68 was substituted with Ala, Ile at position 70 was substituted with Leu, Ala at position 72 was substituted with Val, Thr at position 74 was substituted with Lys and Ala at position 97 was substituted with Thr in the amino acid sequence represented by SEQ ID NO:12 was introduced.

In addition, in the VL, at least one modification was introduced among the amino acid modifications in which Ile at position 2 was substituted with Val, Pro at position 15 was substituted with Leu, Gln at position 50 was substituted with Lys, and Tyr at position 92 was substituted with Phe in the amino acid sequence represented by SEQ ID NO:14.

As the antibody V region of the anti-Aβ oligomer 6E4 humanized antibody in which at least one amino acid residue in FR of HV0LV0 was modified, HV0LV0, HV0LV2a, HV0LV2b, HV0LV2c, HV0LV2d, HV0LV3, HV0LV4, HV2LV0, HV2LV2a, HV2LV2b, HV2LV2c, HV2LV2d, HV2LV3, HV2LV4, HV3LV0, HV3LV2a, HV3LV2b, HV3LV2c, HV3LV2d, HV3LV3, HV3LV4, HV4LV0, HV4LV2a, HV4LV2b, HV4LV2c, HV4LV2d, HV4LV3, HV4LV4, HV5LV0, HV5LV2a, HV5LV2b, HV5LV2c, HV5LV2d, HV5LV3, HV5LV4, HV7aLV0, HV7aLV2a, HV7aLV2b, HV7aLV2c, HV7aLV2d, HV7aLV3, HV7aLV4, HV7bLV0, HV7bLV2a, HV7bLV2b, HV7bLV2c, HV7bLV2d, HV7bLV3, HV7bLV4, HV9LV0, HV9LV2a, HV9LV2b, HV9LV2c, HV9LV2d, HV9LV3, HV9LV4, HV12LV0, HV12LV2a, HV12LV2b, HV12LV2c, HV12LV2d, HV12LV3 and HV12LV4 were designed.

FIG. 1 and FIG. 2 show the amino acid sequences of H chain variable regions HV2, HV3, HV4, HV5, HV7a, HV7b, HV9 and HV12, respectively, and the amino acid sequences of L chain variable regions LV2a, LV2b, LV2c, LV2d, LV3 and LV4, respectively.

(2) Production Anti-Aβ Oligomer Humanized Antibody

The DNA encoding the amino acid sequence in the variable region of the anti-Aβ oligomer humanized antibody was designed with the codons used in the DNAs (SEQ ID NOs:7 and 9) encoding the amino acid sequences of 6E4VH and 6E4VL. In the amino acid modification, the DNA was designed with the codons frequently used in mammalian cells.

The DNA sequences encoding the amino acid sequences of 6E4HV0 and 6E4LV0 in the anti-Aβ oligomer 6E4 humanized antibody are shown as SEQ ID NOs:11 and 13, respectively. In addition, the codons used in the DNAs encoding the amino acid sequences of 6E4VH and 6E4VL was used for designing the variable region with the amino acid modification.

Using these DNA sequences, the expression vector of the humanized antibody was constructed, and the humanized antibody was expressed.

(3) Construction of cDNA Encoding VH of Anti-Aβ Oligomer Humanized Antibody

The cDNA encoding the amino acid sequence 6E4HV0 of the VH in the anti-Aβ oligomer humanized antibody shown as SEQ ID NO:12, which had been designed in the above (1), and HV12 shown in FIG. 1, which had been designed in the above method (2) were produced by total chemical synthesis.

(4) Construction of cDNA Encoding VL of Anti-Aβ Oligomer Humanized Antibody

The cDNA encoding the amino acid sequence 6E4LV0 of the VL in the anti-Aβ oligomer humanized antibody shown as SEQ ID NO:14, which had been designed in the above (1), and LV2a and LV4 shown in FIG. 2, which had been designed in the above method (2) were produced by total chemical synthesis.

(5) Construction of Anti-Aβ Oligomer Humanized Antibody Expression Vectors

The cDNA encoding 6E4LV0 or HV12 and the cDNA encoding any one of 6E4LV0, LV2a and LV4 obtained in the above (3) and (4) were inserted into appropriate positions in humanized antibody expression vector pKANTEX93 disclosed in WO 97/10354 to construct various anti-Aβ oligomer humanized antibody expression vectors.

(6) Expression of Anti-Aβ Oligomer Humanized Antibody Using Animal Cells

The expression of the anti-Aβ oligomer humanized antibody in animal cells was carried out by a conventional method [*Antibody Engineering, A Practical Guide*, W. H. Freeman and Company (1992)] using the anti-Aβ oligomer humanized antibody expression vectors obtained in the above (5) to yield the transformant for producing the anti-Aβ oligomer humanized antibody (HV0LV0, HV0LV2a, HV0LV4 and HV12LV4).

As an animal cell line, CHO/D644 cell line derived by double knockout of α1,6-fucosyltransferase (FUT8) gene (hereinafter, referred to as FUT8 knockout CHO cells) was used. It has been known that no fucose is added to the core part of the complex type N-linked sugar chain of the antibody expressed with this host cell strain (WO 2002/31140).

(7) Preparation of Purified Anti-Aβ Oligomer Humanized Antibody

After the transformant obtained in (6) of this example was cultured by a conventional culture method, the cell suspension was collected. Then, the centrifugation was carried out for 20 minutes under the condition of 3000 rpm and 4° C. After collection, the culture supernatant was filter-sterilized with a Millex GV filter having a pore diameter of 0.22 μm.

After filling 0.5 ml of Prosep vA High Capacity (manufactured by Millipore Corporation) into a column with a diameter of 0.8 cm, 5.0 mL of purified water and 5.0 mL of PBS buffer (pH7.4) were subsequently passed thereto to equilibrate the carrier.

Then, after the culture supernatant was passed through the column, the column was washed with 5.0 mL of PBS buffer (pH 7.4). After washing, the antibody adsorbed to the carrier was eluted by 2.0 mL of 0.1 mol/L citrate buffer (pH 5.0), 2.0 mL of 0.1 mol/L citrate buffer (pH 3.5), and 2.0 mL of 0.1 mol/L citrate buffer (pH 3.0) in this order.

The elution was obtained by 500 μL over 4 fractions. Thereafter, SDS-PAGE analysis was performed on the thus obtained purified fractions. The fractions of which the elution of the target protein was detected were collected, and subjected to dialysis over a whole day and night at 4° C. using 150 mmol/L of NaCl and 10 mmol/L of Na citrate solution (pH6.0).

After the dialysis, anti-Aβ oligomer humanized antibody solution was collected and subjected to filter-sterilization using Millex GV (Millipore Corporation) with a pore diameter of 0.22 μm. The absorbance at 280 nm (OD280 nm) was measured using an absorbance measurer (SHIMADZU UV-1700) to calculate the density of the respective purified anti-Aβ oligomer humanized antibodies.

As a result, four types of anti-Aβ oligomer humanized antibody consisting HV0LV0 comprising 6E4HV0 as the VH and 6E4LV0 as the VL of the antibody, HV0LV2a comprising 6E4HV0 as the VH and LV2a as the VL of the antibody, HV0LV4 comprising 6E4HV0 as the VH and LV4 as the VL of the antibody and HV12LV4 comprising HV12 as the VH and LV4 as the VL of the antibody, respectively, were produced.

EXAMPLE 2

Production of Antigen
(1) Preparation of Aβ Oligomers

Amyloid β-protein, Human 1-42 peptide (manufactured by Peptide Institute, Inc.) was dissolved at 1 mmol/L using hexafluoroisopropanol. After sonication for 10 minutes, the prepared solution was dried up in air at room temperature overnight.

Thereafter, 4 μL of dimethylsulfoxide was added thereto, and three-minute sonication was performed. Into the prepared solution, 200 μL of acetic acid solution (pH4.5) was added, and the resulting material was kept overnight in a stationary manner at 4° C. to produce Aβ oligomers.

(2) Preparation of Aβ Monomers

Biotin-beta-Amyloid, Human 1-40 (manufactured by AnaSpec, Inc.) was dissolved at 250 μmol/L using 0.1% of ammonia water. After the prepared solution was subjected to sonication for five minutes, the resultant was centrifuged under the conditions of 16,000 rpm and 4° C. for 60 minutes. Thus, Aβ monomers were prepared by collecting the supernatant.

EXAMPLE 3

Evaluation on Anti-Aβ Oligomer Humanized Antibody Activity (1) Evaluation on Binding Activity of Anti-Aβ Oligomer Humanized Antibody Against Aβ Oligomers Using Biacore In order to analyze the binding activity of each of anti-Aβ oligomer humanized antibodies (HV0LV0, HV0LV2a, HV0LV4 and HV12LV4) against Aβ oligomers in the chemical kinetics manner, the binding activity measurement was carried out using the surface plasmon resonance method (SPR method).

All the following operations were performed using Biocore T100 (manufactured by GE Healthcare Bio-sciences). The Aβ oligomers obtained in (1) of Example 2 were immobilized to the CM5 sensor chip (GE Healthcare Bio-sciences) using the amine coupling method.

Onto the chip to which the Aβ oligomers were immobilized for measurement samples prepared to have 8 levels of density by diluting from 30 μg/mL by doubling dilution in a stepwise manner (HV0LV0, HV0LV2a, HV0LV4 and HV12LV4) was sequentially injected and measured in the order from the lower density based on the automatic program of the multi-kinetics.

Using the analysis software attached to the device, Biacore T100 Evaluation software (manufactured by Biacore Life Science), analysis was carried out with the Bivalent Analyte model to calculate the binding rate constant ka and the dissociation rate constant kd of each of the antibody against Aβ oligomers.

The thus obtained binding rate constant ka1, the dissociation rate constant kd1, and the dissociation constant KD (kd1/ka1) of each of the antibodies are shown in Table 1, respectively.

TABLE 1

| Binding Activity of anti-Aβ oligomer humanized antibody to Aβ oligomers | | | |
| --- | --- | --- | --- |
| Antibody | ka (1/Ms) | kd (1/s) | KD (mol/L) |
| HV0LV0 | $1.7 \times 10^4$ | $6.9 \times 10^{-4}$ | $4.0 \times 10^{-8}$ |
| HV0LV2a | $6.4 \times 10^3$ | $3.9 \times 10^{-4}$ | $6.1 \times 10^{-8}$ |
| HV0LV4 | $7.0 \times 10^3$ | $5.0 \times 10^{-4}$ | $7.1 \times 10^{-8}$ |
| HV12LV4 | $2.7 \times 10^3$ | $8.1 \times 10^{-4}$ | $3.0 \times 10^{-7}$ |

As shown in Table 1, all of the anti-Aβ oligomer humanized antibodies (HV0LV0, HV0LV2a, HV0LV4 and HV12LV4) exhibited binding ability to Aβ oligomers at the affinity from $3 \times 10^{-7}$ to $4 \times 10^{-8}$ mol/L.

(2) Evaluation of Binding Activity of Anti-Aβ Oligomer Humanized Antibody Against Aβ Monomers Using Biacore In order to analyze the binding activity of the respective anti-Aβ oligomer humanized antibodies (HV0LV0, HV0LV2a, HV0LV4 and HV12LV4) against Aβ monomers, the binding activity was measured in the same manner as in (1) of this Example. In addition, the binding activity of anti-Aβ antibody 6E10 (manufactured by CONVANCE) was measured as a control antibody.

The Aβ monomers obtained in (2) of Example (2) were immobilized to the SA sensor chip (manufactured by GE Healthcare Bio-sciences) by the biotin capturing method. Onto the chip to which the Aβ monomers were immobilized, samples for measurement, which were prepared to have 5 levels of density by diluting from 30 μg/mL by doubling dilution in a stepwise manner (6E10, HV0LV0, HV0LV2a, HV0LV4 and HV12LV4), were sequentially injected and measured in the order from the lower density based on the automatic program of the multi-kinetics mode. The sensorgrams are shown in FIG. 3.

As shown in FIG. 3, it has been found that all of four kinds of the anti-AP oligomer humanized antibodies (HV0LV0, HV0LV2a, HV0LV4 and HV12LV4) do not exhibit binding ability to Aβ monomers.

Reference Example
1. Preparation of Antigen

Aβ1-40 peptide was synthesized to produce a compound in which fluorescent isothiocyanate of 6-carboxytetramethyl-rhodamine (6-TAMRA) (SIGMA) was chemically combined to the N-terminal thereof. The polymerization reaction of this compound was carried out with Aβ1-40 peptide (Peptide Institute, Inc), and thereby a preparation (Aβ1-40 oligomers) containing a large amount of oligomers was prepared.

2. Establishment of Antibody-Producing Hybridoma

The antigen prepared in the above-mentioned manner was immunized to the footpad of a Balb-c mouse, and subsequently, six more additional immunizations were carried out. The hybridoma was produced by fusing with Sp2/0-Ag14 cells with the use of the inguinal lymph node using polyethylene glycol 1500.

3. Dot Blot Analysis

The initial screening was performed by the dot blot analysis in which 2.5 μl of Aβ1-42 (2.5 μg/dot) which had been pre-incubated for 18 hours was immobilized on the nitrocellulose membrane. The non-specific binding site on the membrane was blocked with phosphate buffer solution containing 5% of reduced-fat milk, 1% of BSA, and 0.05% of Tween-20, and the non-specific binding site was incubated with culture solution supernatant.

The antibody bound to Aβ oligomer in the culture supernatant was detected by horseradish peroxidase marked goat anti-mouse F(ab')$_2$ (1:3000; Amersham) and depicted by a sensitive chemiluminescence (ECL) kit using LAS3000mini (Fujitsu, Tokyo, Japan). With such an operation, the anti-Aβ oligomer mouse monoclonal antibody 6E4 was established.

The above reference example was disclosed in PCT/JP 2009/52039 (WO 2009/099176).

While the invention has been described in detail and with reference to specific embodiments thereof, it will be apparent to one skill in the art that various changes and modifications can be made therein without departing from the spirit and scope thereof.

This application is based on U.S. provisional application No. 61/232,038, filed on Aug. 7, 2009, the entire contents of which are incorporated hereinto by reference. All references cited herein are incorporated in their entirety.

Free Text in Sequence Listings:
SEQ ID NO:1—Description of artificial sequence; HCDR1 amino acid sequence
SEQ ID NO:2—Description of artificial sequence; HCDR2 amino acid sequence
SEQ ID NO:3—Description of artificial sequence; HCDR3 amino acid sequence
SEQ ID NO:4—Description of artificial sequence; LCDR1 amino acid sequence
SEQ ID NO:5—Description of artificial sequence; LCDR2 amino acid sequence
SEQ ID NO:6—Description of artificial sequence; LCDR3 amino acid sequence
SEQ ID NO:11—Description of artificial sequence; DNA sequence encoding 6E4HV0
SEQ ID NO:12—Description of artificial sequence; amino acid sequence of 6E4HV0 variable region
SEQ ID NO:13—Description of artificial sequence; DNA sequence encoding 6E4LV0 variable region
SEQ ID NO:14—Description of artificial sequence; amino acid sequence of 6E4LV0 variable region
SEQ ID NO:15—Description of artificial sequence; amino acid sequence of HV12 variable region
SEQ ID NO:16—Description of artificial sequence; amino acid sequence of LV2a variable region
SEQ ID NO:17—Description of artificial sequence; amino acid sequence of LV4 variable region

What is claimed is:

1. A DNA which encodes a variable region of an antibody or an antibody fragment thereof, wherein the antibody heavy chain variable region comprises the amino acid sequence of SEQ ID NO: 12 or 15 or the antibody light chain variable region comprises the amino acid sequence of SEQ ID NO: 14, 16 or 17.

2. A recombinant vector which comprises the DNA according to claim 1.

3. A transformant obtainable by introducing the recombinant vector according to claim 2 into a host cell.

4. A process for producing an antibody or antibody fragment thereof, wherein the antibody heavy chain variable region comprises the amino acid sequence of SEQ NO: 12 or 15 and the antibody light chain variable region comprises the amino acid sequence of SEQ ID NO: 14, 16 or 17, comprising culturing the transformant described in claim 3 in a medium to form and accumulate the antibody or the antibody fragment thereof, wherein the antibody heavy chain variable region comprises the amino acid sequence of SEQ ID NO: 12 or 15 and the antibody light chain variable region comprises the amino acid sequence of SEQ ID NO: 14, 16 or 17 in the culture and collecting the antibody or the antibody fragment thereof from the culture.

* * * * *

```
                        SEQUENCE LISTING

<160> NUMBER OF SEQ ID NOS: 17

<210> SEQ ID NO 1
<211> LENGTH: 5
<212> TYPE: PRT
<213> ORGANISM: Artificial
<220> FEATURE:
<223> OTHER INFORMATION: Synthetic construct of HCDR1

<400> SEQUENCE: 1

Ser Tyr Trp Met His
1               5

<210> SEQ ID NO 2
<211> LENGTH: 17
<212> TYPE: PRT
<213> ORGANISM: Artificial
<220> FEATURE:
<223> OTHER INFORMATION: Synthetic construct of HCDR2

<400> SEQUENCE: 2

Glu Ile Asn Pro Arg Asn Gly Gly Thr Asn Asn Asn Glu Asn Phe Lys
1               5                   10                  15

Arg
```

-continued

```
<210> SEQ ID NO 3
<211> LENGTH: 9
<212> TYPE: PRT
<213> ORGANISM: Artificial
<220> FEATURE:
<223> OTHER INFORMATION: Synthetic construct of HCDR3

<400> SEQUENCE: 3

Asp Gly Asn Tyr Asp Pro Phe Ala Tyr
1               5

<210> SEQ ID NO 4
<211> LENGTH: 16
<212> TYPE: PRT
<213> ORGANISM: Artificial
<220> FEATURE:
<223> OTHER INFORMATION: Synthetic construct of LCDR1

<400> SEQUENCE: 4

Arg Ser Ser Gln Ser Leu Val His Ser Asn Gly Asn Thr Tyr Leu His
1               5                   10                  15

<210> SEQ ID NO 5
<211> LENGTH: 7
<212> TYPE: PRT
<213> ORGANISM: Artificial
<220> FEATURE:
<223> OTHER INFORMATION: Synthetic construct of LCDR2

<400> SEQUENCE: 5

Lys Val Ser Asn Arg Phe Ser
1               5

<210> SEQ ID NO 6
<211> LENGTH: 10
<212> TYPE: PRT
<213> ORGANISM: Artificial
<220> FEATURE:
<223> OTHER INFORMATION: Synthetic construct of LCDR3

<400> SEQUENCE: 6

Ser Gln Ser Thr His Val Pro Pro Tyr Thr
1               5                   10

<210> SEQ ID NO 7
<211> LENGTH: 354
<212> TYPE: DNA
<213> ORGANISM: Mus musculus
<220> FEATURE:
<221> NAME/KEY: CDS
<222> LOCATION: (1)..(354)

<400> SEQUENCE: 7 cag gtc caa ctc cag cag cct ggg gct gaa ctg gtg aag cct ggg gct      48
Gln Val Gln Leu Gln Gln Pro Gly Ala Glu Leu Val Lys Pro Gly Ala
1               5                   10                  15 tca gtg aag ttg tcc tgc aag gct tct ggc tac acc ttc acc agc tac      96
Ser Val Lys Leu Ser Cys Lys Ala Ser Gly Tyr Thr Phe Thr Ser Tyr
            20                  25                  30 tgg atg cac tgg gtg aag ctg agg cct gga caa ggc ttt gag tgg att     144
Trp Met His Trp Val Lys Leu Arg Pro Gly Gln Gly Phe Glu Trp Ile
        35                  40                  45 gga gag att aat cct aga aat ggt ggt act aac aac aat gag aac ttc     192
Gly Glu Ile Asn Pro Arg Asn Gly Gly Thr Asn Asn Asn Glu Asn Phe
    50                  55                  60
```

```
aag aga aag gcc aca ctg act gta gac aaa tcc tcc agc aca gcc tac      240
Lys Arg Lys Ala Thr Leu Thr Val Asp Lys Ser Ser Ser Thr Ala Tyr
 65                  70                  75                  80 atg caa ctc agc agc ctg aca tct gag gac tct gcg gtc tat tac tgt      288
Met Gln Leu Ser Ser Leu Thr Ser Glu Asp Ser Ala Val Tyr Tyr Cys
                 85                  90                  95 aca aga gat ggt aac tac gac ccc ttt gct tac tgg ggc caa ggg act      336
Thr Arg Asp Gly Asn Tyr Asp Pro Phe Ala Tyr Trp Gly Gln Gly Thr
            100                 105                 110 ctg gtc act gtc tct gca                                              354
Leu Val Thr Val Ser Ala
        115

<210> SEQ ID NO 8
<211> LENGTH: 118
<212> TYPE: PRT
<213> ORGANISM: Mus musculus

<400> SEQUENCE: 8

Gln Val Gln Leu Gln Gln Pro Gly Ala Glu Leu Val Lys Pro Gly Ala
  1               5                  10                  15

Ser Val Lys Leu Ser Cys Lys Ala Ser Gly Tyr Thr Phe Thr Ser Tyr
             20                  25                  30

Trp Met His Trp Val Lys Leu Arg Pro Gly Gln Gly Phe Glu Trp Ile
         35                  40                  45

Gly Glu Ile Asn Pro Arg Asn Gly Gly Thr Asn Asn Glu Asn Phe
     50                  55                  60

Lys Arg Lys Ala Thr Leu Thr Val Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Thr Arg Asp Gly Asn Tyr Asp Pro Phe Ala Tyr Trp Gly Gln Gly Thr
            100                 105                 110

Leu Val Thr Val Ser Ala
        115

<210> SEQ ID NO 9
<211> LENGTH: 339
<212> TYPE: DNA
<213> ORGANISM: Mus musculus
<220> FEATURE:
<221> NAME/KEY: CDS
<222> LOCATION: (1)..(339)

<400> SEQUENCE: 9 gat gtt gtg atg acc caa act cca ctc tcc ctg cct gtc agt ctt gga      48
Asp Val Val Met Thr Gln Thr Pro Leu Ser Leu Pro Val Ser Leu Gly
  1               5                  10                  15 gat caa gcc tcc atc tct tgc aga tct agt cag agc ctt gta cac agt      96
Asp Gln Ala Ser Ile Ser Cys Arg Ser Ser Gln Ser Leu Val His Ser
             20                  25                  30 aat gga aac acc tat tta cat tgg tac ctg cag aag cca ggc cag tct      144
Asn Gly Asn Thr Tyr Leu His Trp Tyr Leu Gln Lys Pro Gly Gln Ser
         35                  40                  45 cca aag ctc ctg atc tac aaa gtt tcc aac cga ttt tct ggg gtc cca      192
Pro Lys Leu Leu Ile Tyr Lys Val Ser Asn Arg Phe Ser Gly Val Pro
     50                  55                  60 gac agg ttc agt ggc agt gga tca ggg aca gat ttc aca ctc aag atc      240
Asp Arg Phe Ser Gly Ser Gly Ser Gly Thr Asp Phe Thr Leu Lys Ile
 65                  70                  75                  80
```

```
agc aga gtg gag gct gag gat ctg gga gtt tat ttc tgc tct caa agt    288
Ser Arg Val Glu Ala Glu Asp Leu Gly Val Tyr Phe Cys Ser Gln Ser
                85                  90                  95 aca cat gtt cct ccg tac acg ttc gga ggg ggg acc aag ctg gaa ata    336
Thr His Val Pro Pro Tyr Thr Phe Gly Gly Gly Thr Lys Leu Glu Ile
            100                 105                 110 aaa                                                                339
Lys

<210> SEQ ID NO 10
<211> LENGTH: 113
<212> TYPE: PRT
<213> ORGANISM: Mus musculus

<400> SEQUENCE: 10

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Tyr Thr Phe Gly Gly Gly Thr Lys Leu Glu Ile
            100                 105                 110

Lys

<210> SEQ ID NO 11
<211> LENGTH: 354
<212> TYPE: DNA
<213> ORGANISM: Artificial
<220> FEATURE:
<223> OTHER INFORMATION: Synthetic construct 6E4HV0 variable region

<400> SEQUENCE: 11
caggtccaac tcgtgcagtc tggggctgaa gtgaagaagc ctggggcttc agtgaaggtg     60
tcctgcaagg cttctggcta caccttcacc agctactgga tgcactgggt gcggcaggcc    120
cctggtcaag cttggagtg atgggtgag attaatcctc gaaatggtgg tactaacaac     180
aatgagaact tcaagcgacg ggtcacaatc actgcagaca catccaccag cacagcctac    240
atggaactca gcagcctgcg atctgaggac actgcggtct attactgtgc acgagatggt    300
aactacgacc catttgctta ctggggccaa gggactctgg tcactgtctc ttca          354

<210> SEQ ID NO 12
<211> LENGTH: 118
<212> TYPE: PRT
<213> ORGANISM: artificial
<220> FEATURE:
<223> OTHER INFORMATION: Synthetic construct of 6E4HV0 variable region

<400> SEQUENCE: 12

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30
```

Trp Met His Trp Val Arg Gln Ala Pro Gly Gln Gly Leu Glu Trp Met
         35                  40                  45

Gly Glu Ile Asn Pro Arg Asn Gly Gly Thr Asn Asn Glu Asn Phe
 50                  55                  60

Lys Arg Val Thr Ile Thr Ala Asp Thr Ser Thr Ser Thr Ala Tyr
65                   70                  75                  80

Met Glu Leu Ser Ser Leu Arg Ser Glu Asp Thr Ala Val Tyr Tyr Cys
                 85                  90                  95

Ala Arg Asp Gly Asn Tyr Asp Pro Phe Ala Tyr Trp Gly Gln Gly Thr
             100                 105                 110

Leu Val Thr Val Ser Ser
            115

<210> SEQ ID NO 13
<211> LENGTH: 339
<212> TYPE: DNA
<213> ORGANISM: Artificial
<220> FEATURE:
<223> OTHER INFORMATION: Synthetic construct of 6E4LV0 variable region

<400> SEQUENCE: 13
gatattgtga tgacccaatc tccactctcc ctgcctgtca ctcctggtga gccagcctcc      60
atctcttgcc gatctagtca gagccttgta cacagtaatg caacaccta tttacattgg     120 tacctgcaga agccaggcca gtctccacag ctcctgatct acaaagtttc caaccgattt     180
tctggggtcc cagaccggtt cagtggcagt gggtcaggga cagatttcac actcaagatc     240
agccgagtgg aggctgagga tgtgggcgtt tattactgct ctcaaagtac acatgttcct     300
ccgtacacgt tcggtcaggg gaccaagctg gaaatcaaa                           339

<210> SEQ ID NO 14
<211> LENGTH: 113
<212> TYPE: PRT
<213> ORGANISM: artificial
<220> FEATURE:
<223> OTHER INFORMATION: Synthetic construct of 6E4LV0 variable region

<400> SEQUENCE: 14

Asp Ile Val Met Thr Gln Ser Pro Leu Ser Leu Pro Val Thr Pro Gly
1                5                  10                  15

Glu Pro Ala Ser Ile Ser Cys Arg Ser Ser Gln Ser Leu Val His Ser
             20                  25                  30

Asn Gly Asn Thr Tyr Leu His Trp Tyr Leu Gln Lys Pro Gly Gln Ser
         35                  40                  45

Pro Gln Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
65                   70                  75                  80

Ser Arg Val Glu Ala Glu Asp Val Gly Val Tyr Tyr Cys Ser Gln Ser
                 85                  90                  95

Thr His Val Pro Pro Tyr Thr Phe Gly Gln Gly Thr Lys Leu Glu Ile
             100                 105                 110

Lys

<210> SEQ ID NO 15
<211> LENGTH: 118
<212> TYPE: PRT
<213> ORGANISM: artificial

```
<220> FEATURE:
<223> OTHER INFORMATION: Synthetic construct of HV12 variable region

<400> SEQUENCE: 15

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Thr Phe Thr Ser Tyr
                20                  25                  30

Trp Met His Trp Val Lys Leu Ala Pro Gly Gln Gly Phe Glu Trp Ile
            35                  40                  45

Gly Glu Ile Asn Pro Arg Asn Gly Gly Thr Asn Asn Asn Glu Asn Phe
        50                  55                  60

Lys Arg Lys Ala Thr Leu Thr Val Asp Lys Ser Ser Thr Ser Ala Tyr
65                  70                  75                  80

Met Glu Leu Ser Ser Leu Arg Ser Glu Asp Thr Ala Val Tyr Tyr Cys
                85                  90                  95

Thr Arg Asp Gly Asn Tyr Asp Pro Phe Ala Tyr Trp Gly Gln Gly Thr
            100                 105                 110

Leu Val Thr Val Ser Ser
        115

<210> SEQ ID NO 16
<211> LENGTH: 113
<212> TYPE: PRT
<213> ORGANISM: artificial
<220> FEATURE:
<223> OTHER INFORMATION: Synthetic construct of LV2a variable region

<400> SEQUENCE: 16

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
                20                  25                  30

Asn Gly Asn Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Pro Tyr Thr Phe Gly Gln Gly Thr Lys Leu Glu Ile
            100                 105                 110

Lys

<210> SEQ ID NO 17
<211> LENGTH: 113
<212> TYPE: PRT
<213> ORGANISM: artificial
<220> FEATURE:
<223> OTHER INFORMATION: Synthetic construct of LV4 variable region

<400> SEQUENCE: 17

Asp Val Val Met Thr Gln Ser Pro Leu Ser Leu Pro Val Thr Leu Gly
1               5                   10                  15

Glu Pro Ala Ser Ile Ser Cys Arg Ser Ser Gln Ser Leu Val His Ser
                20                  25                  30
```

```
Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Pro Tyr Thr Phe Gly Gln Gly Thr Lys Leu Glu Ile
            100                 105                 110

Lys
```